(12) United States Patent
Ehrhardt et al.

(10) Patent No.: US 10,456,440 B2
(45) Date of Patent: Oct. 29, 2019

(54) **ANTI-INFECTIVE STRATEGY AGAINST INFLUENZA VIRUS AND *S. AUREUS* COINFECTIONS**

(71) Applicant: Atriva Therapeutics GmbH, Tuebingen (DE)

(72) Inventors: Christina Ehrhardt, Muenster (DE); Stephan Ludwig, Muenster (DE)

(73) Assignee: ATRIVA THERAPEUTICS GMBH, Tuebingen (DE)

( * ) Notice: Subject to any disclaimer, the term of this patent is extended or adjusted under 35 U.S.C. 154(b) by 0 days.

(21) Appl. No.: 15/310,836

(22) PCT Filed: May 18, 2015

(86) PCT No.: PCT/IB2015/053644
§ 371 (c)(1),
(2) Date: Nov. 14, 2016

(87) PCT Pub. No.: WO2015/173788
PCT Pub. Date: Nov. 19, 2015

(65) Prior Publication Data
US 2017/0080045 A1    Mar. 23, 2017

(30) Foreign Application Priority Data

May 16, 2014 (LU) .......................... 92455

(51) Int. Cl.
| | | |
|---|---|---|
| *A61K 38/05* | (2006.01) | |
| *A61K 31/216* | (2006.01) | |
| *A61K 31/277* | (2006.01) | |
| *A61K 31/4439* | (2006.01) | |
| *C12Q 1/18* | (2006.01) | |
| *A61K 31/166* | (2006.01) | |
| *A61K 31/4523* | (2006.01) | |

(52) U.S. Cl.
CPC ............ *A61K 38/05* (2013.01); *A61K 31/166* (2013.01); *A61K 31/216* (2013.01); *A61K 31/277* (2013.01); *A61K 31/4439* (2013.01); *A61K 31/4523* (2013.01); *C12Q 1/18* (2013.01)

(58) Field of Classification Search
None
See application file for complete search history.

(56) References Cited

U.S. PATENT DOCUMENTS

| | | |
|---|---|---|
| 5,965,583 A | 10/1999 | Beers et al. |
| 6,040,320 A | 3/2000 | Beers et al. |
| 6,147,096 A | 11/2000 | Dodd et al. |
| 6,214,830 B1 | 4/2001 | Beers et al. |
| 6,319,921 B1 | 11/2001 | Cirillo et al. |
| 6,410,540 B1 | 6/2002 | Goehring et al. |
| 6,448,257 B1 | 9/2002 | Mavunkel et al. |
| 6,469,174 B1 | 10/2002 | Dodd et al. |
| 6,476,031 B1 | 11/2002 | Chakravarty et al. |
| 6,479,507 B2 | 11/2002 | Cheng et al. |
| 6,509,361 B1 | 1/2003 | Weier et al. |
| 6,521,655 B1 | 2/2003 | Beers et al. |
| 6,617,324 B1 | 9/2003 | Naraian et al. |
| 2002/0132843 A1 | 9/2002 | Curiel |
| 2002/0198214 A1 | 12/2002 | Mavunkel et al. |
| 2003/0232998 A1 | 12/2003 | Tepe |
| 2012/0017892 A1 | 1/2012 | Ludwig |

FOREIGN PATENT DOCUMENTS

JP      2007055983 A      3/2007

OTHER PUBLICATIONS

Gudiol et al., Pharmacotherapeutic options for treating *Staphylococcus aureus* bacteremia, Expert opinion on pharmacotherapy, vol. 18, No. 18, pp. 1947-1963.*
CDC.gov webpage, "Flu Treatment", accessed on Jun. 2, 2018. «https://www.cdc.gov/flu/treatment/index.html».*
CDC.gov webpage, "What You Should Know About Flu Antiviral Drugs", accessed on Jun. 2, 2018, https://www.cdc.gov/flu/antivirals/whatyoushould.htm.*
Bruchhagen et al., Metabolic conversion of CI-1040 turns a cellular MEK-inhibitor into an antibacterial compound, 2018, Scientific Reports, vol. 8, No. 1.*
Jia et al., c-Jun $NH_2$-terminal kinase-mediated signaling is essential for *Pseudomonas aeruginosa* ExoS-induced apoptosis. *Infect. Immun.* 71(6): 3361-70 (2003).
Zapata et al., Varicella-Zoster virus infection of human fibroblast cells activates the c-Jun N-terminal kinase pathway. *J. Virol.* 81(2): 977-90 (2007).
Alberdi et al., Binding of pigment epithelium-derived factor (PEDF) to retinoblastoma cells and cerebellar granule neurons. Evidence for a PEDF receptor. *J. Biol. Chem.* 274(44): 31605-12 (1999).
Arthur et al., Mitogen-activated protein kinases in innate immunity. *Nat. Rev. Immunol.* 13: 679-92 (2013).
Bakker et al., MEK1/2 inhibitor U0126 blocks activation of the JAK/STAT pathway in malignant plasma cell tumors. *Blood*, 100(11): Abstract 2386, 44th annual meeting of the American Society of Hematology (2002).
Borgeling et al., Inhibition of p38 mitogen-activated protein kinase impairs influenza virus-induced primary and secondary host gene responses and protects mice from lethal H5N1 infection. *J. Biol. Chem.* 289(1): 13-27 (2013).

(Continued)

*Primary Examiner* — Benjamin P Blumel
(74) *Attorney, Agent, or Firm* — Marshall, Gerstein & Borun LLP

(57) ABSTRACT

The present invention relates to MEK inhibitor, p38 inhibitor and/or NFκB inhibitor for use in a method for the prophylaxis and/or treatment of a co-infection comprising a bacterial infection and an influenza virus infection or a bacterial infection alone. Also provided are compositions comprising such inhibitors for use in the prophylaxis and/or treatment of a co-infection comprising a bacterial infection and an influenza virus infection or a bacterial infection alone. In addition an in vitro test system, wherein the test system comprises cultured cells infected with an influenza virus and a bacterium or with a bacterium alone is provided.

15 Claims, 54 Drawing Sheets

(56) References Cited

OTHER PUBLICATIONS

Branger et al., Anti-inflammatory effects of a p38 mitogen-activated protein kinase inhibitor during human endotoxemia. *J. Immunol.* 168: 4070-7 (2002).
Chertow et al., Bacterial coinfection in influenza: A grand rounds review. *JAMA*, 309: 275-82 (2013).
Dominguez et al., p38 MAP kinase inhibitors: many are made, but few are chosen. *Curr. Opin. Drug Discov. Devel.* 8(4): 421-30 (2005).
Droebner et al., Antiviral activity of the MEK-inhibitor U0126 against pandemic H1Nlv and highly pathogenic avian influenza virus in vitro and in vivo. *Antiviral Res.* 92: 195-203 (2011).
Dudek et al., The clinically approved proteasome inhibitor PS-341 efficiently blocks influenza A virus and vesicular stomatitis virus propagation by establishing an antiviral state. *J. Virol.* 84: 9439-51 (2010).
Ehrhardt et al., A new player in a deadly game: influenza viruses and the PI3K/Akt signalling pathway. *Cell. Microbiol.* 11: 863-71 (2009).
Ehrhardt et al., Bivalent role of the phosphatidylinositol-3-kinase (PI3K) during influenza virus infection and host cell defense. *Cell. Microbiol.* 8: 1336-48 (2006).
Ehrhardt et al., The NF-kappaB inhibitor SC75741 efficiently blocks influenza virus propagation and confers a high barrier for development of viral resistance. *Cell. Microbiol.* 15: 1198-211 (2013).
Ehrhardt et al., Activation of phosphatidylinositol 3-kinase signaling by the nonstructural NS1 protein is not conserved among type A and B influenza viruses. *J. Virol.* 81: 12097-100 (2007).
Ehrhardt et al., Influenza A virus NS1 protein activates the PI3K/AKT pathway to mediate antiapoptotic signaling responses. *J. Virol.* 81: 3058-67 (2007).
Eierhoff et al., The epidermal growth factor receptor (EGFR) promotes uptake of influenza A viruses (IAV) into host cells. *PLoS Pathog.* 6(9): e1001099 (2010).
Gillet et al., Factors predicting mortality in necrotizing communityacquired pneumonia caused by *Staphylococcus aureus* containing Panton-Valentine leukocidin. *Clin. Infect. Dis.* 45: 315-21 (2007).
Gilmore et al., Inhibitors of NF-κB signaling: 785 and counting. *Oncogene* 25: 6887-99 (2006).
Gilmore, Introduction to NF-kappaB: players, pathways, perspectives. *Oncogene* 25(51): 6680-4 (2006).
Gong et al., Potential targets and their relevant inhibitors in anti-influenza fields. *Curr. Med. Chem.* 16: 3716-39 (2009).
Grundmann et al., Emergence and resurgence of meticillin-resistant *Staphylococcus aureus* as a public-health threat. *Lancet* 368: 874-85 (2006).
Gupta et al., Inhibiting NFκB activation by small molecules as a therapeutic strategy. *Biochim. Biophys. Acta* 1799(10-12): 775-87 (2010).
Haasbach et al., The NF-kappaB inhibitor SC75741 protects mice against highly pathogenic avian influenza A virus. *Antiviral Res.* 99: 336-44 (2013).
Hayden, Developing new antiviral agents for influenza treatment: What does the future hold? *Clin. Infect. Dis.* 48(Suppl. 1): S3-13 (2009).
Hayden et al., Emergence and transmission of influenza A viruses resistant to amantadine and rimantadine. *Curr. Top. Microbiol. Immunol.* 176: 119-30 (1992).
Hrincius et al., CRK adaptor protein expression is required for efficient replication of avian influenza A viruses and controls JNK mediated apoptotic responses. *Cell. Microbiol.* 12: 831-43 (2010).
Ipaktchi et al., Topical p38 MAPK inhibition reduces bacterial growth on burn wounds in an in vivo burn model. *Surgery* 142(1): 86-93 (2007).
Iverson et al., Influenza virus primes mice for pneumonia from *Staphylococcus aureus*. *J. Infect. Dis.* 203: 880-8 (2011).
Iwao et al., The emerging ST8 methicillin-resistant *Staphylococcus aureus* clone in the community in Japan: associated infections, genetic diversity, and comparative genomics. *J. Infect. Chemother.* 18: 228-40 (2012).
Lee et al., MAP kinase p38 inhibitors: clinical results and an intimate look at their interactions with p38alpha protein. *Curr. Med. Chem.* 12(25): 2979-94 (2005).
Lee et al., Cooperation of TLR2 with MyD88, PI3K, and Rad in lipoteichoic acid-Induced cPLA2/COX-2-dependent airway inflammatory responses. *Am. J. Pathol.* 176: 1671-84 (2010).
Loeffler et al., Pathogenesis of *Staphylococcus aureus* necrotizing pneumonia: The role of PVL and an influenza coinfection. *Exp. Rev. Anti-Infect Ther.* 11(10): 1041-51 (2013).
Ludwig et al., MEK inhibition impairs influenza B virus propagation without emergence of resistant variants. *FEBS Lett.* 561(1-3): 37-43 (2004).
Ludwig, Targeting cell signalling pathways to fight the flu: towards a paradigm change in anti-influenza therapy. *J. Antimicrob. Chemother.* 64(1): 1-4 (2009).
Ludwig, Disruption of virus-host cell interactions and cell signaling pathways as an anti-viral approach against influenza virus infections. *Biol. Chem.* 392: 837-47 (2011).
Ludwig et al., Influenza viruses and the NF-kappaB signaling pathway—towards a novel concept of antiviral therapy. *Biol. Chem.* 389: 1307-12 (2008).
Ludwig eta l., Influenza-virus induced signaling cascades: targets for antiviral therapy? *Trends Mol. Med.* 9: 46-52 (2003).
Marjuki et al., Membrane accumulation of influenza A virus hemagglutinin triggers nuclear export of the viral genome via protein kinase Calphamediated activation of ERK signaling. *J. Biol. Chem.* 281: 16707-15 (2006).
Mazur et al., Acetylsalicylic acid (ASA) blocks influenza virus propagation via its NF-kappaB-inhibiting activity. *Cell. Microbiol.* 9: 1683-94 (2007).
Mihara et al., A potent and selective p38 inhibitor protects against bone damage in murine collagen-induced arthritis: a comparison with neutralization of mouse TNFalpha. *Br. J. Pharmacol.* 154(1): 153-64 (2008).
Moran et al., Methicillin-resistant *S. aureus* infections among patients in the emergency department. *N. Engl. J. Med.* 355: 666-74 (2006).
Morens et al., Predominantrote of bacterial pneumonia as a cause of death in pandemic influenza: implications for pandemic influenza preparedness. *J. Infect. Dis.* 198: 962-70 (2008).
Muniyappa et al., Activation of c-Jun N-terminal kinase (JNK) by widely used specific p38 MAPK inhibitors SB202190 and SB203580: A MLK-3-MKK7-dependent mechanism. *Cell. Signal.* 20(4): 675-83 (2007).
Neumann et al., Emergence and pandemic potential of swine-origin H1N1 influenza virus. *Nature* 459: 931-9 (2009).
Niemann et al., Combined action of influenza virus and *Staphylococcus aureus* panton-valentine leukocidin provokes severe lung epithelium damage. *J. Infect. Dis.* 206: 1138-48 (2012).
Oeckinghaus et al., The NF-kappaB family of transcription factors and its regulation. *Cold Spring Harb. Perspect. Biol.* 1(4): a000034 (2009).
Olschlager et al., Lung-specific expression of active Raf kinase resuits in increased mortality of influenza A virus-infected mice. *Oncogene* 23: 6639-46 (2004).
Oviedo-Boyso et al., The phosphoinositide-3-kinase-Akt signaling pathway is important for *Staphylococcus aureus* internalization by endothelial cells. *Infect. Immun.* 79: 4569-77 (2011).
Paddock et al., Myocardial injury and bacterial pneumonia contribute to the pathogenesis of fatal Influenza B Virus infection. *J. Infect. Dis.* 205: 895-905 (2012).
Park et al., Targeting the host-pathogen interface for treatment of *Staphylococcus aureus* infection. *Semin. Immunopathol.* 34: 299-315 (2012).
Parker et al., Immunopathogenesis of *Staphylococcus aureus* pulmonary infection. *Semin. Immunopathol.* 34: 281-97 (2012).
Parry, H7N9 avian flu infects humans for the first time. *BMJ* 346: f2151 (2013).
Pinto et al., The M2 proton channels of influenza A and B viruses. *J. Biol. Chem.* 281: 8997-9000 (2006).

(56) References Cited

OTHER PUBLICATIONS

Pinto et al., Controlling influenza virus replication by inhibiting its proton channel. *Mol. Biosyst.* 3: 18-23 (2007).
Planz, Development of cellular signaling pathway inhibitors as new antivirals against influenza. *Antiviral Res.* 98: 457-68 (2013).
Pleschka et al., Influenza virus propagation is impaired by inhibition of the Raf/MEK/ERK signalling cascade. *Nat. Cell Biol.* 3: 301-5 (2001).
Shilo et la., Pulmonary infections and community associated methicillin resistant *Staphylococcus aureus*: A dangerous mix? *Paediatr. Respir. Rev.* 12: 182-9 (2011).
Taubenberger et al., Influenza virus evolution, host adaptation, and pandemic formation. *Cell Host Microbe* 7: 440-51 (2010).
Thorburn et al., Pulmonary bacterial coinfection in infants and children with viral respiratory infection. *Exp. Rev. Anti Infect. Ther.* 10: 909-16 (2012).
Toth et al., Mechanism of the irreversible inhibition of human cyclooxygenase-1 by aspirin as predicted by QM/MM calculations. *J. Molec. Graph. Model.* 40: 99-109 (2013).
Tuchscherr et al., *Staphylococcus aureus* phenotype switching: an effective bacterial strategy to escape host immune response and establish a chronic infection. *EMBO Mol. Med.* 3: 129-41 (2011).
Wurzer et al., NF-kappaB-dependent induction of tumor necrosis factor-related apoptosis-inducing ligand (TRAIL) and Fas/FasL is crucial for efficient influenza virus propagation. *J. Biol. Chem.* 279: 30931-7 (2004).
Zhu et al., The nuclear factor kappa B (NF-κB) activation is required for phagocytosis of *Staphylococcus aureus* by RAW 264.7 cells. *Exp. Cell Res.* 327(2): 256-63 (2014).

\* cited by examiner

Figure 2 (cont')
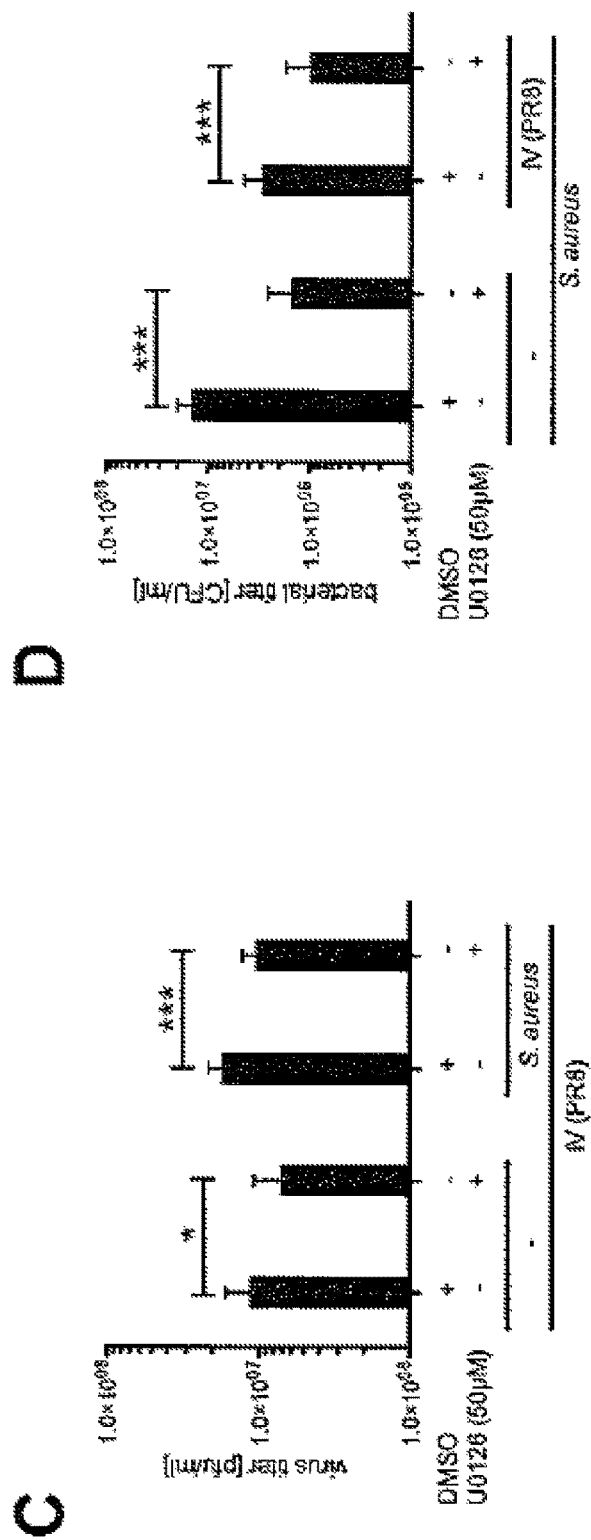

Figure 2 (cont')
E
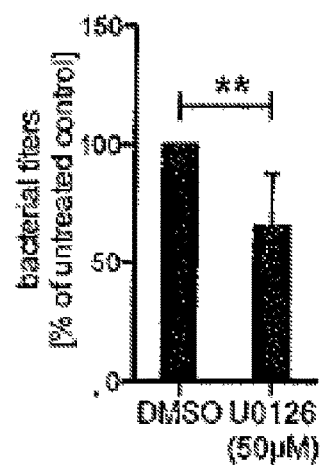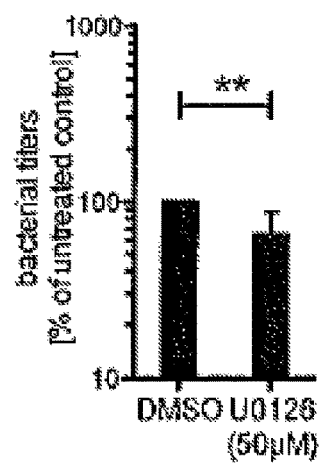

Figure 3 (cont')
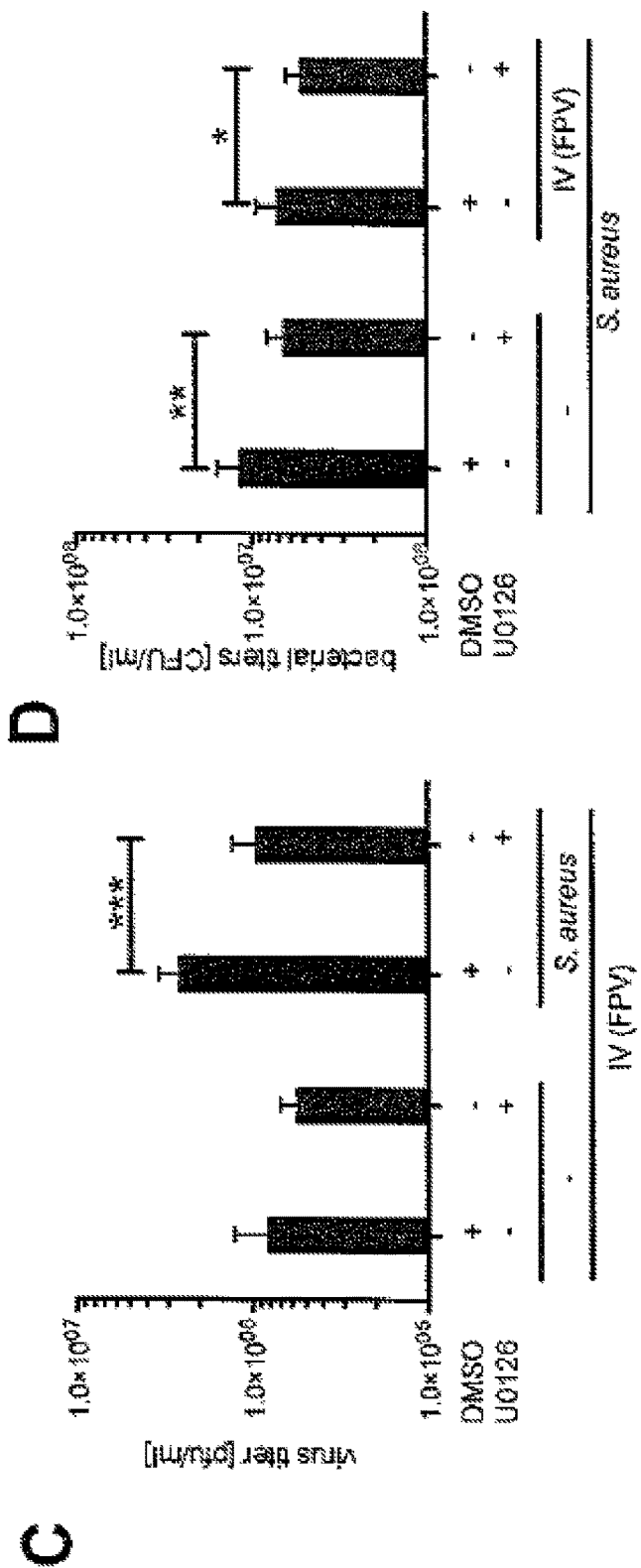

Figure 4 (cont')
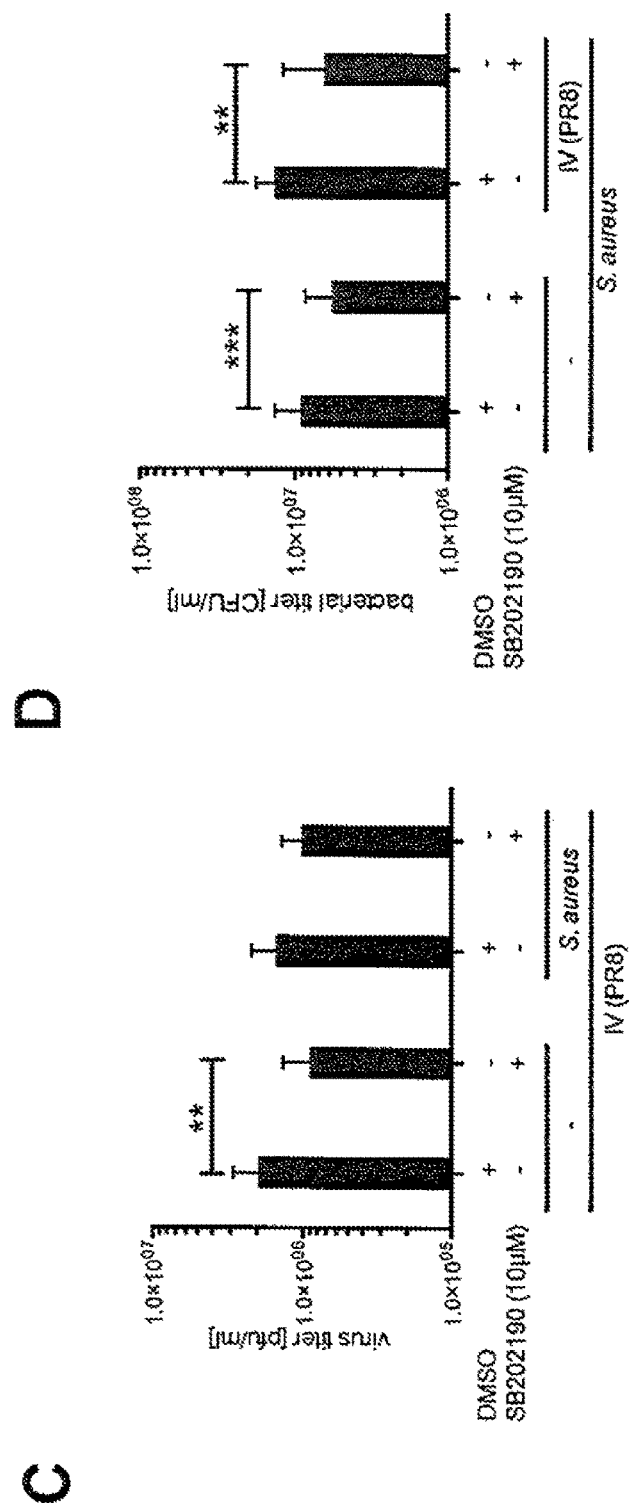

Figure 5 (cont')
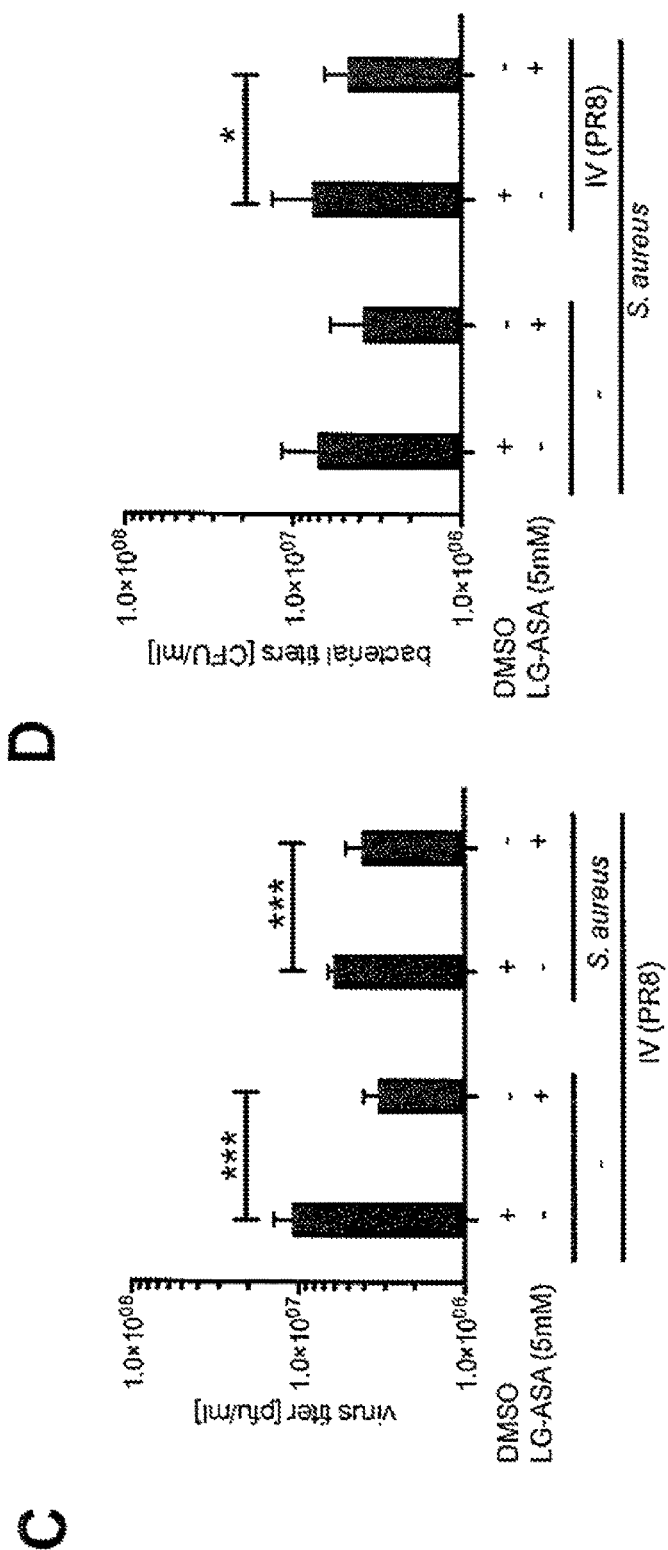

Figure 6 (cont')
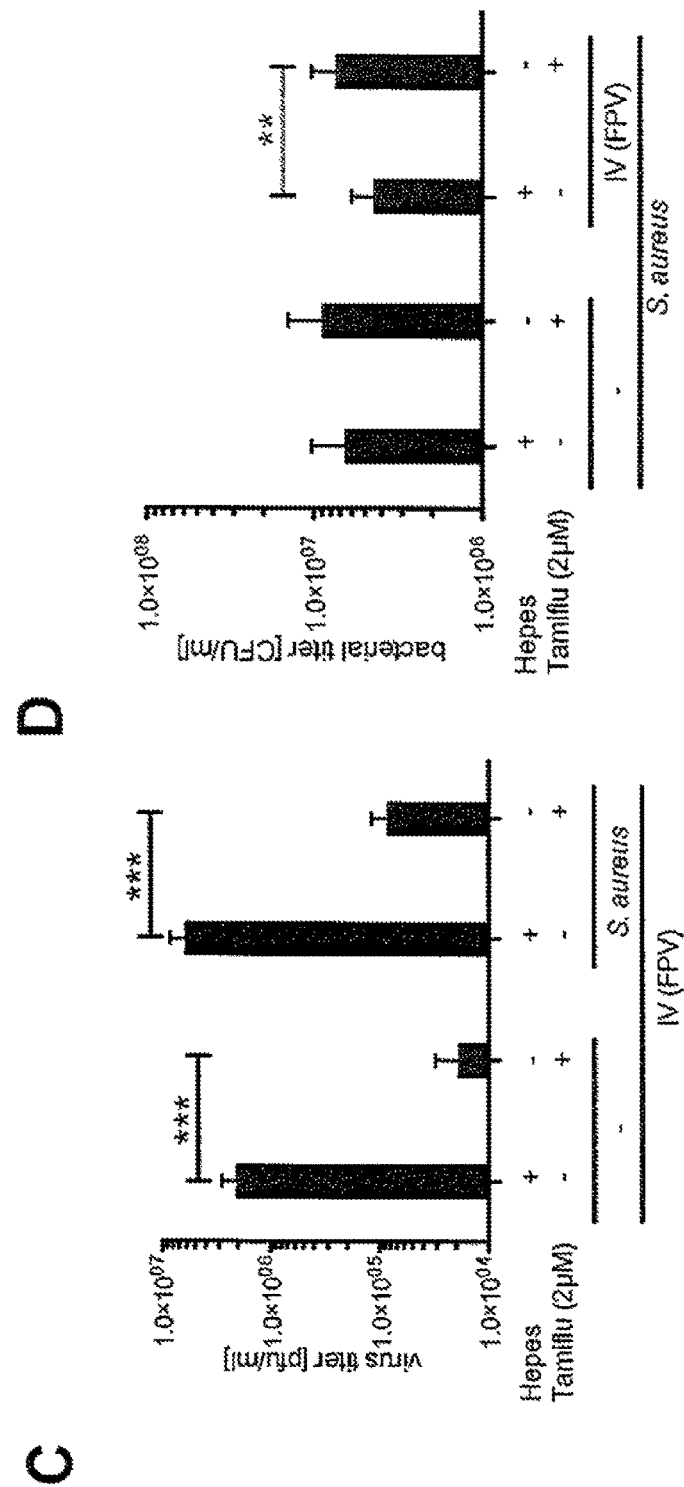

Figure 7
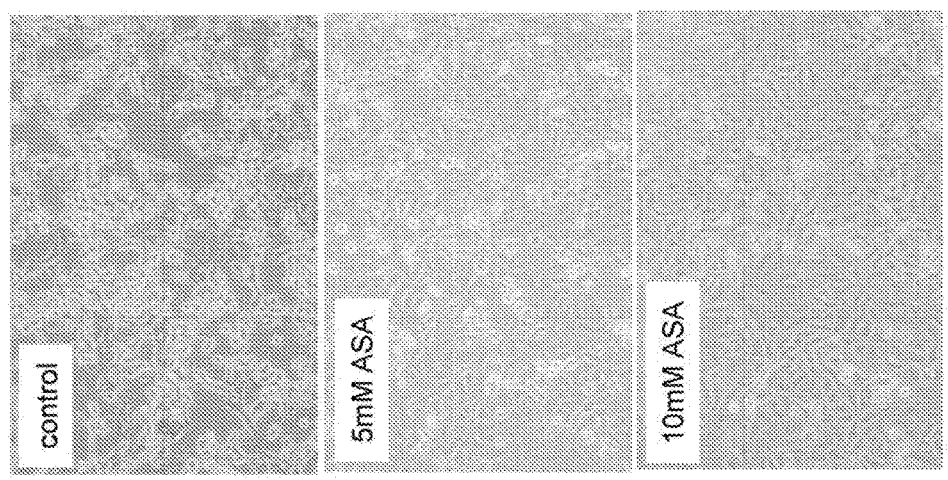
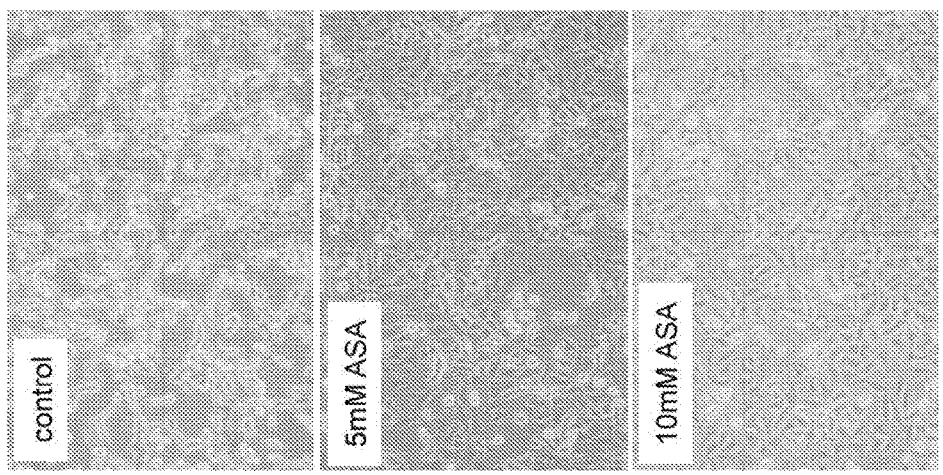

Figure 7 (cont')
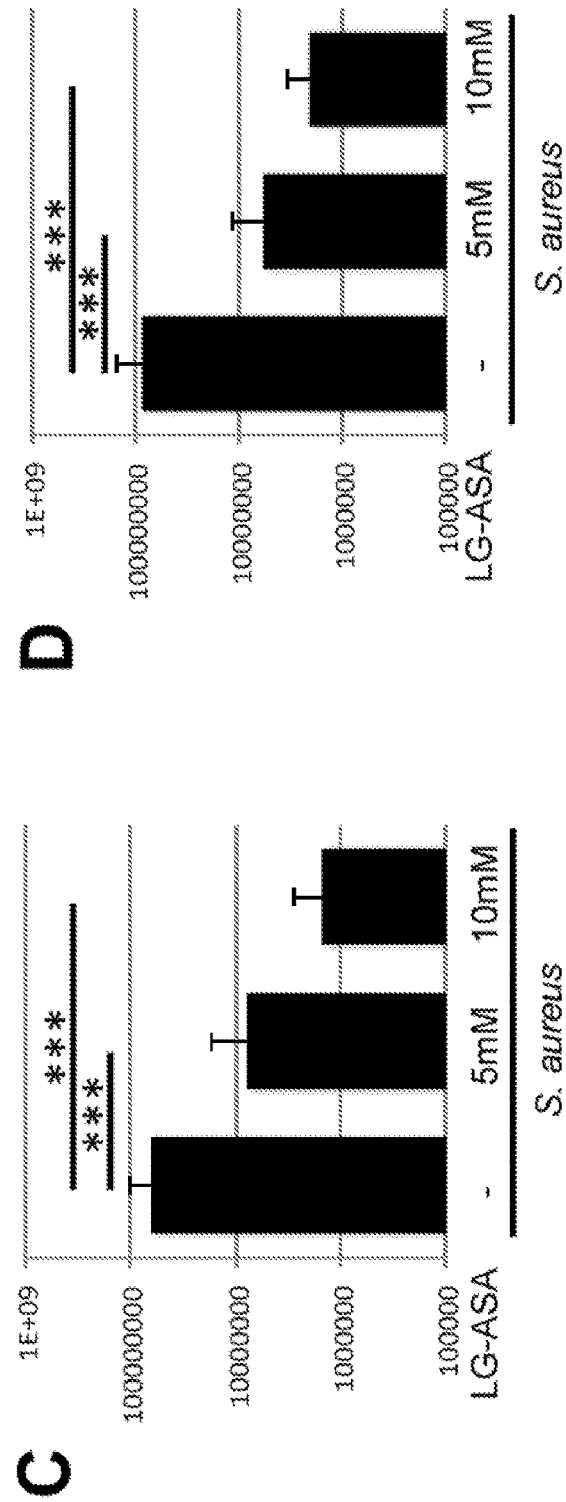

Figure 8 (Table 2)

| p38 inhibitor | Name or CAS # |
|---|---|
| LY2228820 | CAS # 862507-23-1 |
| CAY10571 | CAS # 152121-46-5 |
| CGH 2466 | CAS # 252198-68-8 |
| SB220025 | CAS # 165806-53-1 |
| Antibiotic LL Z1640-2 | CAS # 66018-38-0 |
| TAK 715 | CAS # 303162-79-0 |
| SB202190 hydrochloride | CAS # 152121-30-7 |
| SKF 86002 | CAS # 72873-74-6 |
| AMG548 | 2-[[(2S)-2-Amino-3-phenylpropyl]amino]-3-methyl-5-(2-naphthalenyl)-6-(4-pyridinyl)-4(3H)-pyrimidinone |

| CMPD-1 | 2'-Fluoro-N-(4-hydroxyphenyl)-[1,1'-biphenyl]-4-butanamide |
|---|---|
| EO 1428 | 2-Methylphenyl)-[4-[(2-amino-4-bromophenyl)amino]-2-chlorophenyl]methanone |
| JX 401 | 1-(2-Methoxy-4-(methylthio)benzoyl]-4-(phenylmethyl)piperidine |
| ML 3403 | [5-[4-(4-Fluorophenyl)-2-methylthio-1H-imidazol-4-yl]-N-(1-phenylethyl)-2-pyridinamine |
| RWJ 67657 | 4-[4-(4-Fluorophenyl)-1-(3-phenylpropyl)-5-(4-pyridinyl)-1H-imidazol-2-yl]-3-butyn-1-ol |
| SB 202190 | 4-[4-(4-Fluorophenyl)-5-(4-pyridinyl)-1H-imidazol-2-yl]phenol |
| SB 203580 | 4-[5-(4-Fluorophenyl)-2-[4-(methylsulfonyl)phenyl]-1H-imidazol-4-yl]pyridine |
| SB 203580 hydrochloride | 4-[5-(4-Fluorophenyl)-2-[4-(methylsulphonyl)phenyl]-1H-imidazol-4-yl]pyridine hydrochloride |
| SB 239063 | trans-4-[4-(4-Fluorophenyl)-5-(2-methoxy-4-pyrimidinyl)-1H-imidazol-1-yl]cyclohexanol |

Figure 8 (cont'/Table 2)

| SCIO 469 hydrochloride | 6-Chloro-5-[[(2R,5S)-4-[(4-fluorophenyl)methyl]-2,5-dimethyl-1-piperazinyl]carbonyl]-N,N,1-trimethyl-α-oxo-1H-Indole-3-acetamide hydrochloride |
|---|---|
| SX 011 | 6-Chloro-5-[[4-[(4-fluorophenyl)methyl]-1-piperidinyl]carbonyl-N,N,1-trimethyl-α-oxo-1H-indole-3-acetamide |
| TAK 715 | N-[4-[2-Ethyl-4-(3-methylphenyl)-5-thiazolyl]-2-pyridinyl]benzamide |
| VX 702 | 6-[(Aminocarbonyl)(2,6-difluorophenyl)amino]-2-(2,4-difluorophenyl)-3-pyridinecarboxamide |
| SB 203580 | |
| Tie2 Kinase Inhibitor | CAS # 948557-43-5 |
| 2-(4-Chlorophenyl)-4-(fluorophenyl)-5-pyridin-4-yl-1,2-dihydropyrazol-3-one | 2-(4-Chlorophenyl)-4-(fluorophenyl)-5-pyridin-4-yl-1,2-dihydropyrazol-3-one |
| VX 745 | CAS # 209410-46-8 |

| Pamapimod | 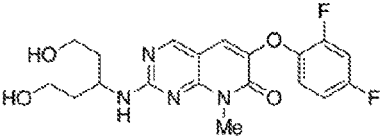 6-(2,4-Difluorophenoxy)-2-[[3-hydroxy-1-(2-hydroxyethyl)propyl]amino]-8-methylpyrido[2,3-d]pyrimidin-7(8H)-one; R 1503; Ro 4402257; |
|---|---|
| Losmapimod (GW856553) | 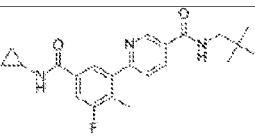 6-[5-(cyclopropylcarbamoyl)-3-fluoro-2-methylphenyl]-N-(2,2-dimethylpropyl)pyridine-3-carboxamide |
| Dilmapimod (SB681323) | 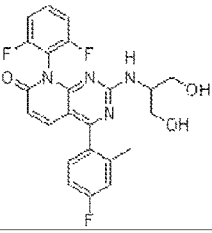 |

Figure 8 (cont'/Table 2)
| | |
|---|---|
| | 8-(2,6-difluorophenyl)-2-((1,3-dihydroxypropan-2-yl)amino)-4-(4-fluoro-2-methylphenyl)pyrido[2,3-d]pyrimidin-7(8H)-one<br>CAS#: 444606-18-2 |
| Doramapimod (BIRB 796) | 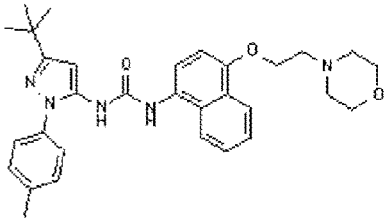<br>CAS 285983-48-4<br>C31H37N5O3 |
| BMS-582949 | 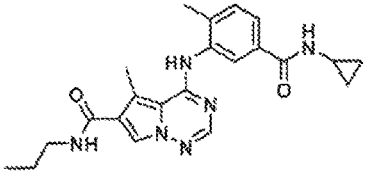 |
| PH797804 | 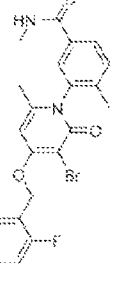 |
| ARRY-797 | |
| SCIO-469 | 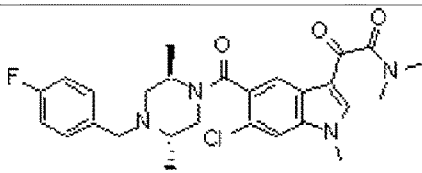<br>CAS 309913-83-5<br>C27H30ClFN4O3 |

Figure 9 (Table 3) NFκB inhibitors

| A. Upstream NF-kB | Kahweol | AIDCA derivative | Catalposide | E-73 | RelA peptides (P1 & P6) |
|---|---|---|---|---|---|
| Natural product | Kava derivatives | TDZD | Cyclolinteinone | Ecabet sodium | Viral Protein |
| 15d-PGJ(2) | Licorce extracts | TPCA-1 | Dihydroartean nium | Gabexate mesilate | 3C protease (EMC virus) |
| Calagualine | Manumycin A | Pyridine derivatives | Docosahexa enoic acid | Glimepiride | Canine Distemper Virus |
| Conophylline | Monochloramine | ACHP | Emodin | Hypochlorite | MNF (myxoma virus) |
| Evodiamine | N-acetyl cysteine | Acrolein | Ephedrae herba (Mao) extract | Losartin | Protein |
| Geldanamycin | Nitric oxide | AGRO100 | Equol | LY294002 | C5a |
| Perrilyl alcohol | Nitrosylcobalamin | Amino-pyrimidine | Erbstatin | Pervanadate | DQ 65-79 |
| PSK | Oleandrin | AS602868 | Estrogen | Phenylarsine oxide | Fox1j |
| Rocaglamides | Omega 3 fatty acids | Aspirin | Ethacrynic acid | Phenytoin | GILZ |
| Viral protein | ox-LDL | Azidothymidine | Fosfomycin | Ro106-9920 | HSCO |
| Adenovirus E1A | Panduratin A | BAY-11-7082 | Fungal gliotoxin | Sabaeksan | HSP-72 |
| NS5A (Hep-C virus) | PEITC | BAY-11-7083 | Gamisanghyul yunbueum | U0126 (MEK inhibitor) | Interleukin-10 |
| Protein | Petrosa spongiolide M | Benzoimi dazole derivative | Genipin | Others | Interleukin-11 |
| Erbin over expression | Phytic acid | Benzyl isothiocyanate | Genistein | Vagus nerve stimulation | Interleukin-13 |
| Golli BG21 | Piceatannol | BMS-345541 | Glabridin | Low level laser therapy | MTS-SR-IκBα |
| KSR | Pinosylvin | Carboplatin | Glucosamine sulfate | Zinc | Onconase |
| MAST205 | Plagius flosculosus extract | CDDO-Me | Glutamine | O. IκB upregulators/ | RASSF1A gene |
| NPM-ALK oncoprotein | Plumbagin | CHS 828 | Gumiganghwa Itang | NF-κB translocation | ROR-alpha |
| Hep-C virus protease | Pomegranate extract | Compound 5 | Isomallotochr omanol | Natural product | Surfactant protein A |
| PEDF | Prostaglandin A1 | Compound A | Isomallotochr omene | PGG | TAT-SR-IκBα |

Figure 9 (cont'/Table 3)

| Rituximab | Quercetin | Cyclopentenones | Kochia scoparia fruit extract | 15-deoxyspergualin | ZAS3 protein |
|---|---|---|---|---|---|
| TNAP | Rengyolone | CYL-19s | L-ascorbic acid | 2',8"-biapigenin | ZUD protein |
| Synthetic | Rosmarinic acid | CYL-26z | Leflunomide metabolite | SF (from Pteri syeminpinnata) | β-amyloid protein |

| Betaine | Rottlerin | Diaylpyridine derivative | Melatonin | Agastache rugosa leaf extract | Synthetic |
|---|---|---|---|---|---|
| Desloratadine | Saikosaponin-d | DPE | Midazolam | Alginic acid | BMD |
| LY29 and LY30 | Salvia miltiorrhiza extract | Epoxyquinone | Momordin I | Antrodia camphorata extract | Carbaryl |
| MOL 294 ** | Sanguinarine | Gabexate mesilate | Morinda officinalis extract | Apigenin | CGS 25462 |
| Pefabloc | SAm extract | Gleevec | Mosla dianthera extract | Astragaloside IV | DHMEQ |
| Rhein | Staurosporine | Hydroquinone | Opuntia ficus indica extract | ATS14 (serratamolide) | Diltiazem |
| SMI and FP | Sesquiterpene lactones | Ibuprofen | Platycodin saponins | Atorvastatin | Dioxin |
| B. IKK activity and IkB phosphorylation | Scoparone | IQCAD | Polymyxin B | Blue honey suckle extract | Dipyridamole |
| | Silibinin | Indolecarboxamide | Poncirus trifoliata fruit extract | Buthus martensi extract | Disulfiram |
| Natural product | Silymarin | Isobutyl nitrite | Probiotics | Cantharidin | Enalapril |
| (S)-gingerol | Sulforaphane | Jesterone dimer | Prostaglandin | Chiisanoside | mEET |
| 1'-Acetoxychavicol acetate | Sulindac | 15-deoxyspergualine analog | Resiniferatoxin | Clarithromycin | Fluvastatin |
| 20(S)-Protopanaxatriol | Tetrandine | Methotrexate | Stinging nettle extracts | Cornus officinalis extract | Indole-3-carbinol |
| 4-Hydroxynonenal | Theaflavin | MLB120 | Thiopental | Eriocalyxin B | ISH-23 |
| Acetyl-boswellic acids | Thienopyridine | Monochloramine | Tipifarnib | Gangliosides | KL-1156 |
| Anandamide | Tilianin | MX781 (Retinoid antagonist) | Titanium | Glucocorticoids | Leflunomide |
| Anethole | Ursolic acid | 4-HPR | TNP-470 | HP extracts | Levamisole |
| Apigenin | Vesnarinone | Nafamostat mesilate | Trichomomas vaginalis | Hirsutenone | MEB |
| Artemisia vestita1 | Wedelolactone | NSAIDs | TG-rich lipoproteins | Human breast milk | Moxifloxacin |
| Baoganning | Withanolides | PS-1145 (MLN1145) | Ursodeoxycholic acid | JM34 | Omapatrilat |
| Betulinic acid | Xanthoangelol D | PQD | Xanthium strumarium extract | KIOM-79 | R-etodolac |

Figure 9 (cont'/Table 3)

| Black raspberry extracts | Zerumbone | Pyridooxazinone derivative | β-PEITC | Leptomycin B | Rolipram |
|---|---|---|---|---|---|
| Buddlejasaponin IV | β-carboline | SC-514 | 8-MSO | Neomycin | SC236 (COX-2 inhibitor) |
| Cacospongionolide B | γ-mangostin | Scytonemin | β-lapachone | Nucling | Triflusal |
| Calagualine | γ-Tocotrienol | Sodium salicylate | Peptide | Oregonin | Volatile anesthetics |
| Cardamomin | Peptide | Statins (several) | Penetratin | OXPAPC | E. NF-kB DNA-binding |

| Cardamonin | IKKβ peptide | Sulfasalazine | VIP | Paeoniflorin | Inorganic Complex |
|---|---|---|---|---|---|
| Casparol | NEMO CC2-LZ peptide | Sulfasalazine analogs | Protein | Phallacidin | Metals (chromium, cadmium, gold, lead, mercury, zinc, arsenic) |
| Cobrotoxin | Protein | Survanta | Activated protein C | Piperine | |
| Cycloepoxydon | Anti-thrombin III | Thalidomide | HSP-70 | Pitavastatin | Natural product |
| Decursin | Chorionic gonadotropin | THI 52 | Interleukin-13 | Platycodi radix extract | Actinodaphine |
| Dehydroascorbic acid | FHIT | YC-1 | Intravenous Ig | Probiotics | Anthocyanins |
| Dexanabinol | HB-EGF | Others | Murr1 gene product | Rapamycin | Arnica montana extract |
| Digitoxin | Hepatocyte growth factor | Lead | Neurofibromatosis-2 protein | Rhubarb aqueous extract | Artemisinin |
| Diosgenin | Interferon-α | Mild hypothermia | PACAP | Salvia miltiorrhoza extract | Baicalein |
| Diterpenes | Interleukin-10 | Saline (low Na+) | SAIF | SH extract | Bambara groundnut |
| Docosahexaenoic acid | PAN1 | C. IkB degradation | ST2 (IL-1-like receptor) | Selenomethionine | β-lapachone |
| Falcarindol | PTEN | Natural product | α-MSH | Shenfu | Biliverdin |
| Flavopiridol | SOCS1 | 5'-methylthioadenosine | γ-glutamylcysteine synthetase | Sophorae radix extract | Brazilian |
| Furonaphthoquinone | Viral Protein | Artemisia iwayomogi extract | Bacterial/Viral Protein | Sopoongsan | Calcitriol |
| Garcinone B | Adenovirus | Alachlor | K1L (Vaccinia virus protein) | Sorbus commixta extract | Campthothecin |
| Glossogyne tenuifolia extract | Core protein (Hep-C virus) | Amentoflavone | Nef (HIV-1) | Sphondin | Sutherlandia frutescens |
| Glycine chloramine | Cytomegalovirus | Antrodia camphorata# | Vpu protein (HIV-1) | T. polyglycosides | Capsiate |
| Guggulsterone | E7 (Papillomavirus) | Artemisia capillaries extract | YopJ | Younggaechulgam-tang | Catalposide |
| Herbimycin A | MC159 | Aucubin | Synthetic | α-pinene | Cat's claw bark |

Figure 9 (cont'/Table 3)

| Honokiol | MC160 | Baicalein | 1-Bromopropane | Peptide | Cheongyeolsaseuptang |
|---|---|---|---|---|---|
| Hypoestoxide | NS5B (Hep-C virus) | Blackberry extract | Acetaminophen | NCPP | Chitosan |
| Indirubin-3'-oxime | vIRF3 (KSHV) | Buchang-tang | Diamide | PN50 | Chicory root |
| Isorhapontigenin | Synthetic | Capsaicin | Dobutamine | | CSPDP |
| Clarithromycin | AIM2 overexpression | Raxofelast | F. Proteasome/protease | Mangifera indica bark | |
| Cloricromene | Angiopoietin-1 | Ribavirin | Natural product | extract | |

| | | | product | | |
|---|---|---|---|---|---|
| C-K and Rh(2) | Antithrombin | Rifamides | Cyclosporin A | Mangiferin | |
| Cortex cinnamomi extract | AvrA protein (Salmonella) | Ritonavir Rosiglitazone | Lactacystine β-lactone | Melatonin Mn-SOD | |
| Cryptotanshinone | β-catenin | Roxithromycin | Peptide | Mulberry anthocyanins | |
| Cytochalasin D | Bromelain | DAAS | ALLnL | Myricetin | |
| Black rice extract | CaMKK | Serotonin derivative | LLM | N-acetyl-L-cysteine | |
| Danshenshu | CD43 overexpression | Simvastatin | Ubiquitin ligase | Nacyselyn | |
| Diterpenoids | FLN29 overexpression | SM-7368** | Z-LLL | Naringin | |
| Ent-kaurane diterpenoids | FLIP | T-614 | Z-LLnV | N-ethyl-maleimide | |
| Epinastine hydrochloride | G-120 | Sulfasalazine | Synthetic | Nitrosoglutathione | |
| Epoxyquinol A | Gax (homeobox protein) | SUN C8079 | APNE | NDGA | |
| Erythromycin | HIV-1 Resistance Factor | Triclosan plus CPC | Boronic acid peptide | Ochnaflavone | |
| Evodiamine | Interleukin 4 | Tobacco smoke | BTEE | Orthophenanthroline | |
| Fish oil | SspH1 and IpaH9.8 | Verapamil | 3,4-dichloroisocoumarin | Phenylarsine oxide | |

Figure 9 (cont'/Table 3)

| Fomes fomentarius extracts | NDPP1 (CARD protein) | Others | Deoxyspergualin | PhIP | |
|---|---|---|---|---|---|
| | Overexpressed ZIP1 | Heat (fever-like) | DFP | Phyllanthus urinaria | |
| Fucoidan | p8 | Hypercapnic acidosis | Disulfiram | PMC | |
| Gallic acid | p202a | Hyperosmolarity | FK506 (Tacrolimus) | PTX | |
| Ganoderma lucidum | p21 (Rec) | Hypothermia | Bortezomib | Pyrithione | |
| Garcinol | PIAS1 | Alcohol | Salinosporamide A | Pyrrolinedithiocarbamate | |
| Geranylgeraniol | Pro-opiomelanocortin | E. NF-kB transactivation | TLCK | Quercetin | |
| Ginkgolide B | PYPAF1 protein | Natural products | TPCK | Quinozolines | |
| Glycyrrhizin | Raf Kinase inhibitor | 4'-DM-6-Mptox | G. Antioxidants | Rebamipide | |
| Halofuginone | protein Rhus verniciflua | 4-phenylcoumarins | 23-hydroxyursolic acid | Red wine | |
| Hematein | fruits | AHUP | Aged garlic extract | Redox factor 1 | |

Figure 9 (cont'/Table 3)

| | | | | | |
|---|---|---|---|---|---|
| Herbal compound 861 | SLPI | Adenosine | Anetholdithiolthione | Resveratrol | |
| Hydroxyethyl starch | Siah2 | c-AMP | Apocynin | Ginseng derivative | |
| Hydroxyethylpuerarin | SIRT1 Deacetylase | Artemisia sylvatica extract | Apple juice/extracts | Rotenone | |
| Hypericin | overexpression | Bifodobacteria | Arctigenin | Roxithromycin | |
| Kamebakaurin | Siva-1 | Blueberry & berry mix | Aretemisa p7F | S-allyl-cysteine | |
| Linoleic acid | Solana nigrum L. | BSASM | Astaxanthin | Sauchinone | |
| Lithospermi radix | Surfactant protein A | BF phenylpropanoids | Benidipine | Spironolactone | |
| Macrolide antibiotics | Tom1 overexpression | cPrG.HC | bis-eugenol | Strawberry extracts | |
| Mediterranean plant extracts | Transdominant p50 | Seaweed extract | BG compounds | Taxifolin | |
| | Uteroglobin | Fructus benincasae extract | BHA | Tempol | |
| 2-methoxyestradiol | VEGF | Glucocorticoids | CAPE | Tepoxaline | |
| 6-MITC | Synthetic | Gypenoside XLIX | Carnosol | tert-butyl hydroquinone | |

| | | | | | |
|---|---|---|---|---|---|
| Nicotine | ADP ribosylation inhibitor | Kwei Ling Ko3 | Carvedilol | Tetracylic A | |
| Ochna macrocalyx bark ext. | 7-amino-4-methylcoumarin | LC root | Catechol derivatives | Vitamin B6 | |
| | Amrinone | Luteolin | Celasterol | Vitamin C | |
| Oridonin | Atrovastat | Manassantins A,B | Cepharanthine | Vitamin D | |
| PC-SPES (8 herb mixture) | Benfotiamine | MI bark extract | Chlorogenic acid | Vitamin E derivatives | |
| PGG | Benzamide | Mesuol | Chlorophyllin | Wogonin | |
| Pepluanone | Bisphenol A | Nobiletin | Cocoa polyphenols | xanthohumol | |
| Phyllanthus amarus extracts | Caprofen | Phomol | Curcumin | Yakuchinone A, B | |
| | Carbocisteine | Psychosine | DHEA | α-lipoic acid | |
| Plant compound A | Celecoxib | Qingkailing | DHEA sulfate | α-tocopherol | |
| Polyozellin | Germcitabine | Saucerneol D & E | Dehydroevodiamine | α-torphryl acetate | |
| Prenylbisabol | Cinnamaldeh | Shuanghuanglia | Demethyltra | α-torphryl | |

Figure 9 (cont'/Table 3)

| ane 3 | yde | n# | xillagenin | succinate | |
|---|---|---|---|---|---|
| Prostaglandin E2 | 2-methoxy CNA | Smilax bockii extract | Diethyldithio carbamate | β-Carotene | |
| PSK | 2-hydroxy CNA | Trilinolein | Diferoxamine | | |
| Quinic acid | CDS | Uncaria tomentosum extract | Dihydroisoeugenol | | |
| Sanggenon C | CP Compound | WS extracts | Dihydrolipoic acid | | |
| Sesamin | Cyanoguanidine | Wortmannin | Dilazep | | |
| Shen-Fu | HMP | α-zearalenol | Fenofibric acid | | |
| Silibinin | α-difluoromethylornithine | Viral Protein | DMDTC | | |
| Sinomenine | DTD | BZLF1 (EBV protein) | Dimethylsulfoxide | | |
| Sword brake fern extract | Evans Blue | SH gene products (PMV) | Disulfiram | | |
| Tanacetum larvatum extract | Evodiamine | Protein | Ebselen | | |
| Tansinones | Fenoldopam | Antithrombin | Edaravone | | |
| | FEX | NF-kappaB-repression factor | EGTA | | |
| Taurine + niacine | Fibrates | PIAS3 | EPC-K1 | | |
| TZD MCC-555 | FK778 | PTX-B | Epigallocatechin-3-gallate | | |
| Trichostatin A | Flunixin meglumine | Synthetic | Ergothioneine | | |
| Triptolide | Flurbiprofen | 17-AAG | Ethyl pyruvate | | |
| Tyrphostin AG-126 | Hydroquinone | TMFC | Ganoderma lucidum polysaccharides | | |
| Ursolic acid | IMD-0354 | AQC derivatives | | | |
| Withaferin A | JSH-21 | 9-aminoacridine | Garcinol | | |
| Xanthohumol | KT-90 | derivatives | γ-glutamylcysteine synthetase | | |
| Xylitol | Lovastatin | Chromene derivatives | Ginkgo biloba extract | | |

Figure 9 (cont'/Table 3)

| Yan-gan-wan# | Mercaptopyrazine | D609 | Glutathione | | |
| Yin-Chen-Hao# | Mevinolin, | Dimethylfumarate | Hematein | | |

| Yucca schidigera extract | Monoethylfumarate | EMDPC | Hydroquinone | | |
|---|---|---|---|---|---|
| Peptide | Moxifloxacin | Histidine | Hydroquinone | | |
| Ghrelin | Nicorandil | HIV-1 PI | IRFI 042 | | |
| Peptide YY | Nilvadipine | Mesalamine | Iron tetrakis | | |
| Rapamycin | NO-ASA | PEITC | Isovitexin | | |
| Viral Protein | Panepoxydone | Pranlukast | Kangen-karyu extract | | |
| African Swine Fever virus | Peptide nucleic acids | RO31-8220 (PKC inhibitor) | Ketamine | | |
| Sendai Virus-C,V proteins | Perindopril | | Lacidipine | | |
| E1B (Adenovirus) | PAD | SB203580 (MAPK inhibitor) | Lazaroids | | |
| ICP27 (HSV-1) | α-PBN | Tetrathiomolybdate | L-cysteine | | |
| H4/N5 (bracovirus) | Pioglitazone | Tranilast | Ligonberries | | |
| NS3/4A (Hep-C) | Pirfenidone | Troglitazone | Lupeol | | |
| Protein | PNO derivatives | Others | Magnolol | | |
| Adiponectin | Quinadril | Low gravity | Maltol | | |

Figure 10 (Table 4)

| NFκB inhibitor | Name or CAS # |
|---|---|
| MG 132 | N-[(Phenylmethoxy)carbonyl]-L-leucyl-N-[(1S)-1-formyl-3-methylbutyl]-L-leucinamide |
| TPCA-1 | 2-[(Aminocarbonyl)amino]-5-(4-fluorophenyl)-3-thiophenecarboxamide |
| PCTC | Pyrrolidinedithiocarbamate ammonium |
| IMD 0354 | N-(3,5-Bis(trifluoromethyl)phenyl)-5-chloro-2-hydroxybenzamide |
| Luteolin | 2-(3,4-Dihydroxyphenyl)-5,7-dihydroxy-4H-1-benzopyran-4-one |
| Caffeic acid phenethyl ester/ CAPE | 3-(3,4-Dihydroxyphenyl)-2-propenoic acid 2-phenylethyl ester |
| Cardamonin | (2E)-1-(2,4-Dihydroxy-6-methoxyphenyl)-3-phenyl-2-propen-1-one |
| PF 184 | 6-[[[5-Chloro-2-[3,4-dimethyl-3,4-bis(hydroxymethyl)-1-pyrrolidinyl]-4-pyridinyl]carbonyl]amino]-1-(4-fluorophenyl)-4,5-dihydro-1H-benz[g]indazole-3-carboxamide |
| IKK 16 | N-(4-Pyrrolidin-1-yl-piperidin-1-yl)-[4-(4-benzo[b]thiophen-2-yl-pyrimidin-2-ylamino)phenyl]carboxamide hydrochloride |
| SC 514 | 4-Amino-[2',3'-bithiophene]-5-carboxamide |
| Withaferin A | (4β,5β,6β,22R)-5,6-Epoxy-4,22,27-trihydroxy-1-oxoergosta-2,24-dien-26-oic acid 6-lactone |
| Arctigenin | (3R,4R)-4-[(3,4-Dimethoxyphenyl)methyl]dihydro-3-[(4-hydroxy-3-methoxyphenyl)methyl]-2(3H)-furanone |
| Bay 11-7085 | (2E)-3-[[4-(1,1-Dimethylethyl)phenyl]sulfonyl]-2-propenenitrile |
| PSI | N-[(Phenylmethoxy)carbonyl]-L-isoleucyl-L-α-glutamyl-tert-butyl ester-N-[(1S)-1-formyl-3-methylbutyl]-L-alaninamide |
| PR 39 (porcine) | Arg-Arg-Arg-Pro-Arg-Pro-Pro-Tyr-Leu-Pro-Arg-Pro-Arg-Pro-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro-$NH_2$ |
| Ro 106-9920 | 6-(Phenylsulfinyl)tetrazolo[1,5-b]pyridazine |
| Bay 11-7821 | (2E)-3-[(4-Methylphenyl)sulfonyl]-2-propenenitrile |

Figure 10 (cont'/Table 4)

| | |
|---|---|
| ML-130 | 1-[(4-Methylphenyl)sulfonyl]-1H-benzimidazol-2-amine |
| Celastrol | (9β,13α,14β,20α)-3-Hydroxy-9,13-dimethyl-2-oxo-24,25,26-trinoroleana-1(10),3,5,7-tetraen-29-oic acid |
| Tanshinone IIA | 6,7,8,9-Tetrahydro-1,6,6-trimethylphenanthro[1,2-b]furan-10,11-dione |
| HU 211 | (6aS,10aS)-3-(1,1-Dimethylheptyl)-6a,7,10,10a-tetrahydro-1-hydroxy-6,6-dimethyl-6H-dibenzo[b,d]pyran-9-methanol |
| Gliotoxin | (3R,5aS,6S,10aR)-2,3,5a,6-Tetrahydro-6-hydroxy-3-(hydroxymethyl)-2-methyl-10H-3,10a-epidithiopyrazino[1,2-a]indole-1,4-dione |
| CID 2858522 | 1-[3,5-Bis(1,1-dimethylethyl)-4-hydroxyphenyl]-2-[2-[(3-hydroxypropyl)amino]-5,6-dimethyl-1H-benzimidazol-1-yl]ethanone |
| Honokiol | 5,3'-Diallyl-2,4'-dihydroxybiphenyl |
| Andrographolide | (3E,4S)-3-[2-[(1R,4aS,5R,6R,8aS)-Decahydro-6-hydroxy-5-(hydroxymethyl)-5,8a-dimethyl-2-methylene-1-naphthalenyl]ethylidene]dihydro-4-hydroxy-2(3H)-furanone |
| 10Z-Hymenialdisine | (4Z)-4-(2-Amino-1,5-dihydro-5-oxo-4H-imidazol-4-ylidene)-2-bromo-4,5,6,7-tetrahydropyrrolo[2,3-c]azepin-8(1H)-one |
| ACHP | 2-Amino-6-[2-(cyclopropylmethoxy)-6-hydroxyphenyl]-4-(4-piperidinyl)-3-pyridinecarbonitrile |
| Pristimerin | (9β,13α,14β,20α)-3-Hydroxy-9,13-dimethyl-2-oxo-24,25,26-trinoroleana-1(10),3,5,7-tetraen-29-oic acid methyl ester |
| Sulfasalazine | 5-[[4-(2-Pyridylsulfamoyl)phenyl]azo]salicylic acid |
| ML 120B dihydrochloride | N-(6-Chloro-7-methoxy-9H-pyrido[3,4-b]indol-8-yl)-2-methyl-3-pyridinecarboxamide dihydrochloride |
| Amlexanox | 2-Amino-7-(1-methylethyl)-5-oxo-5H-[1]benzopyrano[2,3-b]pyridine-3-carboxylic acid |
| 9-Methylstreptimidone | CAS # 51867-94-8 |
| N-Stearoyl phytosphingosine | CAS # 34354-88-6 |
| 2-(1,8-naphthyridin-2-yl)-Phenol | CAS # 65182-56-1 |
| 5-Aminosalicylic acid | CAS # 89-57-6 |

Figure 10 (cont'/Table 4)
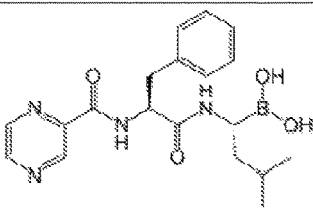

Figure 10 (cont'/Table 4)

| | |
|---|---|
| curcumin | (1E,6E)-1,7-Bis-(4-hydroxy-3-methoxyphenyl)-hepta-1,6-dien-3,5-dion |
| aspirin | acetylsalicylic acid |
| salsalate | 2-(2-Hydroxybenzoyl)oxybenzoic acid |
| resveratrol | 3,5,4'-trihydroxy-trans-stilbene |
| deoxyspergualin | $C_{17}H_{37}N_7O_3$ |
| sulindac | [(1Z)-5-fluoro-2-methyl-1-[4-(methylsulfinyl)benzylidene]-1H-indene-3-yl]acetic acid |

Figure 10 (cont'/Table 4)

| thalidomide | (R)-thalidomide   (S)-thalidomide<br>$C_{13}H_{10}N_2O_4$ |
| --- | --- |
| AGRO-100 | also known as AS1411 |
| CHS 828 | GMX 1778 (CAS 200484-11-3) |

Figure 11 (Table 5)

| Antibiotic class | Generic names |
|---|---|
| Aminoglycosides | Amikacin, Gentamicin, Kanamycin, Neomycin, Netilmicin, Tobramycin, Paromomycin, Spectinomycin |
| Ansamycins | Geldanamycin, Herbimycin, Rifaximin, Streptomycin |
| Carbacephem | Loracarbef |
| Carbapenems | Ertapenem, Doripenem, Imipenem/Cilastatin, Meropenem |
| Cephalosporins (First generation) | Cefadroxil, Cefazolin, Cefalotin or Cefalothin, Cefalexin |
| Cephalosporins (Second generation) | Cefaclor, Cefamandole, Cefoxitin, Cefprozil, Cefuroxime |
| Cephalosporins (Third generation) | Cefixime, Cefdinir, Cefditoren, Cefoperazone, Cefotaxime, Cefpodoxime, Ceftazidime, Ceftibuten, Ceftizoxime, Ceftriaxone |
| Cephalosporins (Fourth generation) | Cefepime |
| Cephalosporins (Fifth generation) | Ceftaroline fosamil, Ceftobiprole |
| Glycopeptides | Teicoplanin, Vancomycin, Telavancin |
| Lincosamides | Clindamycin, Lincomycin |
| Lipopeptide | Daptomycin |
| Macrolides | Azithromycin, Clarithromycin, Dirithromycin, Erythromycin, Roxithromycin, Troleandomycin, Telithromycin, Spiramycin |
| Monobactams | Aztreonam |
| Nitrofurans | Furazolidone, Nitrofurantoin |
| Oxazolidonones | Linezolid, Posizolid, Radezolid, Torezolid |
| Penicillins | Amoxicillin, Ampicillin, Aziocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin |

Figure 11 (cont' /Table 5)

| Penicillin combinations | Amoxicillin/clavulanate, Ampicillin/sulbactam, Piperacillin/tazobactam, Ticarcillin/clavulanate |
|---|---|
| Polypeptides | Bacitracin, Colistin, Polymyxin B |
| Quinolones/ Fluoroquinolone | Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin |
| Sulfonamides | Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic) |
| Tetracyclines | Demeclocycline, Doxycycline, Minocycline, Oxytetracycline, Tetracycline |

| Lysosthapin | is a Staphylococcus simulans metalloendopeptidase. It can function as an antimicrobial against Staphylococcus aureus. |
|---|---|

Figure 14 (cont')
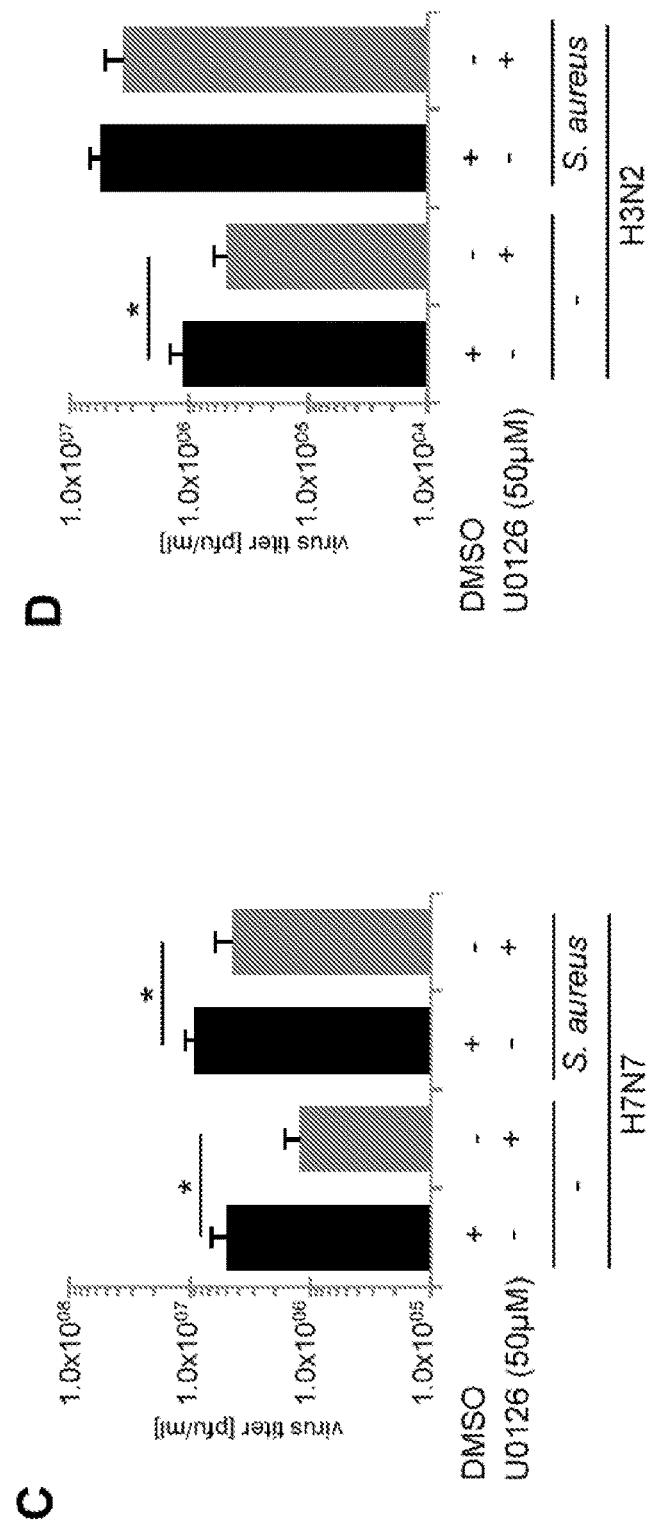

Figure 15 (cont')
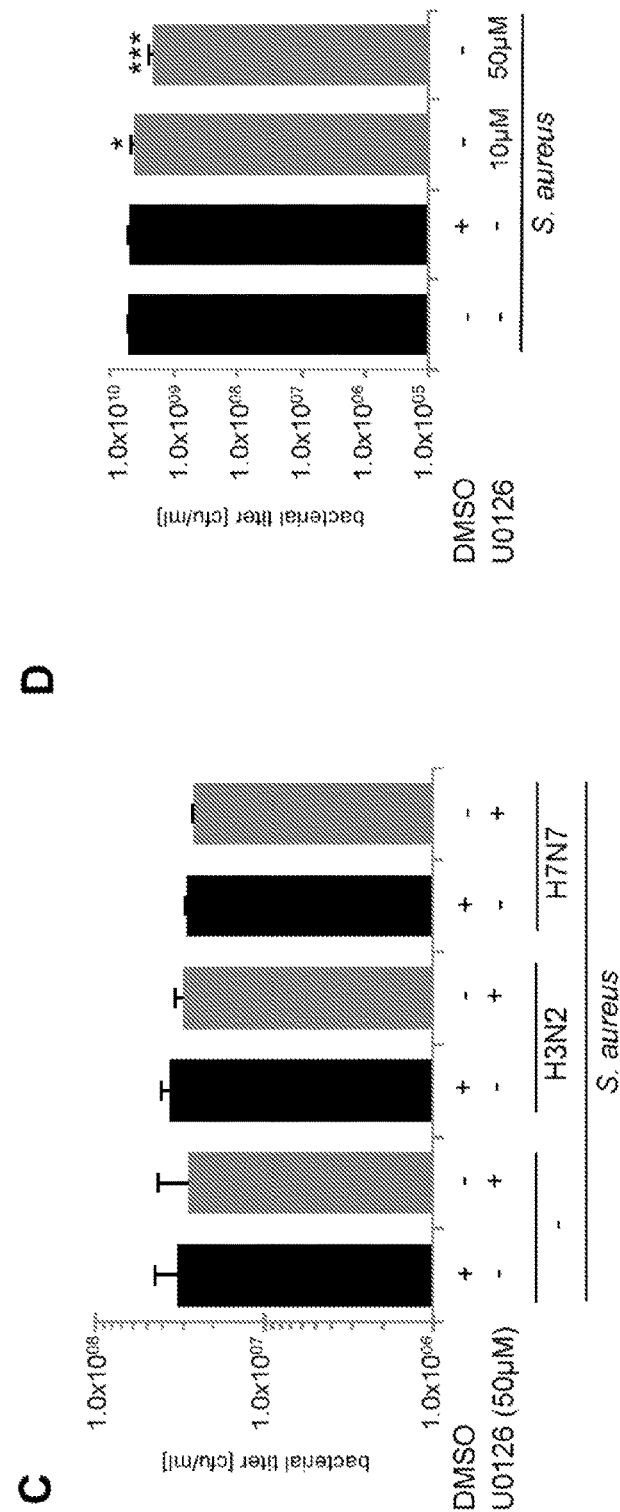

Figure 18 (cont')
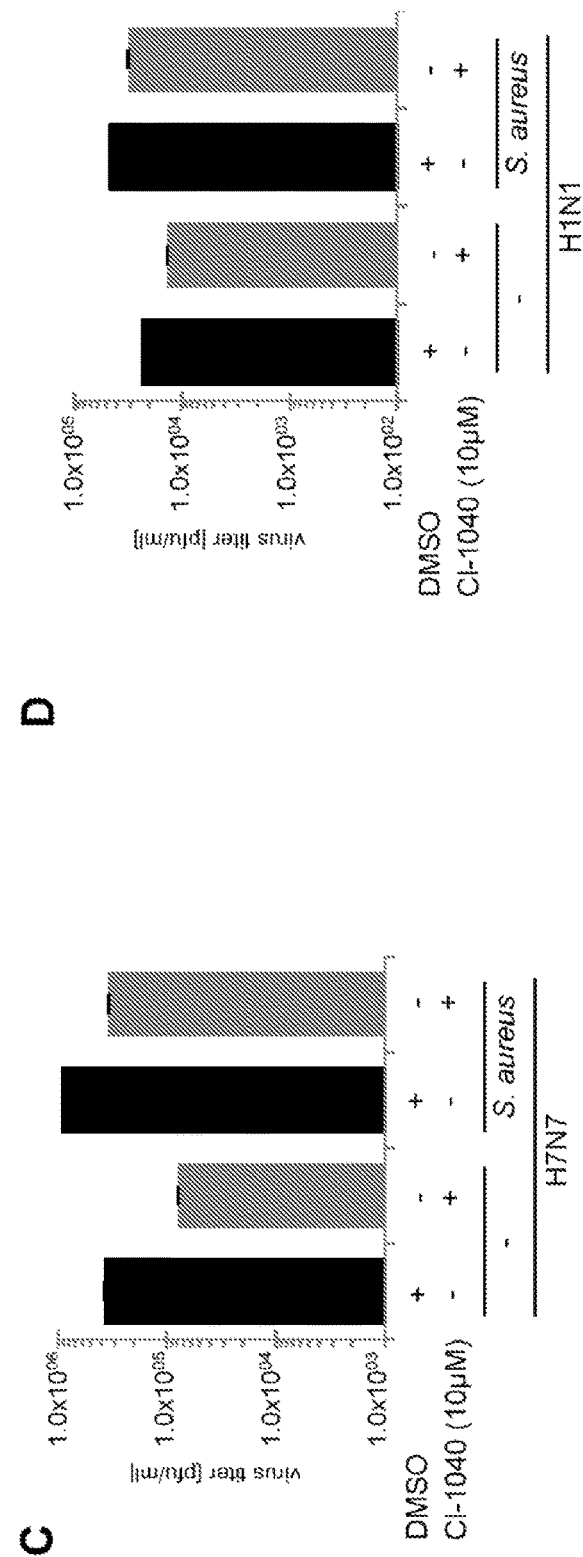

Figure 19
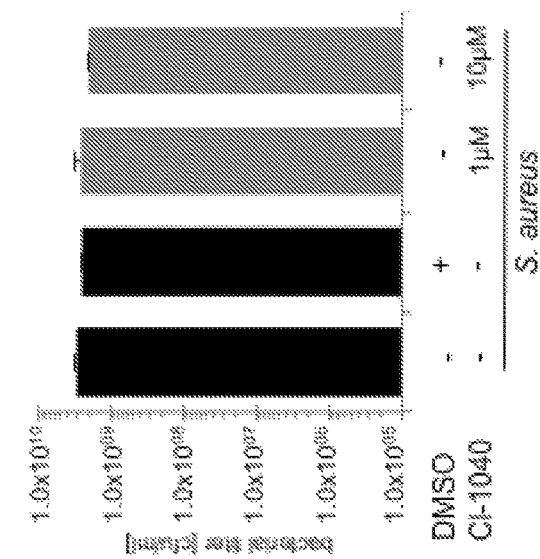
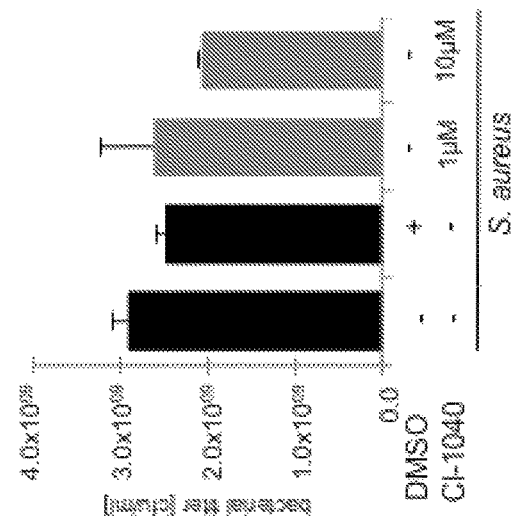

Figure 22 (cont')
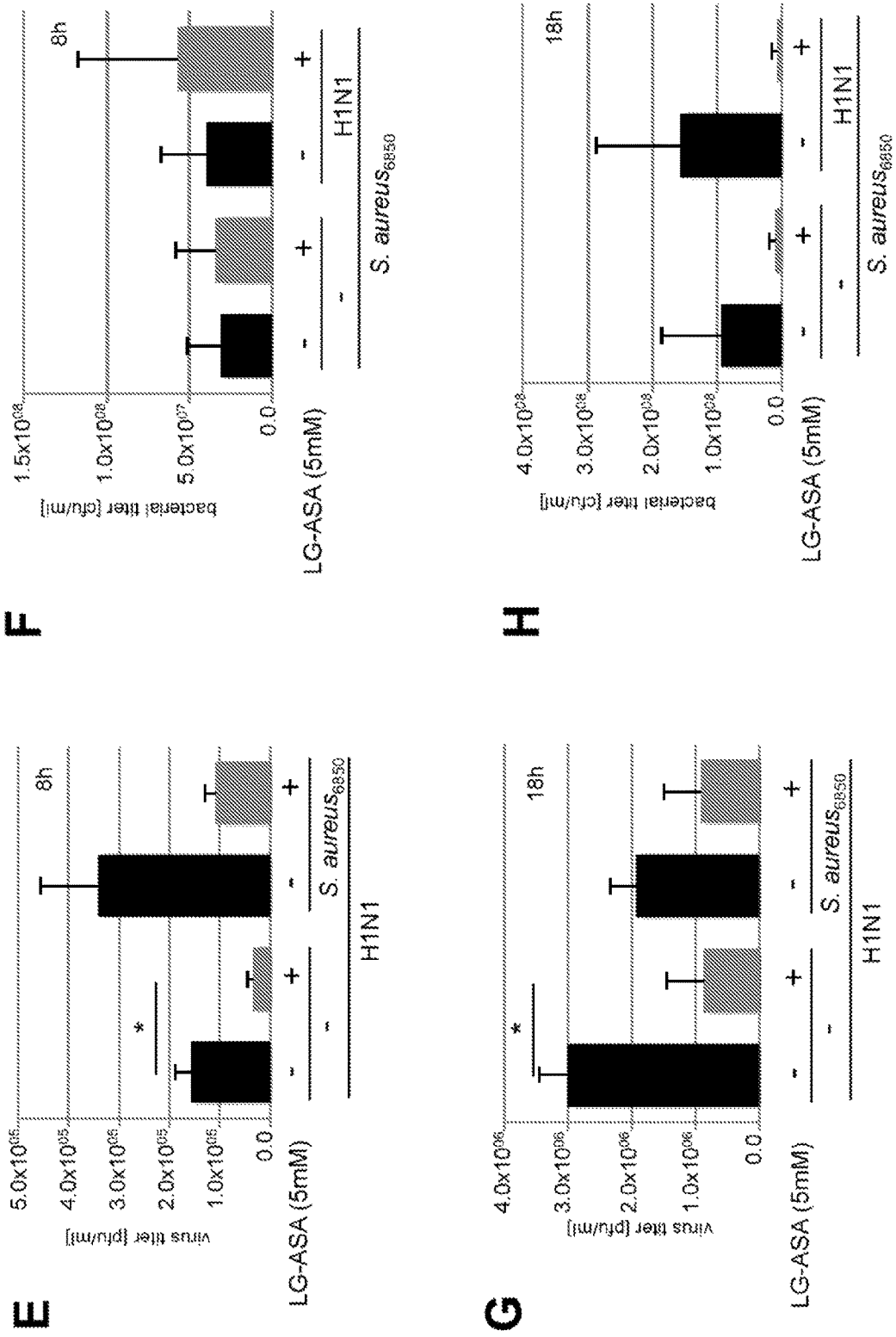

Figure 23 (cont')
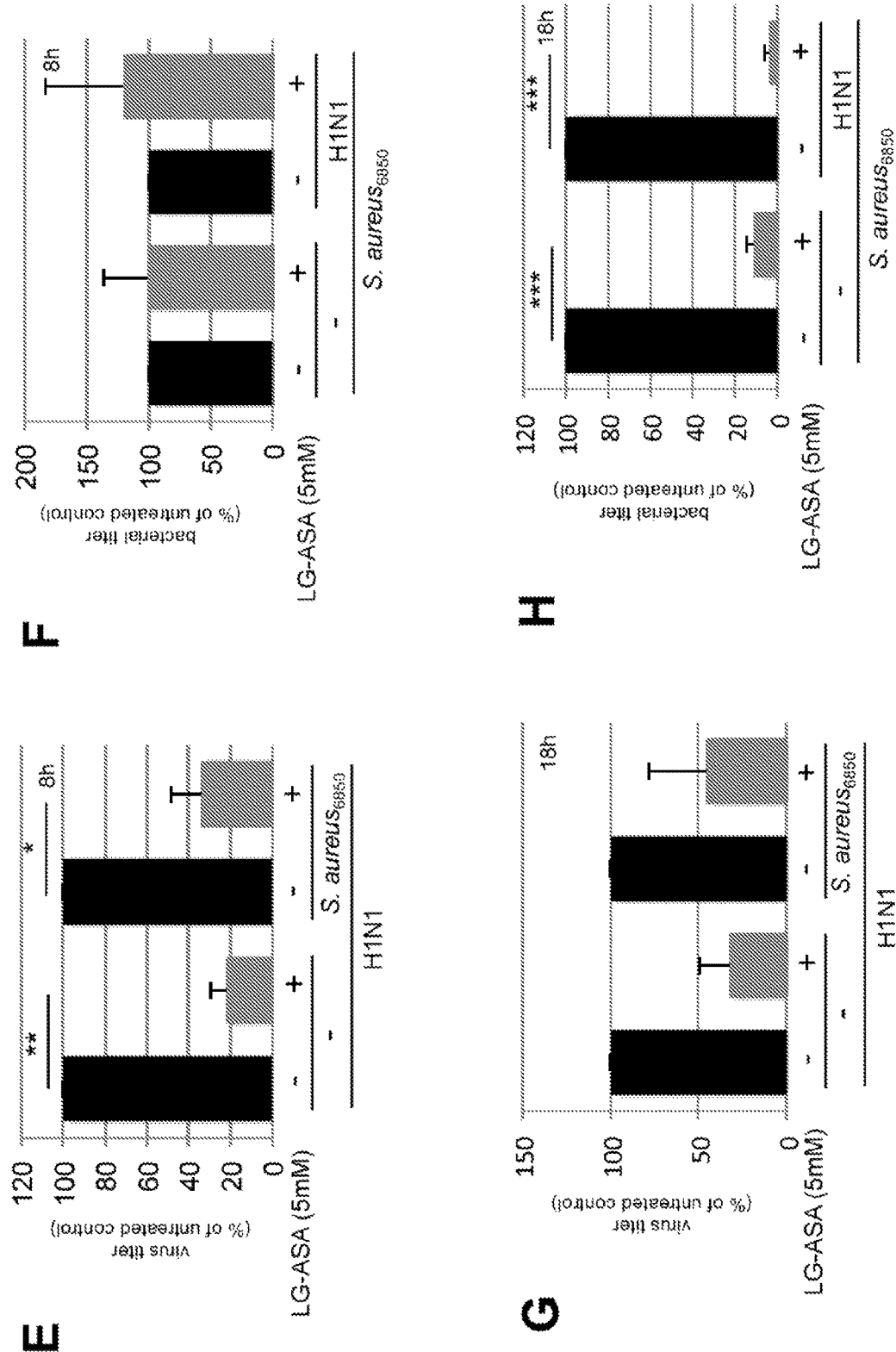

Figure 24 (cont')
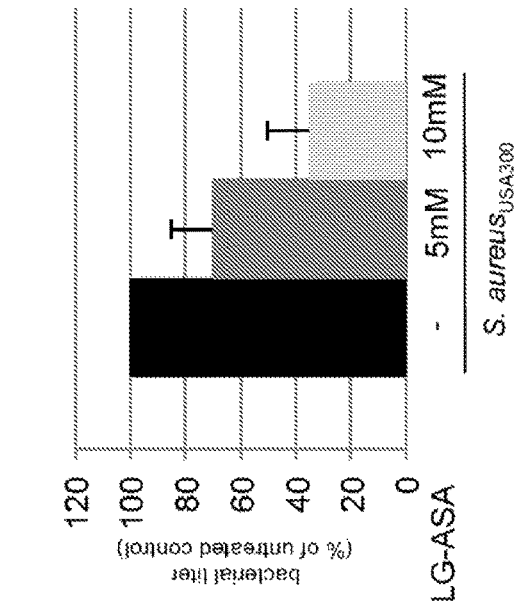
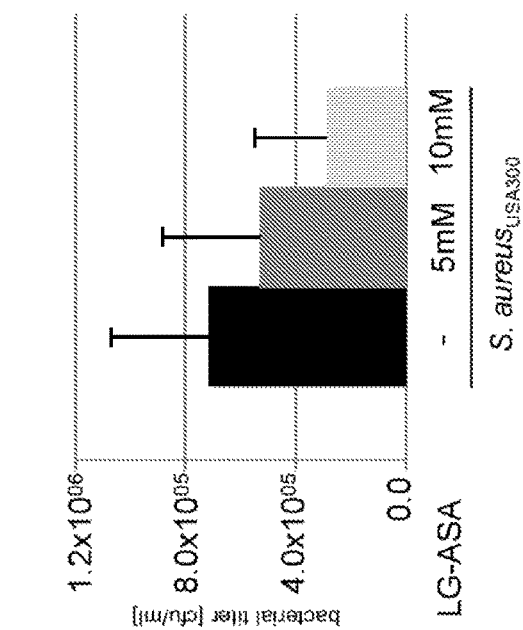

ANTI-INFECTIVE STRATEGY AGAINST INFLUENZA VIRUS AND S. AUREUS COINFECTIONS

FIELD OF THE INVENTION

The present invention relates to MEK inhibitor, p38 inhibitor and/or NFκB inhibitor for use in a method for the prophylaxis and/or treatment of a co-infection comprising a bacterial infection and an influenza virus infection or a bacterial infection alone. Also provided are compositions comprising such inhibitors for use in the prophylaxis and/or treatment of a co-infection comprising a bacterial infection and an influenza virus infection or a bacterial infection alone. In addition an in vitro test system, wherein the test system comprises cultured cells infected with an influenza virus and a bacterium or with a bacterium alone is provided.

BACKGROUND OF THE INVENTION

Influenza A viruses are the causative agents of severe respiratory diseases resulting in significant morbidity and mortality. Most of the fatal cases in the course of an influenza virus (IV) infection are actually a result of secondary pneumonia caused by different bacteria, such as Staphylococcus aureus (S. aureus), Streptococcus pneumoniae and Haemophilus influenzae (Morens et al., 2008, Chertow et al., 2013). The most striking problems of bacterial co-infection are the suddenly increased pathogenicity (Iwao et al., 2012, Paddock et al., 2012, Parker et al., 2012) and a limited arsenal of potent anti-infectives against the different pathogens. The high variability of influenza viruses and the continous emergence of new strains (Neumann et al., 2009, Taubenberger et al., 2010, Parry, 2013), specific characteristics of the bacterial strains (Grundmann et al., 2006, Moran et al., 2006, Gillet et al., 2007, Shilo et al., 2011), as well as the rapid resistance development of both, influenza viruses (Hayden et al., 1992, Bright et al., 2006, Pinto et al., 2006, De Clercq et al., 2007, Pinto et al, 2007) and bacteria (Grundmann et al., 2006, Moran et al., 2006, Shilo et al., 2011) against the available drugs/antibiotics are the major reasons for the poor treatment options. Moreover, it is incidental that treatment of coinfections with influenza viruses and bacteria is not possible with a single compound, so far. The current invention solves this problem in that it proposes a novel anti-infective strategy against IV and S. aureus co-infections by using single drugs. Furthermore, the present invention solves the problem of rapid resistance development of bacteria by providing drug that targets cellular factors rather than the bacterium itself.

SUMMARY OF THE INVENTION

The technical problem is solved by the embodiments reflected in the claims, described in the description, and illustrated in the Examples and Figures.

The above being said, the present invention relates to a MEK inhibitor, p38 inhibitor and/or NFκB inhibitor for use in a method for the prophylaxis and/or treatment of a co-infection comprising a bacterial infection and an influenza virus infection.

In addition the present invention relates to a MEK inhibitor, p38 inhibitor and/or NFκB inhibitor for use in a method for the prophylaxis and/or treatment of a bacterial infection.

Despite intensive research in the last century, IV still represent a severe threat to mankind. Seasonal outbreaks that are especially dangerous for the elderly and immunocompromised individuals are due to infections with influenza A or B viruses.

Within the last decades, there is an increasing incidence of methicillin-resistant S. aureus strains, causing problems especially in infants and children who were concomitantly infected with IV (Iverson et al., 2011, Thorburn et al., 2012). One major problem occurring upon bacterial co-infections is the sudden and highly increased pathogenicity, which is probably caused by accelerated cytokine expression, also resulting in tissue damage. Particularly, upon co-infection with Panton-Valentine leukocidin (PVL)-expressing S. aureus severe lung epithelium damage is observed, due to uncontrolled release of proteases after PVL-mediated neutrophil killing (Gillet et al., 2007, Niemann et al., 2012). Bacterial co-infections usually occur within the first six days of an IV infection, resulting in even more fulminant illness, pneumonia and higher mortality (Iverson et al., 2011, Chertow et al., 2013). However in some cases bacterial co-infection comes up, when virus-infection already seems to be cleared. For treatment of viral/bacterial co-infections only limited possibilities exist.

One promising antiviral strategy to fight influenza is based on the fact that IV, as intracellular pathogens, strongly depend on the cellular signaling machinery (Gong et al., 2009, Ludwig, 2009). IV acquired the ability to highjack cellular factors for its own purpose (Ludwig et al.,2003). Furthermore, IV are able to suppress the innate immune response of their hosts. Given these dependencies, cellular virus-supportive functions are most promising candidates for novel antiviral intervention (Ludwig et al., 2003, Ludwig, 2011, Planz, 2013). During the last years we and others identified the Raf/MEK/ERK mitogenic kinase cascade (Pleschka et al., 2001, Ludwig et al., 2004, Olschlager et al., 2004, Marjuki et al., 2006, Ludwig, 2009, Droebner et al., 2011), the IKK/NFκB module (Pleschka et al., 2001, Wurzer et al., 2004, Marjuki et al., 2006, Mazur et al., 2007, Ludwig et al., 2008, Dudek et al., 2010, Droebner et al., 2011, Ehrhardt et al., 2013, Haasbach et al., 2013), the p38-(Borgeling et al., 2014) and also the PI3K-signaling (Ehrhardt et al., 2006, Ehrhardt et al., 2007a, Ehrhardt et al., 2007b, Ehrhardt et al., 2009, Eierhoff et al., 2010) pathways as suitable targets for an anti-viral approach.

Targeting cellular rather than viral factors prevents the problem of resistance because the pathogen cannot replace the missing cellular function. For several cellular factors chemical compounds are available and although in an early stage, some of them have entered clinical testing or are even already licensed.

In contrast to IV replication, S. aureus division is host-cell independent. Novel antibacterial alternatives do not target essential gene products elaborated by the pathogen, but inhibit virulence factors during S. aureus infection without killing the bacterium or boosting host immunity (Park et al., 2012). Other strategies prevent colonization of S. aureus in the human host (Park et al., 2012). These compounds also exhibit a lower potential to induce resistance. Recently, there is accumulating evidence that S. aureus also uses cellular signaling for its own benefits during infection (Oviedo-Boyso et al., 2011), but such bacterial-supportive cellular factors have not yet been characterized as targets for antibacterial therapy in detail.

The present inventors surprisingly observed, that drugs against intracellular signaling factors, such as NFκB, MEK or p38 MAP kinase, that were previously shown to possess anti influenza activity, also exhibit anti S. aureus activity and reduces both viral- and bacterial titers in a coinfection scenario. Thus, these signaling inhibitors are most promising candidates for the treatment of IV or *S. aureus* infections alone, but, most importantly also against severe influenza accompanied with bacterial coinfection.

In one embodiment, the MEK inhibitor, p38 inhibitor and/or NFκB inhibitor is/are for use in the methods for the prophylaxis and/or treatment of a co-infection or bacterial infection of the present invention, wherein the the bacterial infection is mediated by a bacterium selected from the group consisting of *Staphylococcaceae, Streptococcaceae, Legionellaceae, Pseudomonadaceae, Chlamydiaceae, Mycoplasmataceae, Enterobacteriaceae, Pseudomonadales* and/or *Pasteurellaceae*.

In another embodiment the MEK inhibitor, p38 inhibitor and/or NFκB inhibitor is/are for use in the methods for the prophylaxis and/or treatment of a co-infection of the present invention, wherein the influenza virus infection is mediated by influenza A virus or influenza B virus, preferably the influenza A virus is H1N1, H2N2, H3N2, H6N1, H7N7, H7N9, H9N2 H10N7, H10N8 or H5N1. In one embodiment, the influenza A virus is H1N1. In other embodiments, the influenza A virus is H3N2, H5N1 and H7N9. In additional embodiments, the influenza A virus is H3N2, H5N1, H1N1 and H7N9.

In a further embodiment the MEK inhibitor, p38 inhibitor and/or NFκB inhibitor is/are for use in the methods for the prophylaxis and/or treatment of a co-infection or bacterial infection of the present invention, wherein the MEK inhibitor is selected from the group consisting of U0126, PLX-4032, AZD6244, AZD8330, AS-703026, GSK-1120212, RDEA-119, RO-5126766, RO-4987655, CI-1040, PD-0325901, GDC-0973, TAK-733, PD98059, ARRY-438162, PF-3644022 and PD184352, preferably AZD8330, GSK-1120212, U0126, GDC-0973, CI-1040, PD0325901, ARRY-438162, PF-3644022 and AZD6244, most preferably U0126, GDC-0973, CI-1040, AZD8330 and GSK-1120212.

In another embodiment the MEK inhibitor, p38 inhibitor and/or NFκB inhibitor is/are for use in the methods for the prophylaxis and/or treatment of a co-infection or bacterial infection of the present invention, wherein the p38 inhibitor is selected from the group consisting of SB202190, LY2228820, CAY10571, SB 203580, Tie2 Kinase Inhibitor, 2-(4-Chlorophenyl)-4-(fluorophenyl)-5-pyridin-4-yl-1,2-dihydropyrazol-3-one, CGH 2466, SB220025, Antibiotic LL Z1640-2, TAK 715, SB202190 hydrochloride, SKF 86002, AMG548, CMPD-1, EO1428, JX 401, ML 3403, RWJ 67657, SB 202190, SB 203580, SB 203580 hydrochloride, SB 239063, SCIO 469, SX 011, TAK 715, Parrapimod, Losmapimad (GW856553), Dilrnapimod (SB681323), VX 702, VX 745, Doramapimod (BIRB 796), BMS-582949, ARRY-797, PH797804 preferably VX-702, SB202190, Pamapimod, Iosmapimod (GW856553), Dilmapimod (SB681323), Doramapimod (BIRB 796), BMS-582949, ARRY-797, PH797804 and SCIO-469.

In another embodiment the MEK inhibitor, p38 inhibitor and/or NFκB inhibitor is/are for use in the methods for the prophylaxis and/or treatment of a co-infection or bacterial infection of the present invention, wherein the NFκB inhibitor is selected from the group consisting of LASAG (also called LG-ASA), SC75741, MG 132, TPCA-1, PCTC, IMD 0354, Luteolin, Caffeic acid phenethyl ester, Cardamonin, PF 184, IKK 16, SC 514, Withaferin A, Arctigenin, Bay 11-7085, PSI, PR 39, Ro 106-9920, Bay 11-7821, ML-130, Celastrol, Tanshinone IIA, HU 211, Gliotoxin, CID 2858522, Honokiol, Andrographolide, 10Z-Hymenialdisine, ACHP, Pristimerin, Sulfasalazine, ML 120B dihydrochloride, Amlexanox, 9-Methylstreptimidone, N-Stearoyl phytosphingosine, 2-(1,8-naphthyridin-2-yl)-Phenol, 5-Aminosalicylic acid, BAY 11-7085, Ethyl 3,4-Dihydroxycinnamate, Helanalin, NF-κB Activation Inhibitor II, JSH-23, Glucocorticoid Receptor Modulator, CpdA, PPM-18, aspirin (ASA), Pyrrolidinedithiocarbamic acid ammonium salt, (R)-MG132, SC75741 Rocaglamide, Sodium salicylate, QNZ, PS-1145, CAY10512, bortezomib, salsalate, resveratrol, deoxyspergualin, sulindac, thalidomide, AGRO-100, CHS 828 and/or Curcumin preferably, bortezomib, curcumin, aspirin (ASA), salsalate, resveratrol, sodium salicylate, LASAG (also called LG-ASA), deoxyspergualin, sulindac, thalidomide, AGRO-100, CHS 828 even more preferably SC75741, ASA and LASAG (also called LG-ASA) and most preferably LASAG (also called LG-ASA).

In additional embodiments, the MEK inhibitor, p38 inhibitor and/or NFκB inhibitor is/are for use in the methods for the prophylaxis and/or treatment of a co-infection or bacterial infection of the present invention, wherein the MEK inhibitor is combined with another MEK inhibitor, the p38 inhibitor and/or the NFκB inhibitor; the p38 inhibitor is combined with another p38 inhibitor, the MEK inhibitor and/or the NFκB inhibitor or the NFκB inhibitor is combined with another NFκB inhibitor, the p38 inhibitor and/or the MEK inhibitor.

In further embodiments, the MEK inhibitor, p38 inhibitor and/or NFκB inhibitor is/are for use in the methods for the prophylaxis and/or treatment of a co-infection of the present invention, wherein the MEK inhibitor, the p38 inhibitor and/or the NFκB inhibitor are combined with one or more inhibitors targeting the influenza virus and/or the bacterium. In one embodiment, the MEK inhibitor, the p38 inhibitor and/or the NFκB inhibitor is/are administered contemporaneously, previously or subsequently to the one or more inhibitors targeting the influenza virus and/or the bacterium. As such the MEK inhibitor, p38 inhibitor and/or NFκB inhibitor can be combined with 1, 2, 3, 4, 5, 6, 7, or 8 inhibitors targeting the influenza virus. Similraly, the MEK inhibitor, p38 inhibitor and/or NFκB inhibitor can be combined with 1, 2, 3, 4, 5, 6, 7, or 8 inhibitors targeting the bacterium.

In one embodiment, the one or more inhibitors targeting the influenza virus is a neuraminidase inhibitor, preferably oseltamivir phosphate, zanamivir, oseltamivir or peramivir.

In another embodiment, the one or more inhibitors targeting the influenza virus is a compound targeting an ion channel protein (M2), preferably amantadine and/or rimantadine. In further embodiments, the one or more inhibitors targeting the influenza virus is a compound targeting polymerase or endonuclease activity via interfering with a component of the viral polymerase complex, PB1, PB2, PA or NP, preferably NP blocker Nucleozin or polymerase inhibitor T-705.

In further embodiments, the MEK inhibitor, p38 inhibitor and/or NFκB inhibitor is/are for use in the methods for the prophylaxis and/or treatment of a bacterial infection of the present invention, wherein the MEK inhibitor, the p38 inhibitor and/or the NFκB inhibitor are combined with one or more inhibitors targeting the bacterium.

In another embodiment, the MEK inhibitor, p38 inhibitor and/or NFκB inhibitor is/are for use in the methods for the prophylaxis and/or treatment of a co-infection or bacterial infection of the present invention, the one or more inhibitor targeting the bacterium is an antibiotic, preferably Gentamicin, Rifampicin, Lysosthaphin, Erythromycin, Levofloxacin Vancomycin, Teicoplanin, Penicillin and Oxacillin.

In additional embodiments, the MEK inhibitor, p38 inhibitor and/or NFκB inhibitor is/are for use in the methods for the prophylaxis and/or treatment of a co-infection or bacterial infection of the present invention is in a subject, preferably a vertebrate.

Also provided for by the present invention is a composition, comprising a MEK inhibitor, a p38 inhibitor and/or a NFκB inhibitor for use in a method for the prophylaxis and/or treatment of a co-infection comprising a bacterial infection and an influenza virus infection. Preferably, the composition further comprises a carrier.

The present invention also relates to a composition, comprising a MEK inhibitor, a p38 inhibitor and/or a NFκB inhibitor for use in a method for the prophylaxis and/or treatment of a bacterial infection. Preferably, the composition further comprises a carrier.

Also provided for by the present invention is a composition, comprising a MEK inhibitor, a p38 inhibitor and/or a NFκB inhibitor and one or more inhibitors targeting the influenza virus and/or the bacterium for use in a method for the prophylaxis and/or treatment of a co-infection comprising a bacterial infection and an influenza virus infection. Preferably, the composition further comprises a carrier.

The present invention also relates to a composition, comprising a MEK inhibitor, a p38 inhibitor and/or a NFκB inhibitor and one or more inhibitors targeting the bacterium for use in a method for the prophylaxis and/or treatment of a a bacterial infection. Preferably, the composition further comprises a carrier.

In further embodiments, the MEK inhibitor, p38 inhibitor and/or NFκB inhibitor is/are for use in the methods for the prophylaxis and/or treatment of a co-infection of the present invention, wherein the MEK inhibitor, the p38 inhibitor and/or the NFκB inhibitor reduces both the viral and bacterial infection, when contacting it/them with an in vitro test system, wherein the test system comprises cultured cells infected with
a) an influenza virus and
b) a bacterium
when compared to the in vitro test system before the contacting.

In one embodiment, the reduction of the viral infection is a reduction in plaque forming units (pfu)/ml and the reduction in the bacterial infection is a reduction in colony forming units (CFU)/ml.

In another embodiment, the MEK inhibitor, p38 inhibitor and/or NFκB inhibitor is/are for use in the methods for the prophylaxis and/or treatment of a bacterial infection of the present invention, wherein the MEK inhibitor, the p38 inhibitor and/or the NFκB inhibitor reduces the bacterial infection, when contacting it/them with an in vitro test system, wherein the test system comprises cultured cells infected with a bacterium, when compared to the in vitro test system before the contacting.

The present invention also relates to an in vitro test system, wherein the test system comprises
cultured cells infected with
a) an influenza virus and
b) a bacterium.

The invention also provides for the use of the in vitro test system of of the present invention for the determination of inhibitors effective in reducing a coinfection comprising a bacterial infection and an influenza virus infection. In one embodiment, the reduction of the viral infection is a reduction in plaque forming units (pfu)/ml and the reduction in the bacterial infection is a reduction in colony forming units (CFU)/ml.

In addition the present invention relates to a method for detecting molecules effective in the prophylaxis and/or treatment of a co-infection comprising a bacterial infection and an influenza virus infection comprising contacting the in vitro test system of the present invention with a compound of interest, wherein the compound of interest reduces both the viral and bacterial infection, compared to the in vitro test system before the contacting.

The present invention also provides for an in vitro test system, wherein the in vitro test system comprises cultured cells infected with a bacterium.

The present invention, in addition, relates to a use of the in vitro test system of the present invention for the determination of inhibitors effective in reducing a bacterial infection.

Furthermore, the present invention relates to the use of the in vitro test systems of the present invention for the examination of innate host cell responses, which optionally includes examination of the level of signal transduction, resulting cytokine and chemokine expression, induction of apoptosis and necrosis and/or redox hemostasis regulating health and disease.

Also provided for by the present invention is a method for detecting molecules effective in the prophylaxis and/or treatment a bacterial infection comprising contacting the in vitro test system of the present invention with a compound of interest, wherein the compound of interest reduces the bacterial infection, compared to the in vitro test system before the contacting.

The present invention furthermore relates to a cultured cell infected with an influenza virus and a bacterium.

Also provided for is a cultured cell infected with a bacterium.

IV titers are depicted as plaque forming units (pfu)/ml (A, C) and S. aureus titers are depicted as colonie forming units (CFU)/ml (B,D). Data represent the means±SD of three independent experiments with two biological samples. Statistical significance was evaluated by a two-tailed two sample t-test (*p<0.05;p<0.01;*p<0.001). (E) S. aureus in presence of 50 µM U0126 results in reduced bacterial titers 18 hrs upon incubation in comparison to DMSO treated bacteria. A defined amount of S. aureus 6850 suspension culture was diluted in DMEM/INV supplemented with 50 µM U0126 or DMSO and incubated at 37° C. for 18 hrs. Bacteria were diluted and determined by serial dilution on agar plates. Data represent the means±SD of three independent experiments with two biological samples. Statistical significance was evaluated by a two-tailed two sample t-test (*p<0.05; p<0.01;*p<0.001).

Figure 3:
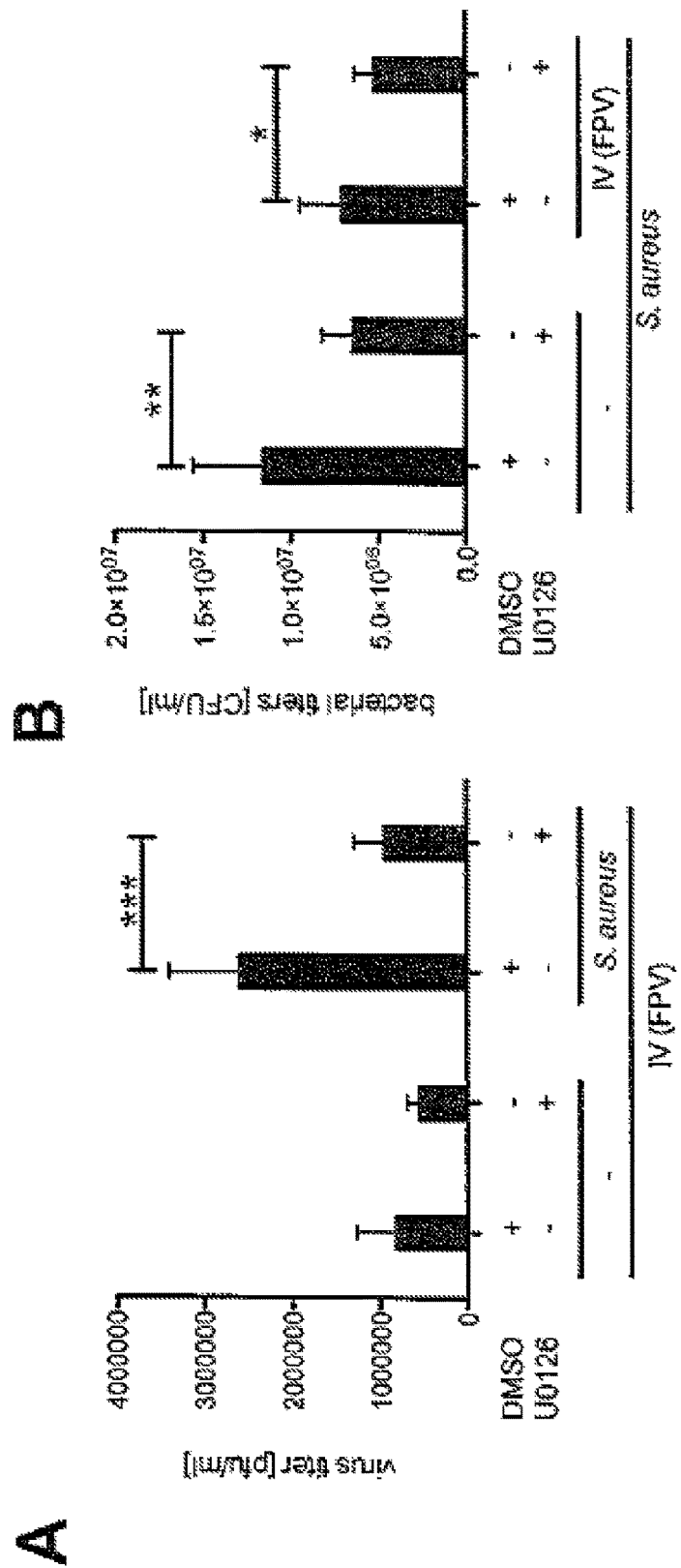

FIG. 3: The MEK inhibitor U0126 reduces IV titers (A/FPV/Bratislava/79) and S. aureus load, even in a co-infection situation. Human lung epithelial cells were seeded in 6-well plates ($8 \times 10^5$ cells/well) in 2 ml DMEM [10% FCS]. 16-20 hrs after seeding, cells were rinsed and incubated with PBS/BA [0.2% bovine serum albumin (BSA), 1 mM $MgCl_2$, 0.9 mM $CaCl_2$, 100 U/ml penicillin , 0.1 mg/ml streptomycin] (500 µl per 6 well) or PBS/BA containing the Influenza virus A/FPV/Bratislava/79 at a multiplicity of infection (MOI=0.001) at 37° C. After 30 min incubation, the virus dilution was aspirated, cells were rinsed with PBS and supplemented with Invasion medium DMEM/INV [1% human serum albumin, 25 nmol/l HEPES] (2 ml per 6 well) with or without S. aureus 6850 (MOI=0.5) in presence of 50 µM U0126 or DMSO (solvent control). 3 hrs post bacterial infection cells were treated with antibiotics to remove extracellular bacteria. Therefore cells were rinsed with PBS and subsequently incubated with DMEM/INVantibiotics [2 µg/ml lysostaphin (Sigma)] (1 ml per 6 well) for 20 min at 37° C. After an additional wash with PBS cells were supplemented with DMEM/INV containing 50 µM U0126 or DMSO. After an incubation period of further 14 hrs at 37° C. IV titers and intracellular bacteria were determined as described in (Hrincius et al., 2010; Tuchscherr et al., 2011). IV titers are depicted as plaque forming units (pfu)/ml (A, C) and S. aureus titers are depicted as colonie forming units (CFU)/ml (B, D). Data represent the means±SD of two independent experiments with two biological samples. Statistical significance was evaluated by a two-tailed two sample t-test (*p<0.05;p<0.01;*p<0.001).

Figure 4:
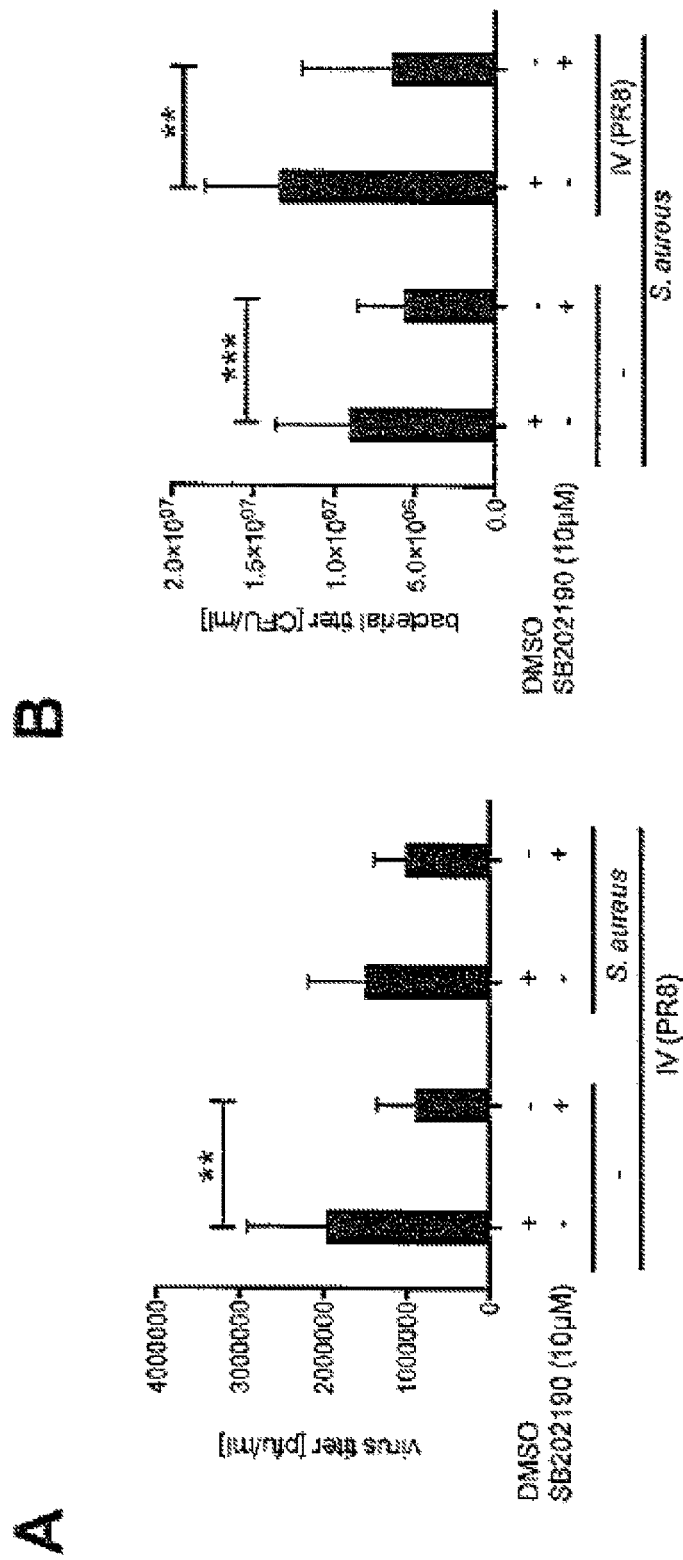

FIG. 4: The p38 inhibitor SB202190 reduces IV titers and S. aureus load, even in a co-infection situation. Human lung epithelial cells were seeded in 6-well plates ($8 \times 10^5$ cells/well) in 2 ml DMEM [10% FCS]. 16-20 hrs after seeding, cells were rinsed and incubated with PBS/BA [0.2% bovine serum albumin (BSA), 1 mM $MgCl_2$, 0.9 mM $CaCl_2$, 100 U/ml penicillin , 0.1 mg/ml streptomycin] (500 µl per 6 well) or PBS/BA containing the Influenza virus A/Puerto Rico/8/34 at a multiplicity of infection (MOI=0.1) at 37° C. After 30 min incubation, the virus dilution was aspirated, cells were rinsed with PBS and supplemented with Invasion medium DMEM/INV [1% human serum albumin, 25 nmol/l HEPES] (2 ml per 6 well) with or without S. aureus 6850 (MOI=0.5) in presence of 10 µM SB202190 or DMSO (solvent control). 3 hrs post bacterial infection cells were treated wich antibiotics to remove extracellular bacteria. Therefore cells were rinsed with PBS and subsequently incubated with DMEM/INVantibiotics [2 µg/ml lysostaphin (Sigma)] (1 ml per 6 well) for 20 min at 37° C. After an additional wash with PBS cells were supplemented with DMEM/INV containing 10 µM SB202190 or DMSO and 0.333 µg/ml Trypsin (Invitrogen). After an incubation period of further 14 hrs at 37° C. IV titers and intracellular bacteria were determined as described in (Hrincius et al., 2010; Tuchscherr et al., 2011). IV titers are depicted as plaque forming units (pfu)/ml (A, C) and S. aureus titers are depicted as colonie forming units (CFU)/ml (B, D). Data represent the means±SD of three independent experiments with two biological samples. Statistical significance was evaluated by a two-tailed two sample t-test (*p<0.05; p<0.01;*p<0.001).

Figure 5:
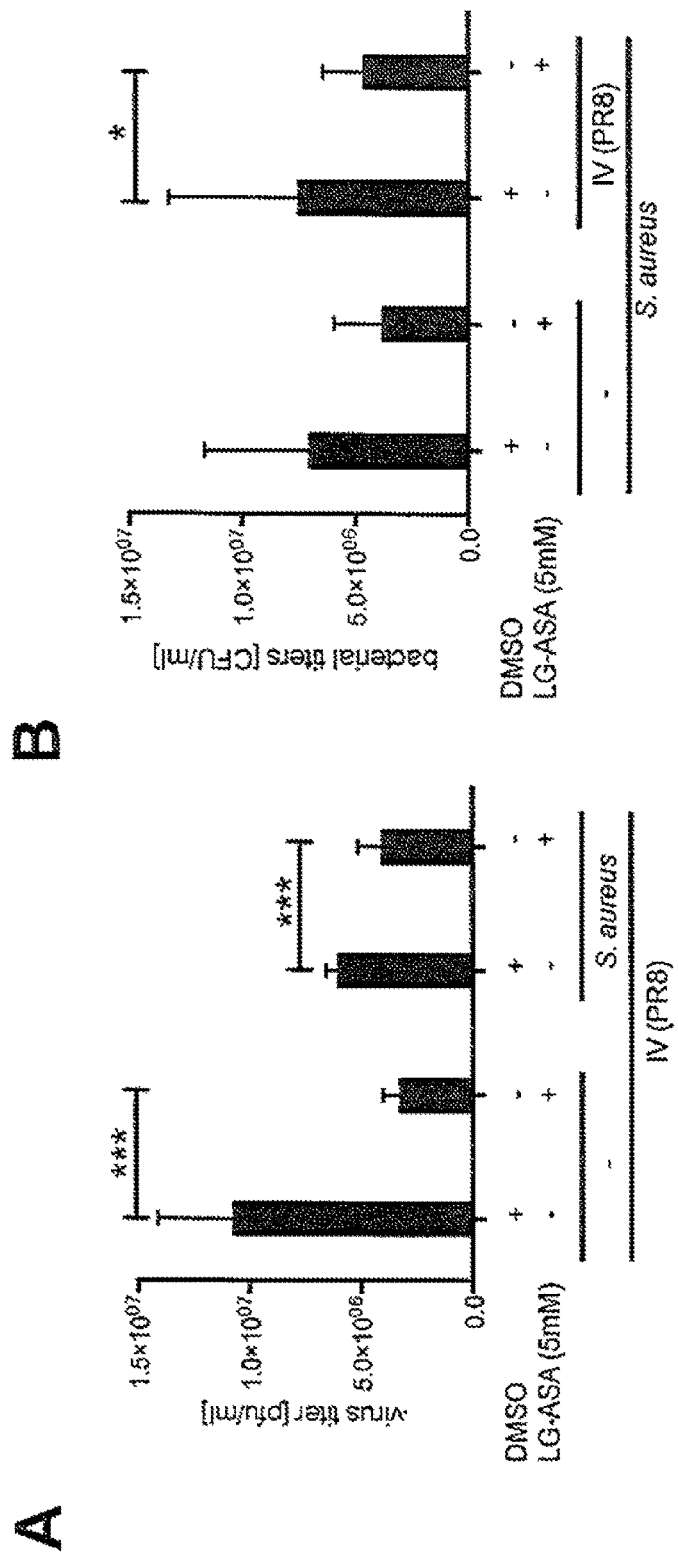

FIG. 5: The NF-kappaB (NFKB) inhibitor LG-ASA reduces IV titers and S. aureus load, even in a co-infection situation. Human lung epithelial cells were seeded in 6-well plates ($8 \times 10^5$ cells/well) in 2 ml DMEM [10% FCS]. 16-20 hrs after seeding, cells were rinsed and incubated with PBS/BA [0.2% bovine serum albumin (BSA), 1 mM $MgCl_2$, 0.9 mM $CaCl_2$, 100 U/ml penicillin , 0.1 mg/ml streptomycin] (500 µl per 6 well) or PBS/BA containing the influenza virus A/Puerto Rico/8/34 at a muitiplicity of infection (MOI=0.1) at 37° C. After 30 min incubation, the virus dilution was aspirated, cells were rinsed with PBS and supplemented with invasion medium DMEM/INV [1% human serum albumin, 25 nmol/l HEPES] (2 ml per 6 well) with or without S. aureus 6850 (MOI=0.5) in presence of 5 mM LG-ASA. Water was used as solvent control. 3 hrs post bacterial infection cells were treated with antibiotics to remove extracellular bacteria. Therefore cells were rinsed with PBS and subsequently incubated with DM EM/INVantibiotics [10% FBS, 2 µg/ml lysostaphin (Sigma)] (1 ml per 6 well) for 20 min at 37° C. After an additional wash with PBS cells were supplemented with DMEM/INV containing 5 mM LG-ASA or water and 0.333 µg/ml Trypsin (Invitrogen). After an incubation period of further 14 hrs at 37° C. IV titers and intracellular bacteria were determined as described in (Hrincius et al., 2010, Tuchscherr et al., 2011). IV titers are depicted as plaque forming units (pfu)/ml (A, C) and S. aureus titers are depicted as colonie forming units (CFU)/ml (B, D). Data represent the means±SD of two independent experiments (virus titer) and three independent experiments (bacterial titer) with two biological samples. Statistical significance was evaluated by a two-tailed two sample t-test (*p<0.05;p<0.01;*p<0.001).

Figure 6:
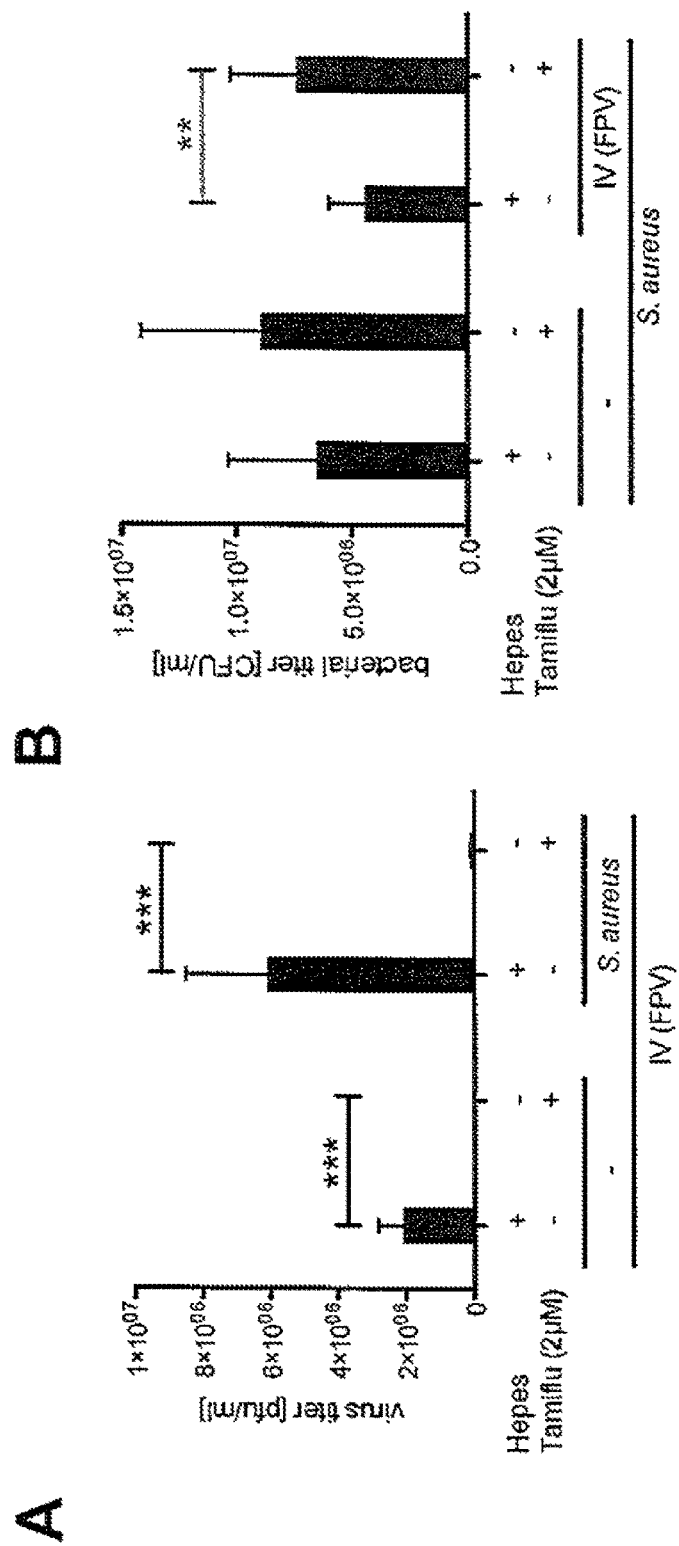

FIG. 6: The viral neuraminidase inhibitor tamiflu reduces IV replication but enhances S. aureus load. Human lung epithelial cells were seeded in 6-well plates ($8 \times 10^5$ cells/well) in 2 ml DMEM [10% FCS]. 16-20 hrs after seeding, cells were rinsed and incubated with PBS/BA [0.2% bovine serum albumin (BSA), 1 mM $MgCl_2$, 0.9 mM $CaCl_2$,100 U/ml penicillin , 0.1 mg/ml streptomycin] (500 µl per 6 well) or PBS/BA containing the Influenza virus A/FPV/Bratislava/79 at a multiplicity of infection (MOI=0.001) at 37° C. After 30 min incubation, the virus dilution was aspirated, cells were rinsed with PBS and supplemented with invasion medium DMEM/INV [1% human serum albumin, 25 nmol/l HEPES] (2 ml per 6 well) with or without S. aureus 6850 (MOI=0.5) in presence of 2 µM tamiflu or Hepes (solvent control). 3 hrs post bacterial infection cells were treated with antibiotics to remove extracellular bacteria. Therefore cells were rinsed with PBS and subsequently incubated with DMEM/INVantibiotics (2 µg/ml lysostaphin (Sigma)] (1 ml per 6 well) for 20 min at 37° C. After an additional wash with PBS cells were supplemented wich DMEM/INV containing 2 µM tamiflu or Hepes. After an incubation period of further 14 hrs at 37° C. IV titers and intracellular bacteria were determined as described in (Hrincius et al., 2010; Tuchscherr et al., 2011).

FIG. 7: Titers of intracellular S. aureus 6850 are reduced upon LG-ASA treatment. Human lung epithelial cells (A549) were infected with 0.5MOI S. aureus 6850 DMEM/INV [1% human serum albumin, 25 nmol/l HEPES] for 3 h in presence (A, C) and absence (B, D) of the indicated amounts of LG-ASA. Three hours post infection an antibiotic wash was included using DMEM/INVantibiotics [2 μg/ml lysostaphin (Sigma)] to remove non-internalized bacteria and subsequently cells were supplemented with DMEM/INV containing the indicated amounts of LG-ASA. Cell morphology was monitored by light microscopy (A, B) and amounts of internalized bacteria were determined by serial dilution on agar plates 18 hours post infection (C, D).

FIG. 8: Table 2: p38 inhibitors.

FIG. 9: Table 3: NFκB inhibitors.

FIG. 10: Table 4: NFκB inhibitors.

FIG. 11: Table 5: antibiotics.

Figure 12:
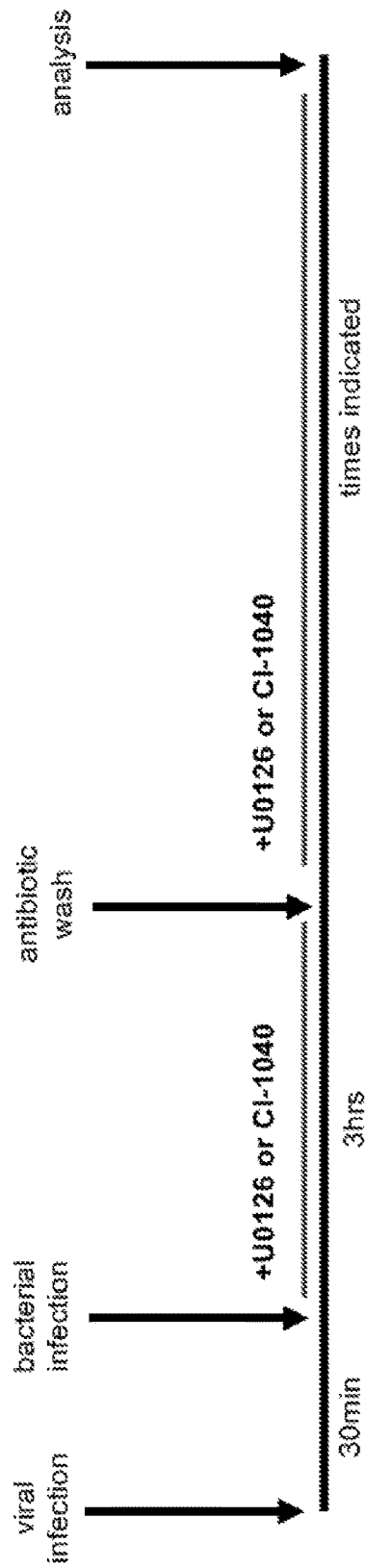

FIG. 12: Time scale of the co-infection procedure in vitro. Human lung epithelial cells (A549) were infected with influenza A virus (IAV) for 30 min at a multiplicity of infection (MOI) indicated, dissolved in PBS/BA [0.2% bovine serum albumin, 1 mM $MgCl_2$, 0.9 mM $CaCl_2$, 100 U/ml penicillin, 0.1 mg/ml streptomycin] at 37° C. After 30 min incubation, the virus dilution was aspirated, cells were rinsed with PBS. Afterwards bacterial infection with Staphylococcus aureus 6850 (S. aureus) was performed or cells were mock-treated. Therefore cells were supplemented with invasion medium DMEM/INV [1% human serum albumin, 25 nmol/l HEPES] with or without S. aureus in addition to the indicated amounts of inhibitor (U0126 or CI-1040 ) or solvent control. 3 hrs post bacterial infection an antibiotic wash [DMEM, 10% FBS, 2 μg/ml Lysostaphin or 100 μg/ml Gentamicin, 20 min] was introduced to remove non-internalized bacteria. After an additional PBS wash, cells were supplemented with infection medium DMEM (0.2% BA, 1 mM $MgCl_2$, 0.9 mM $CaCl_2$, 100 U/ml penicillin, 0.1 mg/ml streptomycin) in presence or absence of the inhibitor and were incubated up to 18 hrs post viral infection at 37° C.

Figure 13:
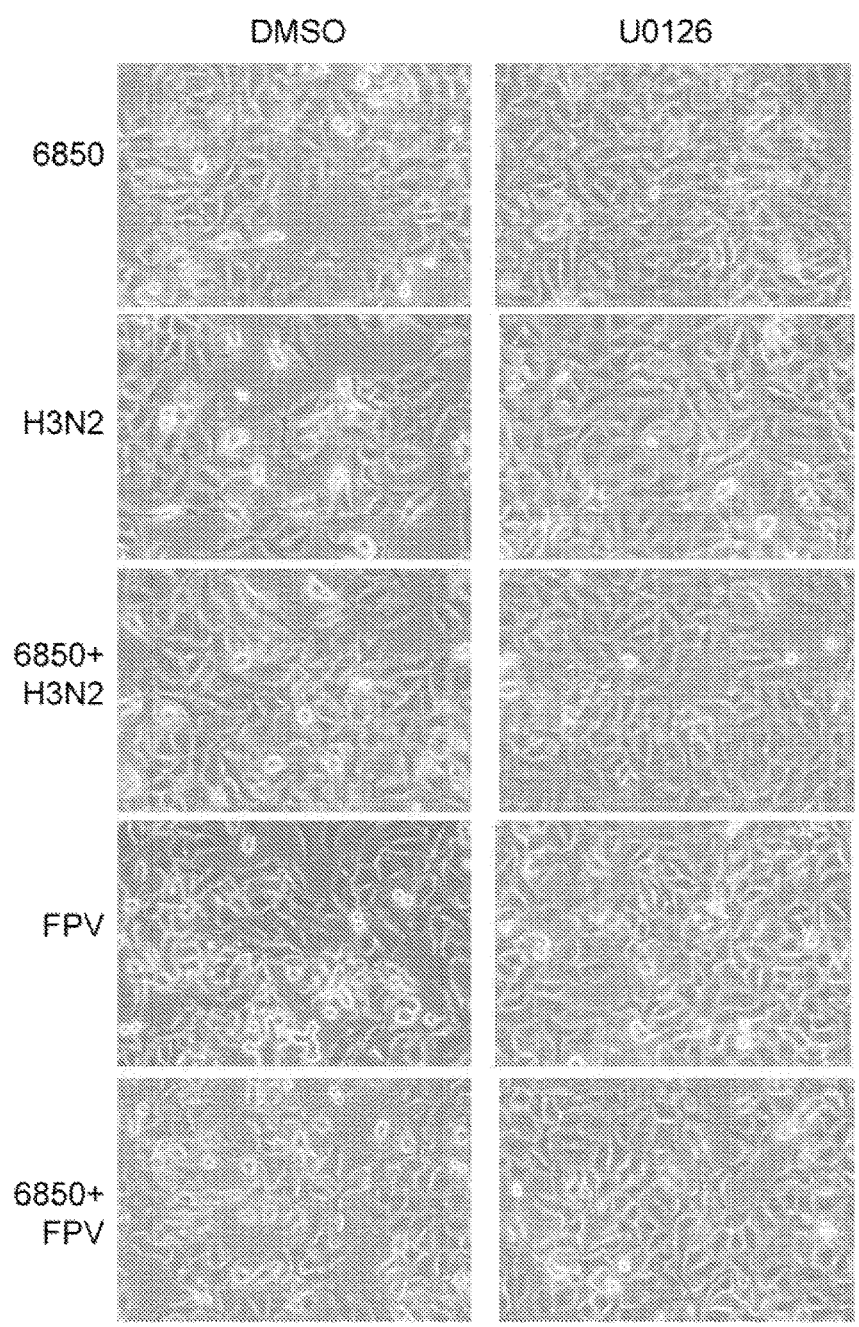

FIG. 13: Inhibition of the MEK/ERK signaling results in enhanced cell survival after singular and co-infection.

Human lung epithelial cells (A549) were infected with the avian influenza virus strain A/FPV/Bratislava/79 (H7N7) (FPV) or the human influenza virus strain A/Wisconsin/67/2005 (H3N2) at a multiplicity of infection (MOI=0.001) (H7N7) or (MOI=0.5) (H3N2) at 37° C. After 30 min the virus dilution was removed, cells were rinsed with PBS and supplemented with invasion medium DMEM/INV (containing 1% human serum albumin, 25nM HEPES) with or without S. aureus 6850 (MOI=0.1) in presence of 50 μM U0126 or solvent control. 3 hrs post bacterial infection cells were treated with DMEM/FBS containing 10% FBS, 2 μg/ml lysostaphin for 20 min to remove non-internalized bacteria. After an additional wash with PBS cells were supplemented with infection medium DMEM/BA (0.2% BA, 1 mM $MgCl_2$, 0.9 mM $CaCl_2$, 100 U/ml penicillin, 0.1 mg/ml streptomycin) containing 50 μM U0126 or solvent. After an incubation period of 18 hrs at 37° C. cell morphology was monitored by light microscopy.

Figure 14:
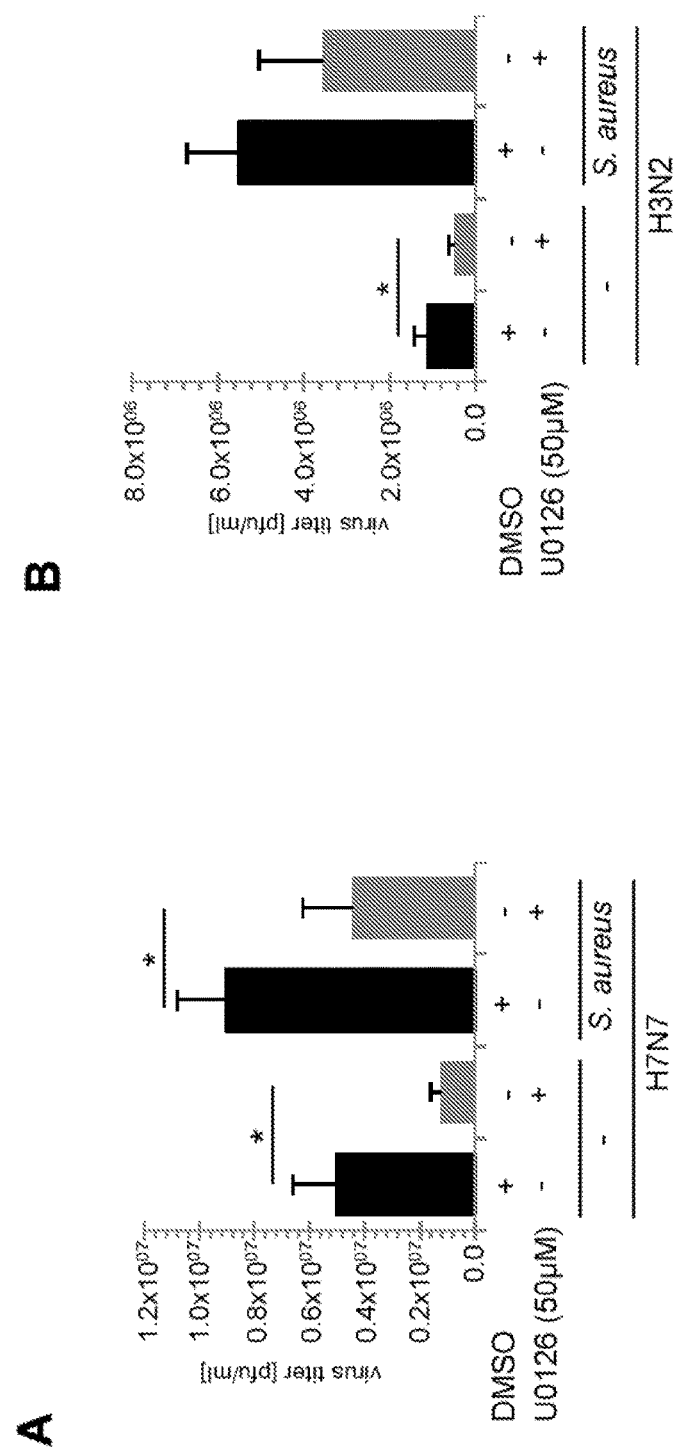

FIG. 14: Inhibition of MEK/ERK signaling results in reduced viral titers during singular and co-infection.

Human lung epithelial cells (A549) were infected with the avian influenza virus strain A/FPV/Bratislava/79 (H7N7) (A, C) or the human influenza virus strain A/Wisconsin/67/2005 (H3N2) (B, D) at a multiplicity of infection (MOI=0.001) (A, C), (MOI=0.5) (B, D) at 37° C. After 30 min the virus dilution was removed, cells were rinsed with PBS and supplemented with invasion medium DMEM/INV (containing 1% human serum albumin, 25nM HEPES) with or without S. aureus 6850 (MOI=0.1) in presence of 50 μM U0126 or solvent control. 3 hrs post bacterial infection cells were treated with DMEM/FBS containing 10% FBS, 2 μg/ml lysostaphin for 20 min to remove extracellular bacteria. After an additional wash with PBS cells were supplemented with infection medium DMEM/BA (0.2% BA, 1 mM $MgCl_2$, 0.9 mM $CaCl_2$, 100 U/ml penicillin, 0.1 mg/ml streptomycin) containing 50 μM U0126 or solvent. After an incubation period of 18 hrs at 37° C. viral titers were determined by standard plaque assay. Viral titers are depicted as plaque forming units/ml (PFU/ml) with a linear (A, B) or logarithmic scale (C, D). Data represent the means±SD of four independent experiments with two biological samples. Statistical significance was evaluated by a two-tailed one sample t-test (*p<0.05;**p<0.01).

Figure 15:
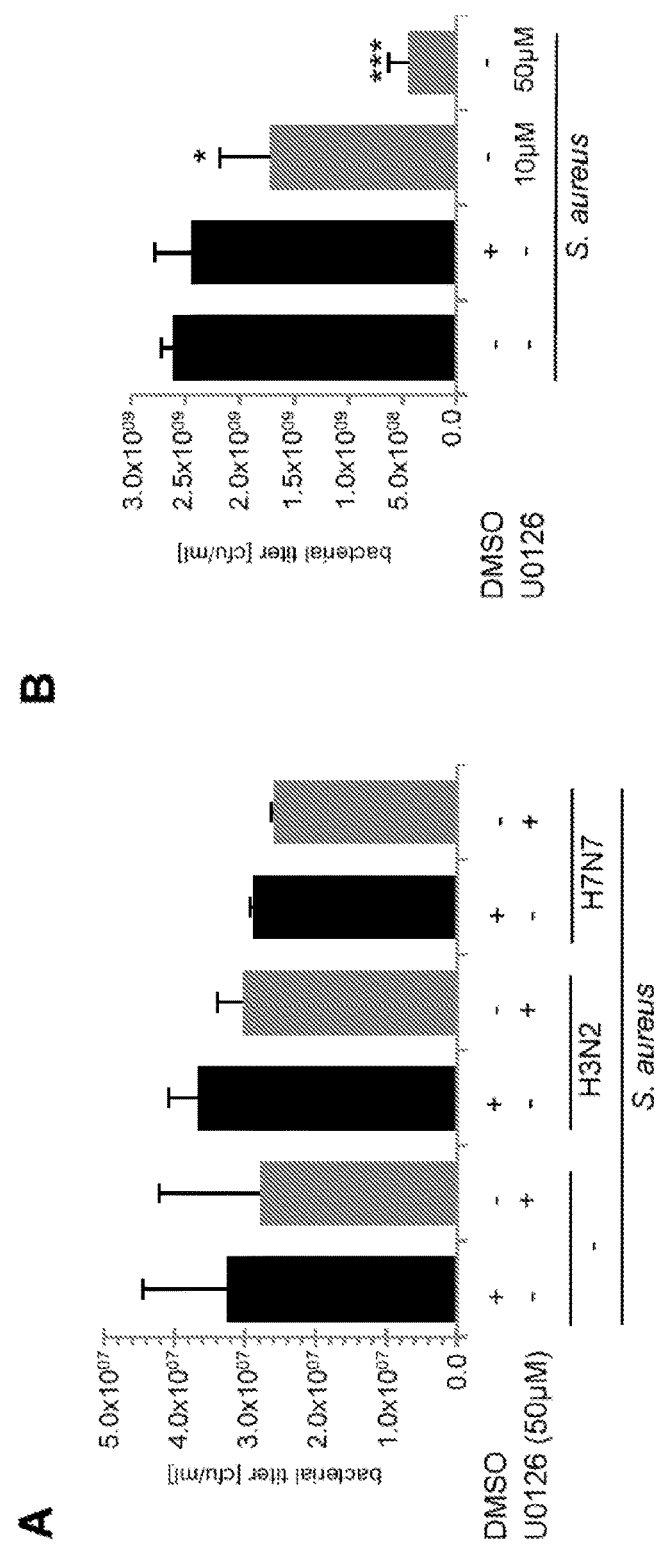

FIG. 15: MEK inhibition by administration of U0126 results in reduced bacterial growth.

Human lung epithelial cells (A549) were infected with the avian influenza virus strain A/FPV/Bratislava/79 (H7N7) or the human influenza virus strain A/Wisconsin/67/2005 (H3N2) (A, C) at a multiplicity of infection (MOI=0.001) (H7N7) or (MOI=0.5) (H3N2) at 37° C. After 30 min the virus dilution was removed, cells were rinsed with PBS and supplemented with invasion medium DMEM/INV (containing 1% human serum albumin, 25nM HEPES) with or without S. aureus 6850 (MOI=0.1) (A) in presence of 50 μM U0126 or solvent control. 3 hrs post bacterial infection cells were treated with DMEM/FBS containing 10% FBS, 2 μg/ml lysostaphin for 20 min (A, C) to remove non-internalized bacteria. After an additional wash with PBS cells were supplemented with infection medium DMEM/BA (0.2% BA, 1 mM $MgCl_2$, 0.9 mM $CaCl_2$, 100 U/ml penicillin, 0.1 mg/ml streptomycin) containing 50 μM U0126 or solvent. Amounts of internalized bacteria were determined by serial dilution of cell lysates on agar plates 18 hrs post infection (A, C). The impact of U0126 on bacterial growth was analyzed by administration of U0126 as indicated to an over-night culture of S. aureus 6850 (100 CFU/ml). After 16 hrs serial dilutions were plated on BHI agar (B, D). Bacterial titers are depicted as colony forming units/ml (CFU/ml) with a linear (A, B) or logarithmic scale (C, D). Data represent the means±SD of four (A, C) or three (B, D) independent experiments with two biological samples. Statistical significance was evaluated by a two-tailed two sample t-test (***p<0.001).

Figure 16:
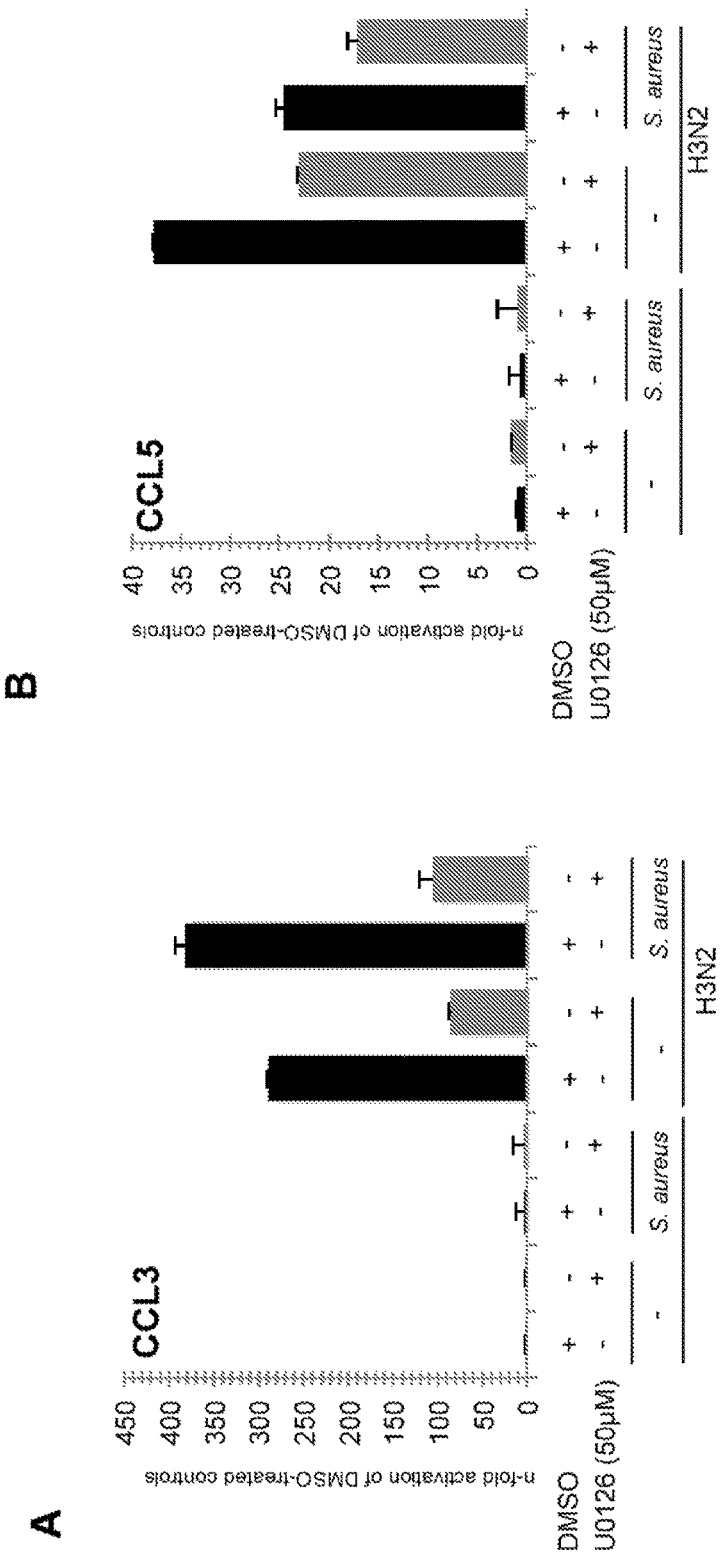

FIG. 16: Inhibition of the MEK/ERK signaling leads to reduction of viral proteins and pro-inflammatory chemokines.

Human lung epithelial cells (A549) were infected with the human influenza virus strain A/Wisconsin/67/2005 (H3N2) at a multiplicity of infection (MOI=5) at 37° C. After 30 min the virus dilution was removed, cells were rinsed with PBS and supplemented with invasion medium DMEM/INV (containing 1% human serum albumin, 25nM HEPES) with or without S. aureus 6850 (MOI=50) in presence of 50 μM U0126 or solvent control. 3 hrs post bacterial infection cells were treated with DMEM/FBS containing 10% FBS, 100 μg/ml Gentamicin for 30 min to remove extracellular bacteria. After an additional wash with PBS cells were supplemented with infection medium DMEM/BA (0.2% BA, 1 mM $MgCl_2$, 0.9 mM $CaCl_2$, 100 U/ml penicillin, 0.1 mg/ml streptomycin) containing 50 μM U0126 or solvent. After an incubation period of 8 hrs at 37° C. mRNA levels of CCL3 and CCL5 were analyzed by qRT-PCR with specific primers (A, B). Viral protein expression (PB-1) and the level of ERK-1/2 phosphorylation, as well as bacterial cell wall components (PGN) were determined by western blot analysis (C). Data represent preliminary results of three biological samples and two technical replicates within one experiment.

Figure 17:
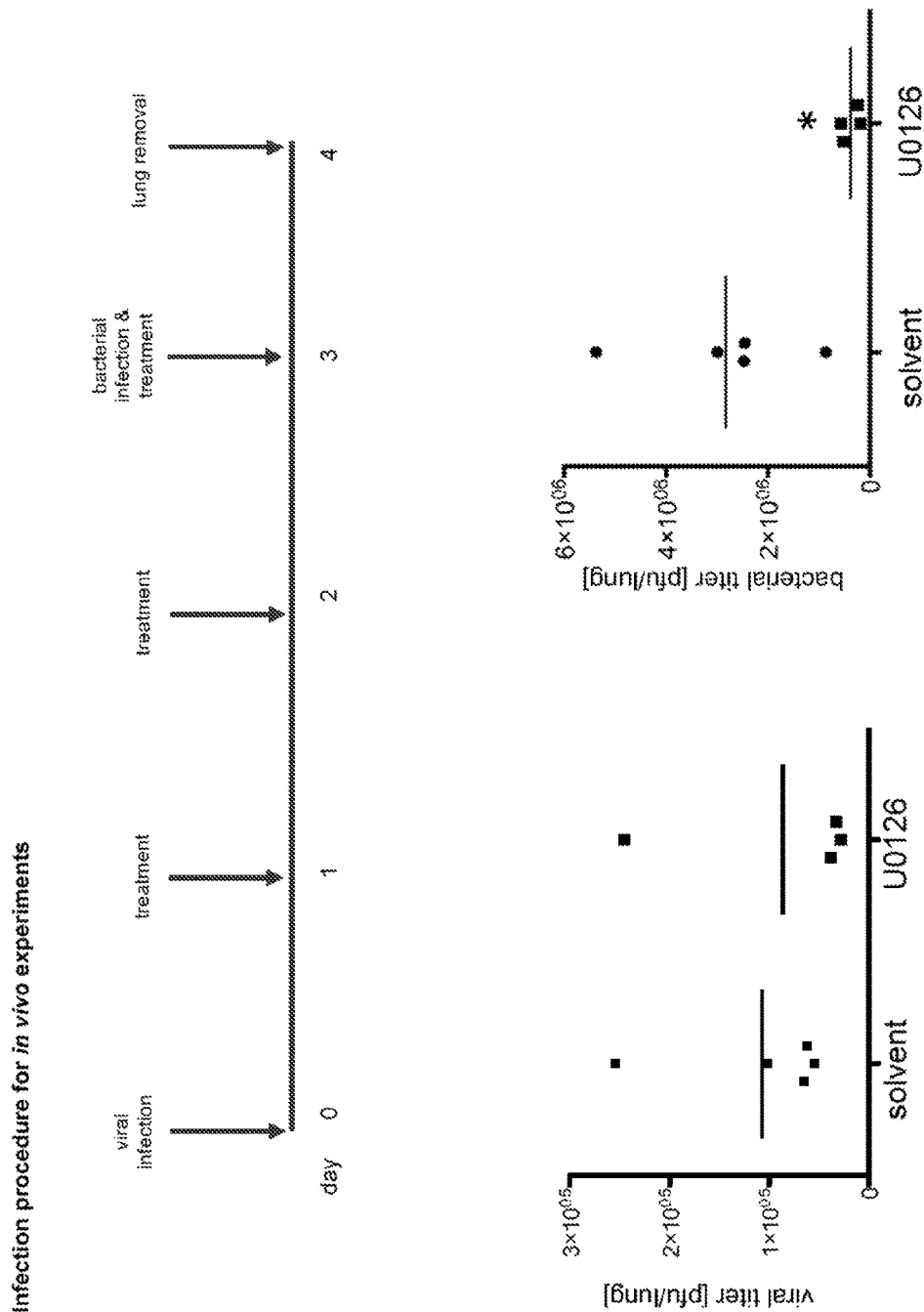

FIG. 17: Administration of U0126 leads to reduced bacterial titers in vivo independent of viral titers. 12 weeks old Balb/C mice were infected with 50 PFU of the influenza virus strain A/Puerto Rico/8/34 (PR8, H1N1) on day 0 (anesthesized with Isoflurane). Starting on day 1 mice were treated daily with i.p. injection of 30 mg/kg/day U0126 or solvent control (10% DMSO, 30% Cremophor EL, 60% PBS). On day 3 mice were infected with $5*10^7$ CFU of Staphylococcus aureus 6850 under anesthesia with Isoflurane and directly treated with U0126 or solvent control. On day 4 lungs were removed and homogenized in PBS (0.1 g per 1000 µl PBS). For calculation of bacterial titers serial dilutions of the homogenate were plated on BHI agar. For determination of viral titers a standard plaque assay was performed. Statistical analysis was done using Mann-Whitney U Test (*p<0,05).

Figure 18:
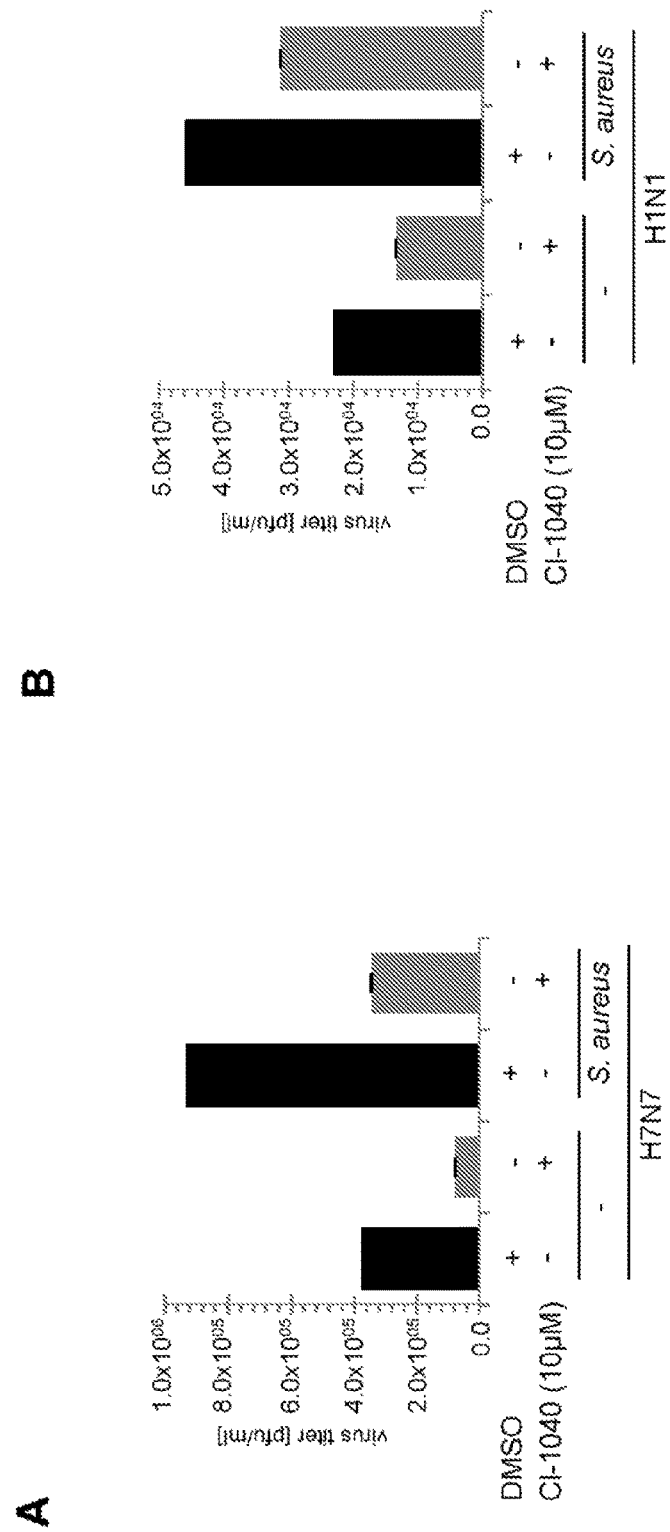

FIG. 18: The specific MEK inhibitor CI-1040 reduces viral titers in singular and co-infection.

Human lung epithelial cells (A549) were infected with the avian influenza virus strain A/FPV/Bratislava/79 (H7N7) (A, C) or the human influenza virus strain A/Puerto Rico/8/34 (H1N1) (B, D) at a multiplicity of infection (MOI=0.001) at 37° C. After 30 min the virus dilution was removed, cells were rinsed with PBS and supplemented with invasion medium DMEM/INV (containing 1% human serum albumin, 25nM HEPES) with or without S. aureus 6850 (MOI=0.1) in presence of 10 µM CI-1040 or solvent control. 3 hrs post bacterial infection cells were treated with DMEM/FBS containing 10% FBS, 2 µg/ml lysostaphin for 20 min to remove extracellular bacteria. After an additional wash with PBS cells were supplemented with infection medium DMEM/BA (0.2% BA, 1 mM $MgCl_2$, 0.9 mM $CaCl_2$, 100 U/ml penicillin, 0.1 mg/ml streptomycin) containing 10 µM CI -1040 or solvent. After an incubation period of 18 hrs at 37° C. viral titers were determined by standard plaque assay. Viral titers are depicted as plaque forming units/ml (PFU/ml) with a linear (A, B) or logarithmic scale (C, D). Data represent the means of two independent experiments with two biological samples.

FIG. 19: Administration of CI-1040 has an inhibitory effect on bacterial growth in vitro.

The impact of CI-1040 on bacterial growth was analyzed by administration of CI-1040 in different concentrations (as indicated) to an over-night culture of S. aureus 6850 (100 CFU/ml). After 16hrs serial dilutions were plated on BHI agar (A, B). Bacterial titers are depicted as colony forming units/ml (CFU/ml) with a linear (A) or logarithmic scale (B). Data represent preliminary data with two biological samples.

Figure 20:
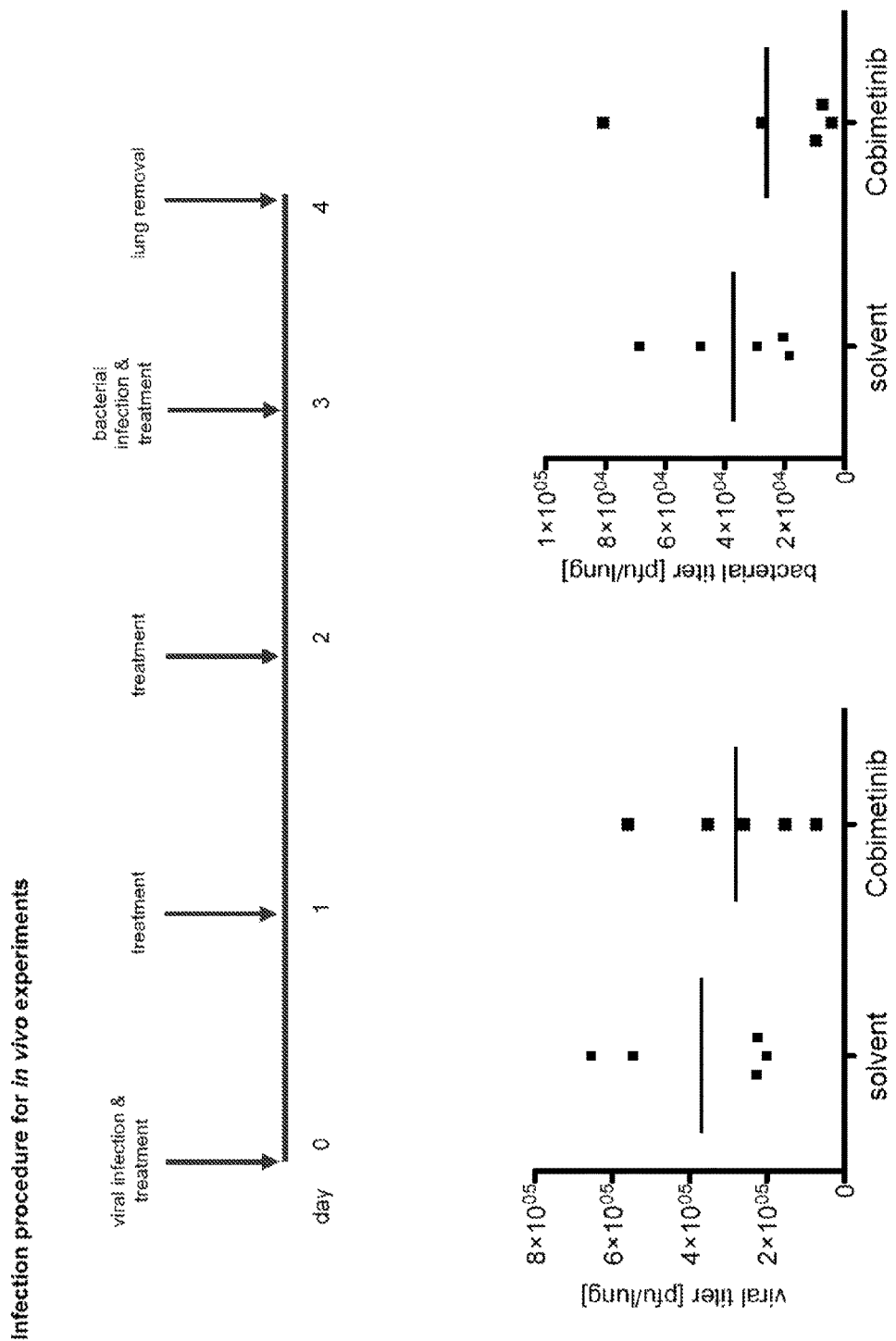

FIG. 20: Treatment with the specific MEK inhibitor Cobimetinib (GDC-0973) reduces pathogen load in vivo.

8 weeks old Balb/C mice (5 per group) were infected with 50 PFU of influenza virus strain A/Puerto Rico/8/34 (PR8, H1N1) on day 0 (anesthesized with Isoflurane). 6 hrs post viral infection mice were treated with oral administration of 10 mg/kg/day Cobimetinib or solvent control (10% DMSO, 5% Tween 20, 85% PBS). Treatment was then performed daily. On day 3 mice were infected with $5*10^7$ CFU of Staphylococcus aureus 6850 under anesthesia with Isoflurane and 6 hrs later treated with Cobimetinib or solvent control. On day 4 lungs were removed and homogenized in PBS (0.1 g per 1000 µl PBS). For calculation of bacterial titers serial dilutions of the homogenate were plated on BHI agar. For determination of viral titers a standard plaque assay was performed. Statistical analysis was done using Mann-Whitney U test.

Figure 21:
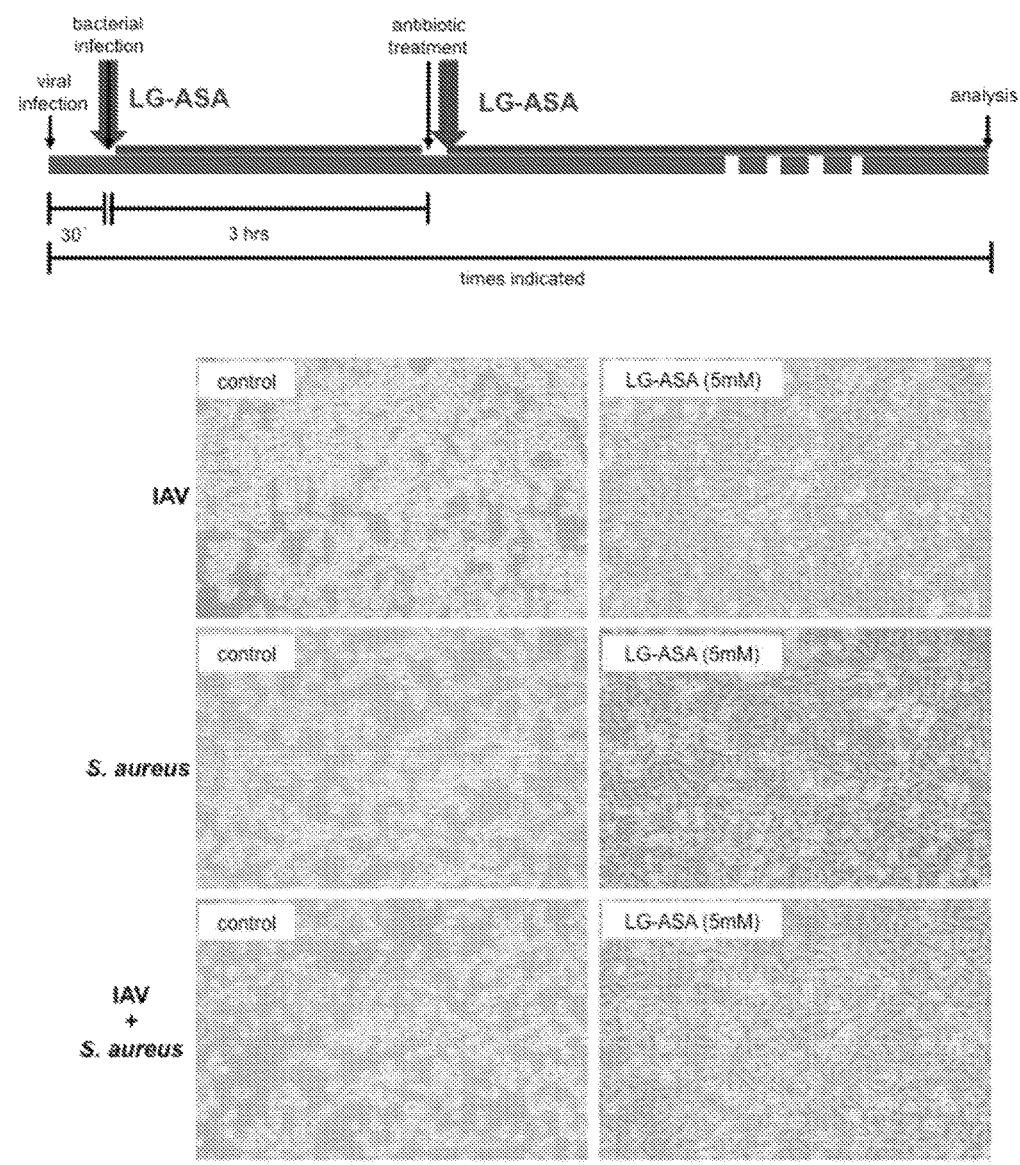

FIG. 21: LG-ASA improves cell morphology upon infection with influenza A virus (IAV) and/or Staphylococcus aureus (S. aureus)

Human lung epithelial cells (A549) were infected with the influenza virus strain A/Puerto Rico/8/34 (H1N1) at a multiplicity of infection (MOI=0.1) dissolved in PBS/BA [0.2% bovine serum albumin, 1 mM $MgCl_2$, 0.9 mM $CaCl_2$, 100 U/ml penicillin, 0.1 mg/ml streptomycin] at 37° C. After 30 min incubation, the virus dilution was aspirated, cells were rinsed with PBS and supplemented with invasion medium DMEM/INV [1% human serum albumin, 25 nmol/l HEPES] with or without S. aureus SH1000 (MOI=0.1) in presence of 5 mM LG-ASA or solvent control. 3 hrs post bacterial infection cells were treated with antibiotics [DMEM, 10%FBS, 2 µg/ml lysostaphin, 20 min] to remove extracellular bacteria. After an additional wash with PBS cells were supplemented with DMEM/INV containing 5 mM LG-ASA or solvent. After an incubation period of 18 hrs at 37° C. cell morphology was monitored by light microscopy.

Figure 22:
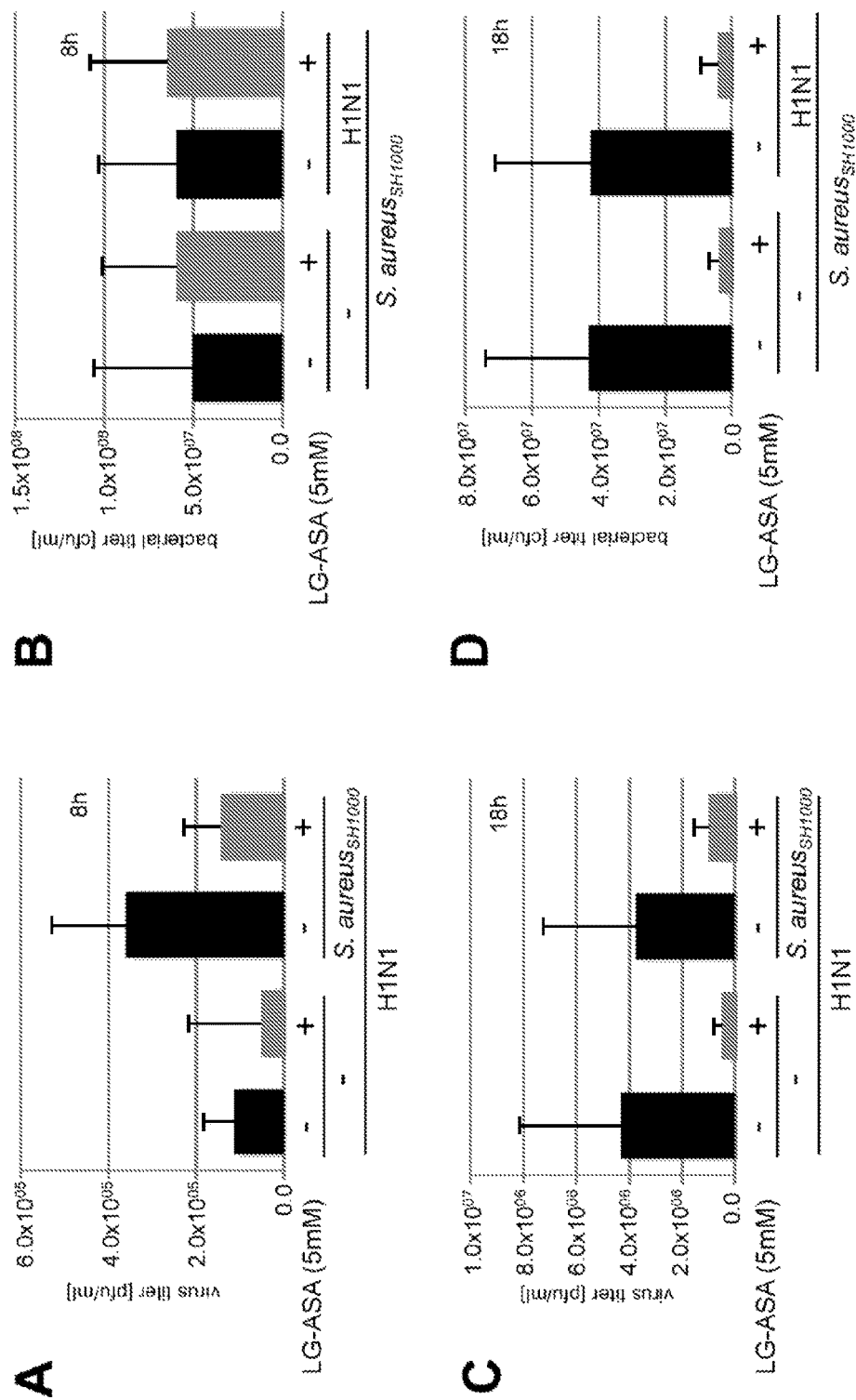

FIG. 22: The NFκB inhibitor LG-ASA reduces influenza virus titers and S. aureus load Human lung epithelial cells (A549) were infected with the influenza virus strain A/Puerto Rico/8/34 (H1N1) at a multiplicity of infection (MOI=0.1) dissolved in PBS/BA [0.2% bovine serum albumin, 1 mM $MgCl_2$, 0.9 mM $CaCl_2$, 100 U/ml penicillin, 0.1 mg/ml streptomycin] at 37° C. (A-H). After 30 min incubation, the virus dilution was aspirated, cells were rinsed with PBS and supplemented with invasion medium DMEM/INV [1% human serum albumin, 25 nmol/l HEPES] with or without S. aureus SH1000 (MOI=50) (A, B), (MOI=0.001) (C-D), S. aureus 6850 (MOI=50) (E, F), (MOI=0.1) (G, H) in presence of 5 mM LG-ASA or solvent control. 3 hrs post bacterial infection cells were treated with antibiotics [DMEM, 10%FBS, 2 µg/ml lysostaphin, 20 min] to remove extracellular bacteria. After an additional wash with PBS cells were supplemented with DMEM/INV containing 5 mM LG-ASA or solvent. After an incubation period of 8 hrs (A, B, E, F) or 18 hrs (C, D, G, H) at 37° C. IAV titers (A, C, E, G) were determined by standard plaque assays. Cells were lysed by a hypotonic shock and amounts of internalized bacteria (B, D, F, H) were determined by serial dilution on agar plates. Data represent the means±SD of three (A-H) with two biological samples. Statistical significance was evaluated by a two-tailed one sample t-test (*p<0.05;**p<0.01).

Figure 23:
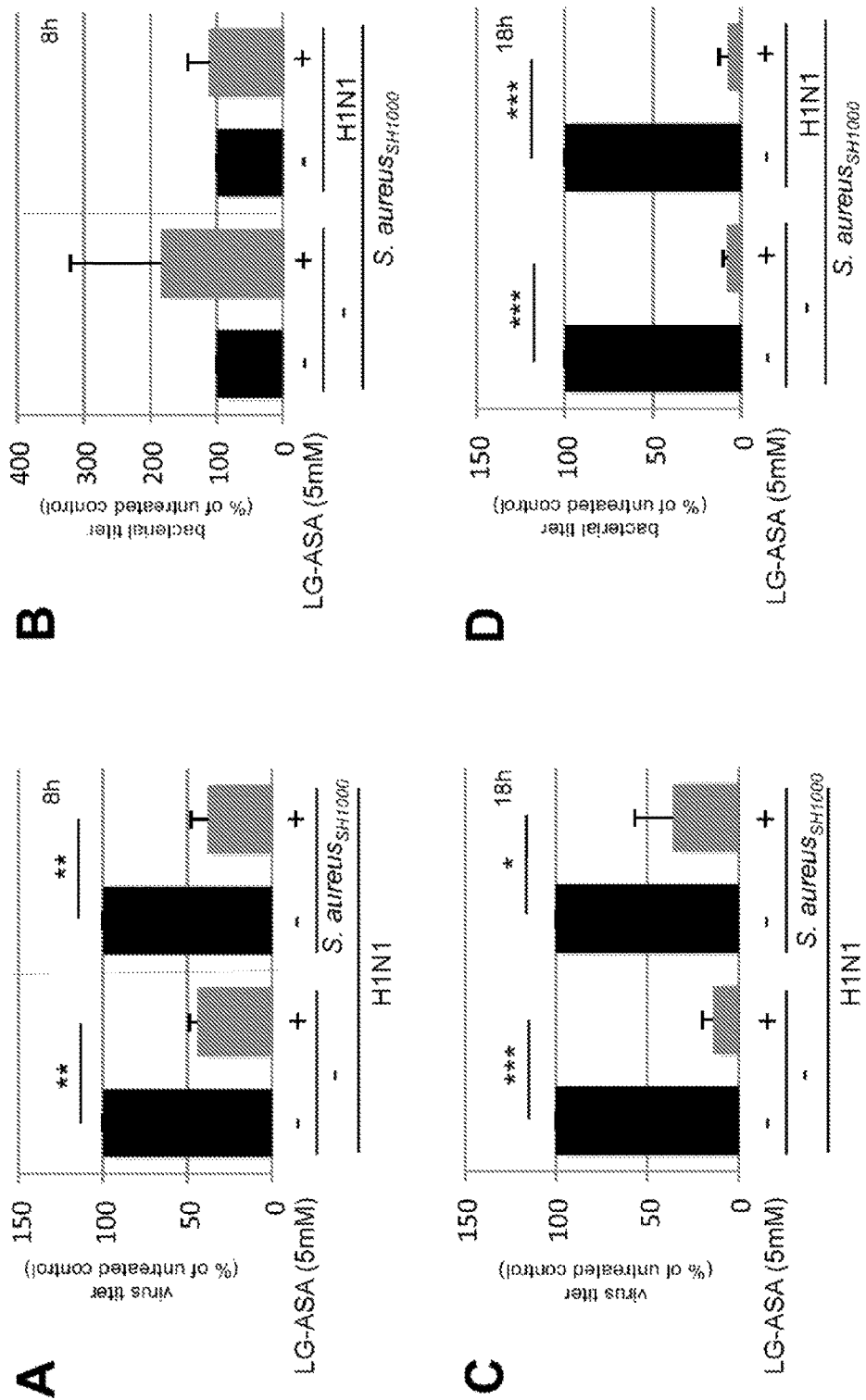

FIG. 23: The NFκB inhibitor LG-ASA reduces influenza virus titers and S. aureus load This figure presents data obtained as in FIG. 22 in a different way. In particular, the untreated controls of each experiment were arbitrarily set as 100% and then the means were calculated. Statistical significance was evaluated by a two-tailed one sample t-test (*p<0.05;**p<0.01).

Figure 24:
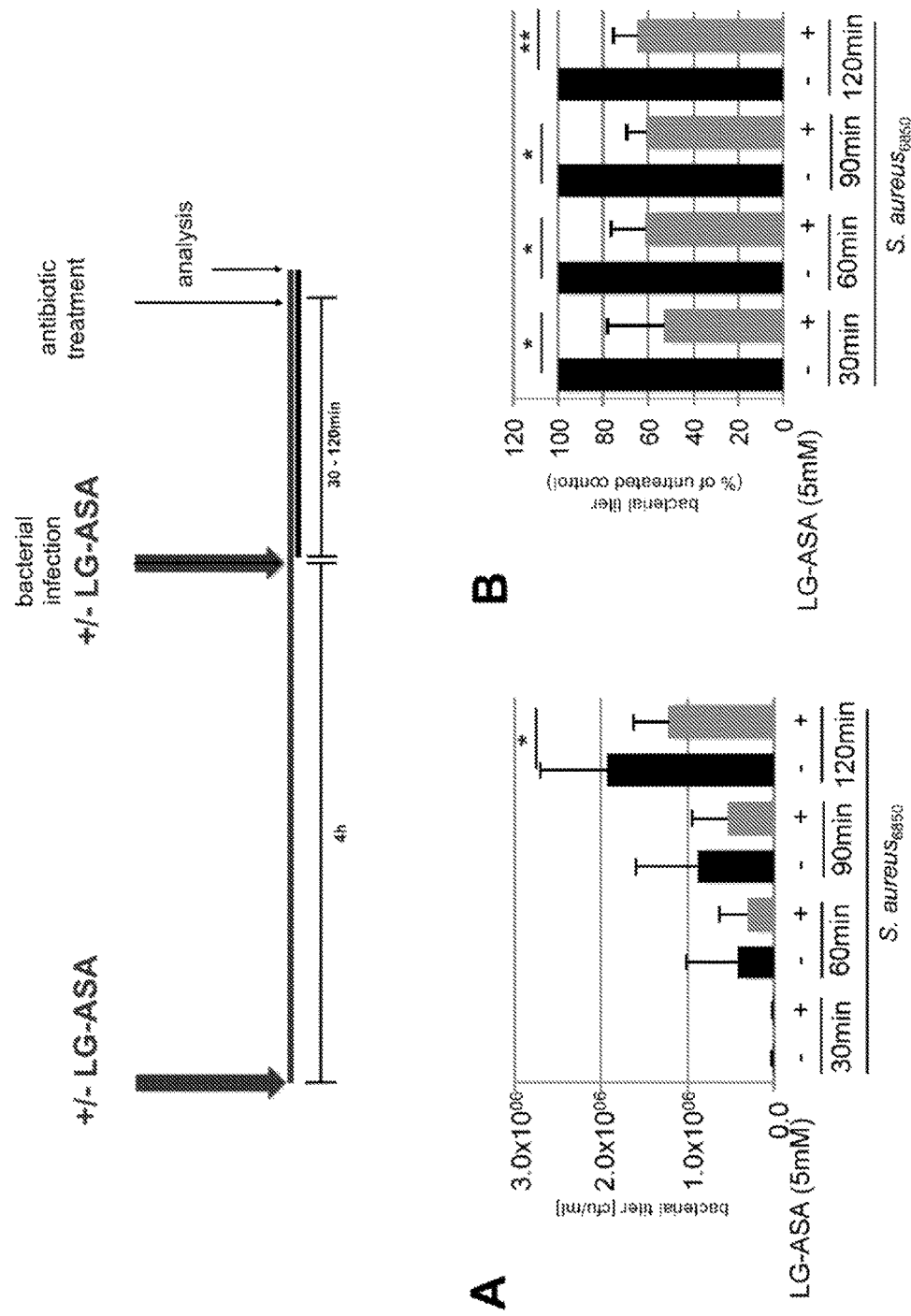

FIG. 24: Inhibition of NFκB signaling results in reduced bacterial internalisation Human lung epithelial cells (A549) were preincubated with 5 mM (A-D) and 10 mM (C, D) LG-ASA for 4 h and then infected with *S. aureus* 6850 (MOI=50) (A, B) for 30-120 min and USA 300 (MOI=5) (C, D) for 120 min in presence and absence of the indicated amounts of LG-ASA dissolved in DMEM/INV [1% human serum albumin, 25 nmol/l HEPES]. 30-120 min post infection an antibiotic wash [DMEM, 10%FBS, 2 μg/ml lysostaphin, 20 min] was included to remove non-internalized bacteria. Cells were washed with PBS three times and lysed by hypotonic shock. Amounts of internalized bacteria were determined by serial dilution on agar plates (A-D). Data (A, C) represent the means±SD of three independent experiments with two biological samples. In FIG. 24 B, D the untreated controls of each experiment were arbitrarily set as 100% and then the means were calculated. Statistical significance was evaluated by a two-tailed one sample t-test (*p<0.05;p<0.01; *p<0.001).

Figure 25:
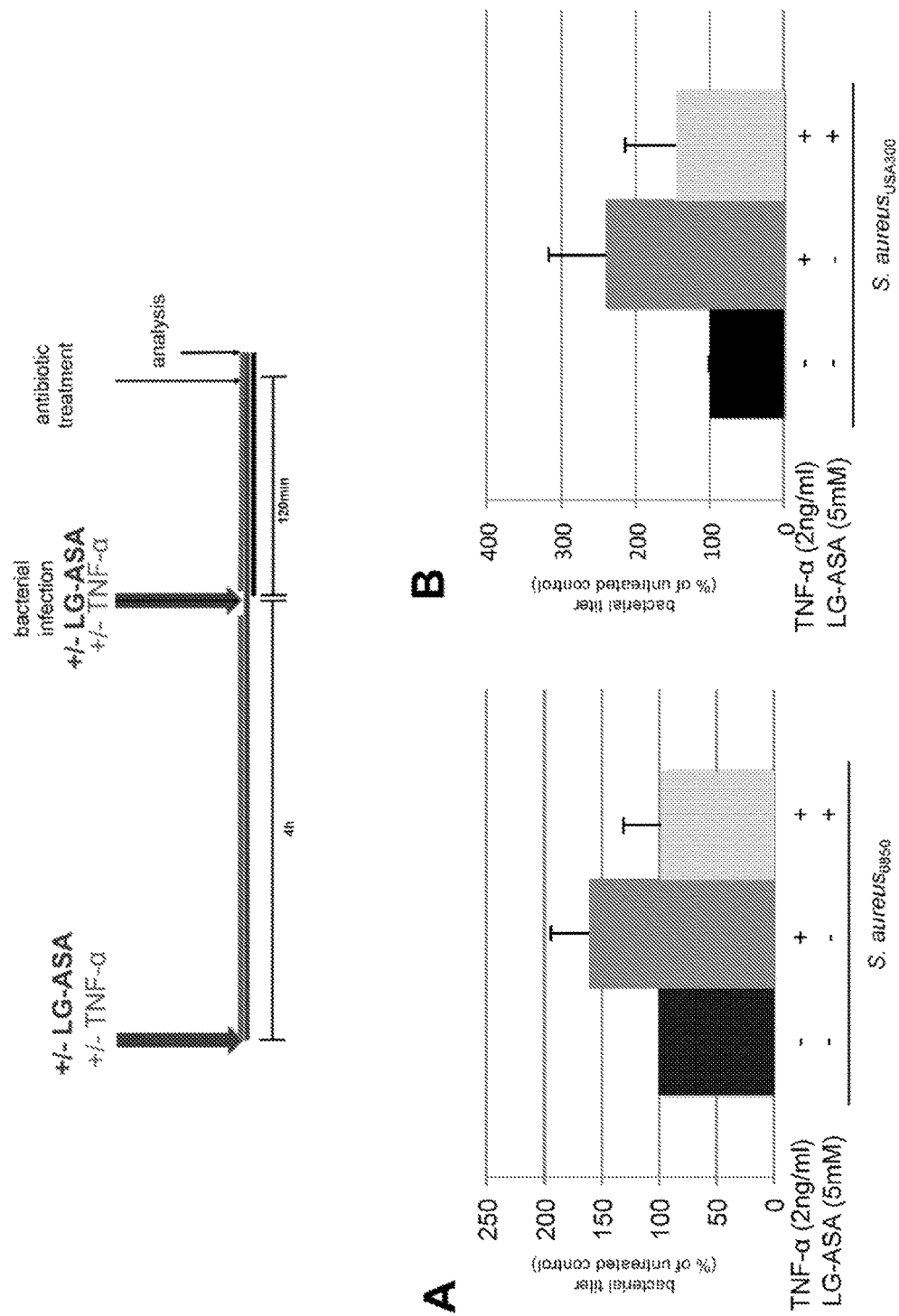

FIG. 25: Stimulation of NFκB signaling results in enhanced bacterial internalization Human lung epithelial cells (A549) were preincubated with 5 mM LG-ASA and 2.5 ng/ml TNF-alpha for 4 h and then infected with (A) *S. aureus* 6850 or (B) *S. aureus* USA300 (MOI=5) for 120 min in presence and absence of the indicated amounts of LG-ASA and TNF-alpha dissolved in DMEM/INV [1% human serum albumin, 25 nmol/l HEPES] (A). 120 min post infection an antibiotic wash [DMEM, 10% FBS, 2 μg/ml lysostaphin, 20 min] was included to remove non-internalized bacteria. Cells were washed with PBS three times and lysed by hypotonic shock. Amounts of internalized bacteria were determined by serial dilution on agar plates (A) 120 min post infection. (A) Data represent the means ±SD of four independent experiments with two biological samples. Statistical significance was evaluated by an one-way ANOVA followed by a multiple comparison test (*p<0.05; p<0.01; *p<0.001). (B) Data represent the means±SD of three independent experiments with three biological samples whereby the untreated controls of each experiment were arbitrarily set as 100% and then the means were calculated.

Figure 26:
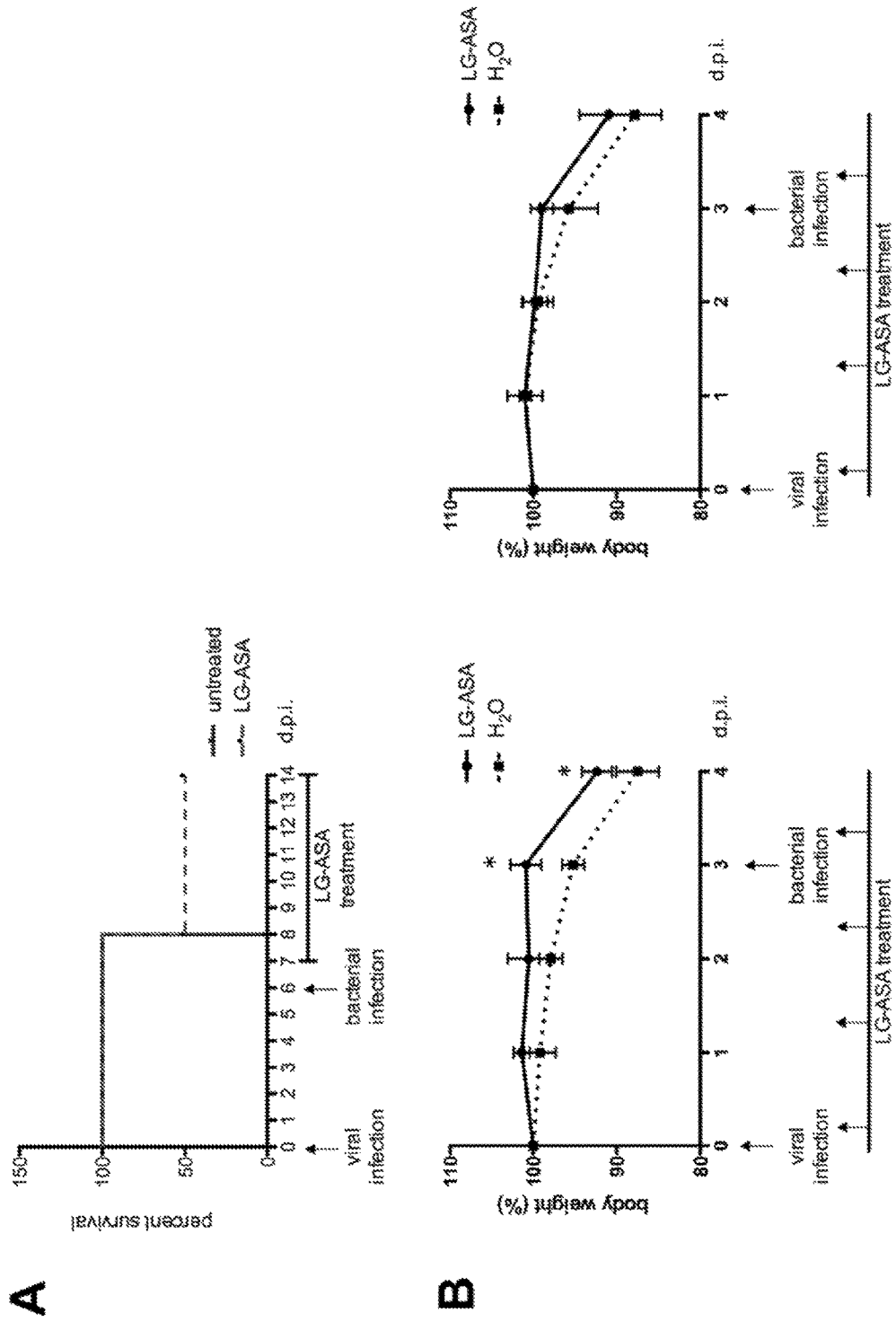

FIG. 26: Treatment of IAV/*S. aureus* co-infected mice with LG-ASA results in enhanced survival and reduced body weight loss (A) BALB/c mice (4 mice per group) were infected with 50 PFU of the influenza virus A/Puerto Rico/8/34 at day 0. On day 6 after influenza virus infection mice were additionally infected with $10^8$ CFU *S. aureus* 6850. On day 7 after influenza virus infection co-infected mice were treated once a day with LG-ASA (1M, 10 min) via inhalation. Survival was monitored for 14 days. While (4/4) (black line) untreated co-infected mice died 1 day after co-infection, (2/4) LG-ASA treated co-infected mice survived (grey line).

(B) Two independent experiments are depicted. 9 weeks old Balb/C mice (4 mice per group) were infected with 50 PFU of influenza virus A/Puerto Rico/8/34 on day 0 (anesthesized with Isoflurane) in the morning. 6 hrs post viral infection mice were weighed and treated with aerosolic $H_2O$ or 1M LG-ASA in an inhalation chamber for 10 min. This treatment was also performed on day 1, 2 and 3 at the same time as on day 0. On day 3 in the morning mice were infected with $5*10^7$ CFU of *Staphylococcus aureus* 6850 under anesthesia with Isoflurane. On day 4 mice were weighed the last time. Statistical analysis was done using Mann-Whitney U Test (*p<0.05).

DETAILED DESCRIPTION OF THE INVENTION/DETAILED DESCRIPTION OF A PREFERENTIAL EMBODIMENT

The following description includes information that may be useful in understanding the present invention. It is not an admission that any of the information provided herein is prior art or relevant to the presently claimed inventions, or that any publication specifically or implicitly referenced is prior art.

The above being said, the present invention relates to a MEK inhibitor, p38 inhibitor and/or NFκB inhibitor for use in a method for the prophylaxis and/or treatment of a co-infection comprising a bacterial infection and an influenza virus infection.

In addition the present invention relates to a MEK inhibitor, p38 inhibitor and/or NFκB inhibitor for use in a method for the prophylaxis and/or treatment of a bacterial infection.

Figure 1:
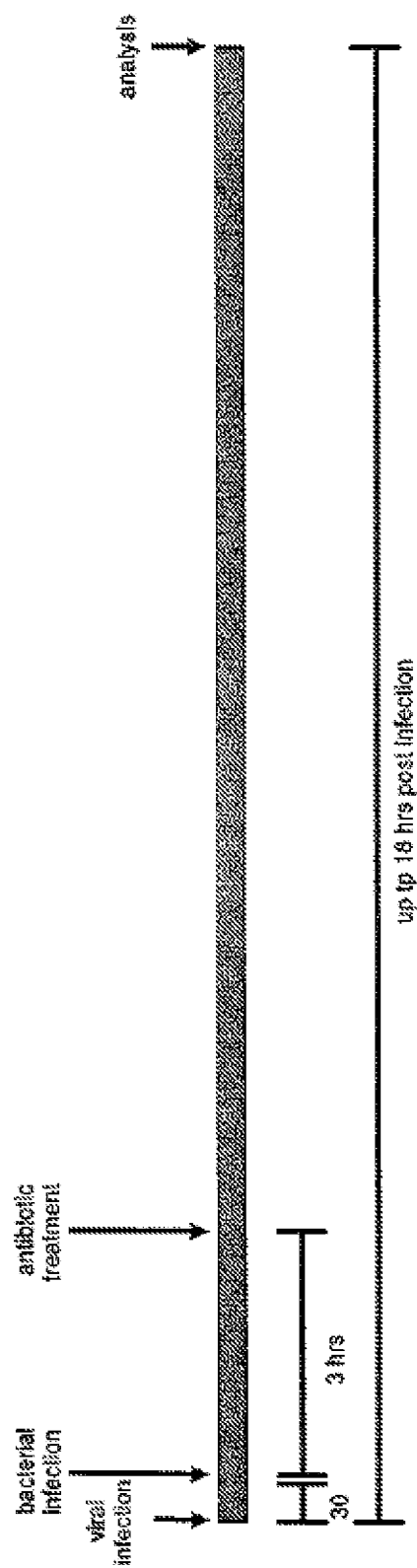
FIG. 1: Time scale of co-infection procedure. Cells were infected with IV for 30 min. Co-infection with S. aureus 6850 was conducted or cells were mock-treated. Extracellular bacteria were lysed and removed by antibiotic treatment 3 h post bacterial infection. After a PBS wash, cells were supplemented with fresh medium (DMEM/INV) and incubated up to 18 hrs of viral infection

When used herein, a "MEK inhibitor" may also be designated as a Mitogen Activated Proteinkinase (MAPK) kinase inhibitor. It is known that in a MAPK pathway, a MAPK kinase kinase (MAPKKK) activates a MAPK kinase (MAPKK) which in turn activates a MAPK which transduces a signal to, for example, a transcription factor or other kinases or effector/signal transducing protein; see, for example, FIG. 1 of Fremin and Meloche (Fremin and Meloche (2010), J. Hematol. Oncol. 11;3:8). MEK inhibitors of the invention preferably inhibit MEK1/2 of a subject, such as a mammal or bird as described herein. However, it may be that a MEK inhibitor of the invention does not only inhibit a MEK, preferably MEK1/2, but also its upstream kinase (i.e. MAPKKK), thereby exerting a dual inhibition. Without being bound by theory, PLX-4032 may be such a dual inhibitor. Hence, a MEK inhibitor of the invention may in a preferred aspect by a dual inhibitor, thereby inhibiting a MEK, preferably MEK1/2 and the corresponding upstream MAPKKK. MEK1/2 is the MAPKK in the Ras/Raf pathway, whereby Ras/Raf acts as MAPKKK and ERK1/2 acts as MAPK.

A MEK inhibitor can be a small molecule, large molecule, peptide, oligonucleotide, and the like. The MEK inhibitor may be a protein or fragment thereof or a nucleic acid molecule. Also included by the term MEK inhibitor is a pharmaceutically acceptable salt of the MEK inhibitor.

The determination of whether or not a compound is a MEK inhibitor is within the skill of one of ordinary skill in the art. In one embodiment, the MEK inhibitors are selected from the group consisting of the compounds/inhibitors listed in table 1.

The MEK inhibitors of the invention are selected preferably from U0126, PLX-4032, AZD6244, AZD8330, AS-703026, GSK-1120212, RDEA-119, RO-5126766, RO-4987655, CI-1040, PD-0325901, GDC-0973, TAK-733, PD98059, PD184352 ARRY-438162 and PF-3644022, preferably AZD8330, GSK-1120212, U0126, GDC-0973, CI-1040, PD0325901, ARRY-438162, PF-3644022 and AZD6244 and most preferably U0126, CI-1040, GDC-0973 (Cobimetinib), AZD8330, GSK-1120212, most preferably U0126, GDC-0973, CI-1040, AZD8330 and GSK-1120212.

Some of these inhibitors are further described in table 1 below.

TABLE 1

MEK inhibitors.

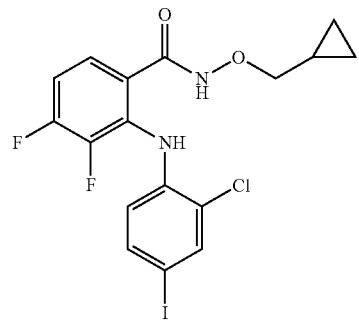 [SMILES: O=C(NOCC1CC1)c1ccc(F)c(F)c1Nc1ccc(I)cc1Cl]

Structural formula I
CI-1040
2-(2-chloro-4-iodophenylamino)-N-
(cyclopropylmethoxy)-3,4-difluorobenzamide

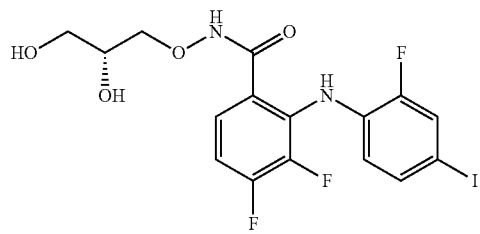 [SMILES: O=C(NOC[C@H](O)CO)c1ccc(F)c(F)c1Nc1ccc(I)cc1F]

Structural formula II
PD0325901
(R)-N-(2,3-dihydroxypropoxy)-
3,4-difluoro-2-(2-fluoro-4-iodo-
phenylamino)benzamide

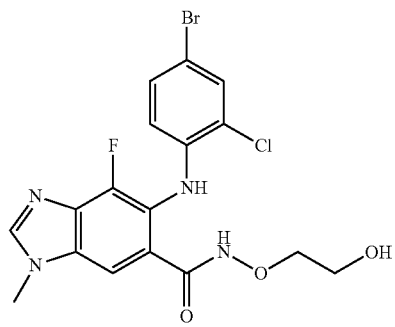 [SMILES: Cn1cnc2c(F)c(Nc3ccc(Br)cc3Cl)c(C(=O)NOCCO)cc21]

Structural formula III
AZD6244
6-(4-bromo-2-chlorophenylamino)-
7-fluoro-N-(2-hydroxyethoxy)-3-methyl-
3H-benzo[d]imidazole-5-carboxamide

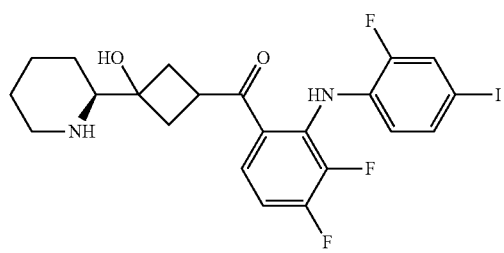 [SMILES: O=C(c1ccc(F)c(F)c1Nc1ccc(I)cc1F)C1CC(O)([C@@H]2CCCCN2)C1]

Structural formula IV
GDC-0973
[3,4-difluoro-2-[(2-fluoro-4-
iodophenyl)amino]phenyl]
[3-hydroxy-3-[(2S)-2-piperidinyl]-1-
azetidinyl]methanone

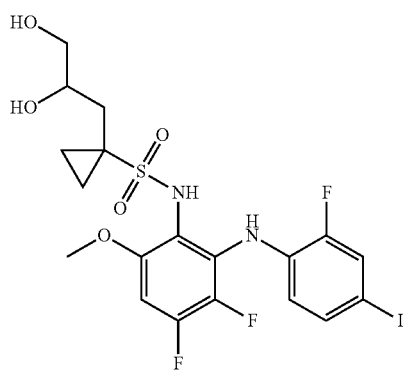 [SMILES: COc1cc(F)c(F)c(Nc2ccc(I)cc2F)c1NS(=O)(=O)C1(CC(O)CO)CC1]

Structural formula V
RDEA-119
(S)-N-(3,4-difluoro-2-(2-fluoro-4-iodophenyl-
amino)-6-methoxyphenyl)-1-(2,3-
dihydroxypropyl)cyclopropane-1-sulfonamide TABLE 1-continued MEK inhibitors.

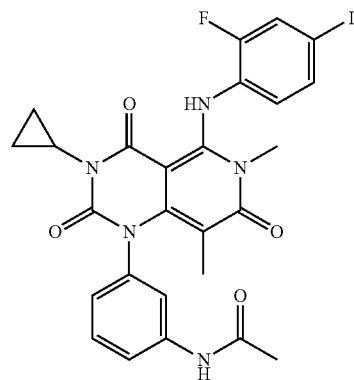 [SMILES: CC(=O)Nc1cccc(-n2c(=O)n(C3CC3)c(=O)c3c(Nc4ccc(I)cc4F)n(C)c(=O)c(C)c32)c1]

Structural formula VI
GSK-1120212
N-(3-(3-cyclopropyl-5-(2-fluoro-4-iodophenylamino)-6,8-dimethyl-2,4,7-trioxo-3,4,6,7-tetrahydropyrido[4,3-d]pyrimidin-1(2H)-yl)phenyl)acetamide

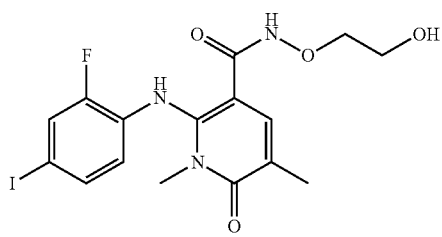 [SMILES: Cc1cc(C(=O)NOCCO)c(Nc2ccc(I)cc2F)n(C)c1=O]

Structural formula VII
AZD8330
2-(2-fluoro-4-iodophenylamino)-N-(2-hydroxyethoxy)-1,5-dimethyl-6-oxo-1,6-dihydropyridine-3-carboxamide

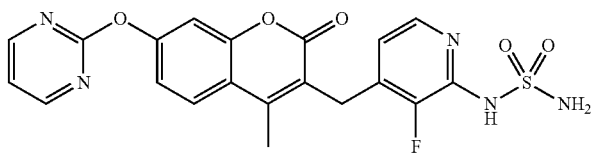 [SMILES: Cc1c(Cc2ccnc(NS(N)(=O)=O)c2F)c(=O)oc2cc(Oc3ncccn3)ccc12]

Structural formula VIII
RO5126766
C20H16FN5O5S

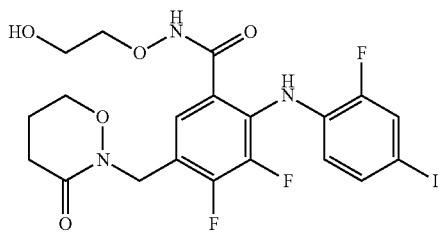 [SMILES: O=C(NOCCO)c1cc(CN2OCCCC2=O)c(F)c(F)c1Nc1ccc(I)cc1F]

Structural formula IX
RO4987655
C20H19F3IN3O5

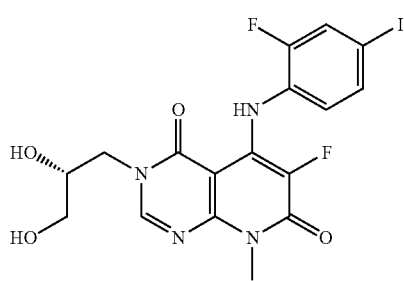 [SMILES: Cn1c(=O)c(F)c(Nc2ccc(I)cc2F)c2c(=O)n(C[C@@H](O)CO)cnc21]

Structural formula X
TAK-733
(R)-3-(2,3-dihydroxypropyl)-6-fluoro-5-(2-fluoro-4-iodophenylamino)-8-methylpyrido[2,3-d]pyrimidine-4,7(3H,8H)-dione

TABLE 1-continued

MEK inhibitors.

Zelborat (vemurafenib)

Structural formula XI
PLX-4032
N-[3-[[5-(4-Chlorophenyl)-1H-pyrrolo[2,3-b]pyridin-3-yl]carbonyl]-2,4-difluorophenyl]-1-propanesulfonamide Structural formula XII
AS703026
(S)-N-(2,3-dihydroxypropyl)-3-(2-fluoro-4-iodophenylamino)isonicotinamide Structural formula XIII
PD98059
2-(2-amino-3-methoxyphenyl)-4H-chromen-4-one Structural formula XIV
PD184352
2-(2-chloro-4-iodophenylamino)-N-(cyclopropylmethoxy)-3,4-difluorobenzamide Also preferred is a selection from PLX-4032, AZD6244, AZD8330, GDC-0973, RDEA119, GSK1120212, RO51267766, RO4987655, TAK-733, and AS703026. Even more preferably, they are selected from AZD6244, AZD8330, GSK1120212 and PLX-4032 or from PD-0325901, AZD-6244, AZD-8330 and RDEA-119. These MEK inhibitors are known in the art and, for example, described in Table 1 of Fremin and Meloche (2010), J. Hematol. Oncol. 11;3:8.

More information on some of these inhibitors can also be obtained from Arthur and Ley (2013) Mitogen-activated protein kinases in innate immunity; Nature Reviews Immunology 13,679-692(2013).

Indeed, as demonstrated in the appended Examples, the MEK inhibitor U0126 and CI-1040 disclosed herein show an effect in co-infection scenarios as well as on bacterial infection alone.

Also a p38 inhibitor is provided for use in the methods for the prophylaxis and/or treatment of a co-infection or bacterial infection of the present invention. A "p38 MAP kinase inhibitor" is well known in the art. The terms "p38 inhibitor," "p38 kinase inhibitor," and "p38 MAP kinase inhibitor" are used interchangeably herein. In the context of the present invention a p38 MAP kinase inhibitor inhibits p38 MAP kinase. Preferably, the p38 MAP kinase inhibitor inhibits one of the isoforms of p38 MAP kinase, preferably one of the four isoforms (α, β, γ or δ) of p38 MAP kinase with the α-isoform being preferred, more preferably it inhibits any combination of two isoforms of p38 MAP kinase, even more preferably it inhibits any combination of three isoforms of p38 MAP kinase and most preferably, it inhibits all isoforms or the α, β, γ and δ isoform of p38 MAP kinase. In some embodiments, the p38 MAP kinase inhibitor inhibits the isoform of p38 that is involved in inflammatory diseases, autoimmune diseases, destructive bone disorders, proliferative disorders, infectious diseases, viral diseases or neurodegenerative diseases. It is reported that the α-isoform of p38 MAP kinase is involved in inflammation, proliferation, differentiation and apoptosis, whereas the biological functions of p38 β, p38 δ and p38 γ are not yet understood completely. Accordingly, it is preferred herein that the p38 MAP kinase inhibitor inhibits the α-isoform.

A p38 MAP kinase inhibitor can be a small molecule, large molecule, peptide, oligonucleotide, and the like. The p38 MAP kinase inhibitor may be a protein or fragment thereof or a nucleic acid molecule. Also included by the term p38 inhibitor is a pharmaceutically acceptable salt of the 38 inhibitor.

The determination of whether or not a compound is a p38 kinase inhibitor is within the skill of one of ordinary skill in the art.

There are many examples of p38 inhibitors in the art. U.S. Pat. Nos. 5,965,583, 6,040,320, 6,147,096, 6,214,830, 6,469,174, 6,521,655 disclose compounds that are p38 inhibitors. U.S. Pat. Nos. 6,410,540, 6,476,031 and 6,448,257 also disclose compounds that are p38 inhibitors. Similarly, U.S. Pat. Nos. 6,410,540, 6,479,507 and 6,509,361 disclose compounds that are asserted to be p38 inhibitors. U.S. Published Application Nos. 20020198214 and 20020132843 disclose compounds that are said to be p38 inhibitors. Another p38 MAP kinase inhibitor is BIRB 796 BS (1-(5-tert-butyl-2-p-tolyl-2H-pyrazol-3-yl)-3[4-(2-morpholin-4-yl-ethoxy)-naphthalen-1-yl]-urea); see Branger (2002), J. Immunol. 168:4070-4077 or U.S. Pat. No. 6,319,921 for further p39 MAP kinase inhibitors.

Other p38 MAP kinase inhibitors are AMG 548 (Amgen), BIRB 796 (Boehringer Ingelheim), VX 702 (Vertex/Kissei), SCIO 469, SCIO 323 (Scios Inc.), SB 681323 (GlaxoSmithKline), PH-797804 (Pfizer) and Org-48762-0 (Organon NV); see, for example, Lee and Dominguez in Curr Med Chem. 2005;12(25):2979-2994 and Dominguez in Curr Opin Drug Discov Devel. 2005 July; 8(4):421-430.

According to the present invention, the inhibitor may exhibit its regulatory effect upstream or downstream of p38 MAP kinase or on p38 MAP kinase directly, with the latter mode of action being preferred. Examples of inhibitor regulated p38 MAP kinase activity include those where the inhibitor may decrease transcription and/or translation of p38 MAP kinase, may decrease or inhibit post-translational modification and/or cellular trafficking of p38 MAP kinase, or may shorten the half-life of p38 MAP kinase. The inhibitor may also reversibly or irreversibly bind p38 MAP kinase, inhibit its activation, inactivate its enzymatic activity, or otherwise interfere with its interaction with downstream substrates.

The four isoforms of the p38 MAP kinase share a high level of sequence homology. The alpha and beta isoforms of the p38 MAP kinase are closely related while the gamma and delta isoforms are more divergent. Given the high degree of structural similarity, it is not surprising that certain compounds with the ability to inhibit one p38 MAP kinase isoform can often inhibit other isoforms of the MAP kinase. Accordingly, in some embodiments, an inhibitor of p38 MAP kinase that is specific for the α-isoform of the kinase possesses at least three categories of structural features that are theorized to permit isoform specific inhibition.

Selective binding of a candidate p38 MAP kinase inhibitor can be determined by a variety of methods. The genes for the various isoforms of p38 MAP kinase are known in the art. One of ordinary skill in the art could readily clone and express the various isoforms of the kinase, purify them, and then perform binding studies with candidate compounds to determine isoform binding characteristics. This series of experiments was performed for the α-isoform of p38 MAP kinase and provided in U.S. Pat. No. 6,617,324 B1.

Another kinase selectivity assay is described in Mihara (2008), Br. J. Pharmacol. 154(1):153-164.

In some embodiments herein, a p38 MAP kinase inhibitor inhibits one of the four isoforms of p38 MAP kinase, more preferably it inhibits any combination of two isoforms of p38 MAP kinase, even more preferably it inhibits any combination of three isoforms of p38 MAP kinase, e.g., p38-α(MAPK14), -β(MAPK11), -γ(MAPK12 or ERK6). Alternatively, but also preferred, it inhibits all four isoforms of p38 MAP kinase.

In one embodiment, the p38 inhibitor is selected from the group consisting of the inhibitors listed in table 2 (FIG. 8). In another embodiment, the p38 inhibitor is selected from the group consisting of SB202190, LY2228820, CAY10571, SB 203580, Tie2 Kinase Inhibitor, 2-(4-Chlorophenyl)-4-(fluorophenyl)-5-pyridin-4-yl-1,2-dihydropyrazol-3-one, CGH 2466, SB220025, Antibiotic LL Z1640-2, TAK 715, SB202190 hydrochloride, SKF 86002, AMG548, CMPD-1, EO1428, JX 401, ML 3403, RWJ 67657, SB 202190, SB 203580, SB 203580 hydrochloride, SB 239063, SCIO 469, SX 011, TAK 715, Pamapimod, Losmapimod (GW856553), Dilmapimod (SB681323), VX 702, VX 745, Doramapimod (BIRB 796), BMS-582949, ARRY-797, PH797804, SCIO-469, preferably VX-702, SB202190, Pamapimod, Losmapimod (GW856553), Dilmapimod (SB681323), Doramapimod (BIRB 796), BMS-582949, ARRY-797, PH797804 and SCIO-469.

More information on some of these inhibitors can also be obtained from Arthur and Ley (2013) Mitogen-activated protein kinases in innate immunity; Nature Reviews Immunology 13,679-692(2013).

In addition to the MEK inhibitor and the p38 inhibitor, the present invention is also directed to a NFκB (NFkB/NFkappaB) inhibitor for use in the methods for the prophylaxis and/or treatment of a co-infection or bacterial infection of the present invention. The determination of whether or not a compound is a NFκB inhibitor is within the skill of one of ordinary skill in the art.

NF-κB (nuclear factor kappa-light-chain-enhancer of activated B cells) is a protein complex that controls transcription of DNA. NF-κB is found in almost all animal cell types and is involved in cellular responses to stimuli such as stress, cytokines, free radicals, ultraviolet irradiation, oxidized LDL, and bacterial or viral antigens. Vertebrate NFκB transcription complexes can be any of a variety of homo- and heterodimers formed by the subunits p50 (NFκB1), p52 (NFκB2), c-Rel, RelA (p65) and RelB (Gilmore TD. (2006) Oncogene 25: 6680-6684). These complexes bind to DNA regulatory sites called κB sites, generally to activate specific target gene expression. In most cell types, NF-κB dimers are located in the cytoplasm in an inactive form through association with any of several IκB inhibitor proteins (IκB α, β, ε, γ, p105 and p100). In response to a wide array of stimuli IκB is rapidly phosphorylated, ubiquitinated and degraded by the proteasome. The freed NF-κB dimer then translocates to the nucleus where it can modulate specific gene expression.

The phosphorylation and degradation of IκB is important for the regulation of NFκB complexes, which is mediated by the IκB kinase (IKK) complex containing two kinase subunits, IKKα and IKKβ, and an associated scaffold-like regulatory protein called NEMO (aka IKKγ) (Gilmore and Herscovich (2006) Inhibitors of NF-κB signaling: 785 and counting Oncogene. 25, 6887-6899). Notably, as for example shown in Example 3 of the present invention, NF-κB siganling is also important for bacterial (such as S. aureus) internalisation into cells.

According to the present invention, the inhibitor may exhibit its regulatory effect upstream or downstream of NFκB or directly on NFκB, with the latter mode of action being preferred. Examples of inhibitors regulating NFκB activity include those where the inhibitor may decrease transcription and/or translation of NFκB, or may shorten the half-life of NFκB. The inhibitor may also reversibly or irreversibly bind NFκB, inhibit its activation, inactivate its activity, or otherwise interfere with its interaction with downstream targets, such as trgets on genes. Also, an NFκB inhibitor can inhibit protein kinases such as molceules which inhibit IkBa phosphorylation by e.g. IKK inhibition. Compounds that have such an activity are SC-893, BMS-345541, which may serve as reference compounds. Also a NFκB inhibitor may inhibit protein phosphatases, or inhibit the proteasome, or ubiquitination. Examples of such NFκB inhibitors, which may also serve as reference compounds include protein tyrosine phosphatase inhibitors, boronate, bortezomib, NPI-0052. Alternatively, a NFκB inhibitor may block the nuclear translocation of NFκB, or its binding to DNA. Examples of such inhibitors include, which may also serve as reference compounds, SN50, dehydroxymethylepoxyquinomicin and NFκB decoy ODNs. Further information on inhibitor of NFκB can be obtained from Gupta et al. (2010) (Gupta et al. (2010) Inhibiting NFκB activation by small molecules as a therapeutic strategy. Biochim Biophys Acta. 1799(10-12): 775-787).

A NFκB inhibitor can be a small molecule, large molecule, peptide, oligonucleotide, and the like. The NFκB inhibitor may be a protein or fragment thereof or a nucleic acid molecule. Also included by the term NFκB inhibitor is a pharmaceutically acceptable salt of the NFκB inhibitor. In one embodiment, the NFκB inhibitor is selected from the group consisting of the inhibitors/molceules as listed in tables 3 and 4 in FIGS. 9 and 10. In another embodiment, the NFκB inhibitor is selected from the group consisting of the inhibitors/molceules as listed in table 3 in FIG. 9. In another embodiment, the NFκB inhibitor is selected from the group consisting of the inhibitors/molceules as listed in table 4 in FIG. 10.

In another embodiment, the NFκB inhibitor is selected from the group consisting of LASAG, SC75741 (and derivatives), MG 132, TPCA-1, PCTC, IMD 0354, Luteolin, Caffeic acid phenethyl ester, Cardamonin, PF 184, IKK 16, SC 514, Withaferin A, Arctigenin, Bay 11-7085, PSI, PR 39, Ro 106-9920, Bay 11-7821, ML-130, Celastrol, Tanshinone IIA, HU 211, Gliotoxin, CID 2858522, Honokiol, Andrographolide, 10Z-Hymenialdisine, ACHP, Pristimerin, Sulfasalazine, ML 120B dihydrochloride, Amlexanox, 9-Methylstreptimidone, N-Stearoyl phytosphingosine, 2-(1,8-naphthyridin-2-yl)-Phenol, 5-Aminosalicylic acid, BAY 11-7085, Ethyl 3,4-Dihydroxycinnamate, Helanalin, NF-κB Activation Inhibitor II, JSH-23, Glucocorticoid Receptor Modulator, CpdA, PPM-18, aspirin (ASA), Pyrrolidinedithiocarbamic acid ammonium salt, (R)-MG132, SC75741 (and derivatives), Rocaglamide, Sodium salicylate, QNZ, PS-1145, CAY10512, bortezomib, salsalate, resveratrol, LASAG, deoxyspergualin, sulindac, thalidomide, AGRO-100, CHS 828 and/or Curcumin, preferably bortezomib, curcumin, salsalate, resveratrol, sodium salicylate, LASAG, ASA, deoxyspergualin, sulindac, thalidomide, AGRO-100, CHS 828 even more preferably SC75741 (and derivatives) ASA and LASAG and most preferably LASAG.

With the term "SC75741" or "SC75741 (and derivates)" in addition to SC75741 also derivates of SC75741 are envisaged by the present invention.

In general a person skilled in the art knows how to find out if a coumpound is an MEK inhibitor, p38 inhibitor and/or NFκB inhibitor. A further example of how one could determine if a compound is a MEK inhibitor and/or p38 inhibitor would be to isolate the MEK and/or p38 NFκB protein. The protein can be isolated from cells where the MEK and/or p38 protein is naturally expressed or where it has been overexpressed by means of transfection of an oligonucleotide or infection with a virus that directs the expression of the MEK and/or p38 protein. Additionally, MEK and/or p38 protein can also be expressed recombinantly. Upon isolating the protein a person of ordinary skill in the art can measure the activity of the kinase in the presence or absence of a potential MEK and/or p38 inhibitor. If the kinase activity is less in the presence than in the absence of an alleged inhibitor, that inhibitor is a MEK and/or p38, respectively.

If acting on MEK and/or p38 directly, the inhibitor should exhibit an IC50 value of about 5 µM or less, preferably 500 nm or less, more preferably 100 nm or less. In a related embodiment, the inhibitor should exhibit an IC50 value relative to the p38-α isoform that is preferably at least ten fold less than that observed when the same inhibitor is tested against other p38 MAP kinase isoforms in the same or comparable assay. It should be noted that IC50 values are assay dependent and may change from determination to determination. It is more important to look at relative relationships of compounds' IC50 values rather than the exact values themselves.

An IC50 is the concentration of compound which inhibits the enzyme to 50% of the activity as measured in the absence of an inhibitor.

IC50 values are calculated using the concentration of inhibitor that causes a 50% decrease as compared to a control. IC50 values are assay dependent and will vary from measurement to measurement. As such, IC50 values are relative values. The values assigned to a particular inhibitor are to be compared generally rather than on an absolute basis.

Samples or assays comprising MAP and/or MAPK kinase that are treated with a potential activator, inhibitor, or modulator are compared to control samples without the inhibitor, activator, or modulator to examine the extent of inhibition. Control samples (untreated with inhibitors) can be assigned a relative MAP and/or MAPK kinase activity value of 100%. Inhibition of MAP and/or MAPK kinase is achieved when the MAP and/or MAPK kinase activity value relative to the control is about 80%, optionally 50% or 25-0%. Activation of MAP and/or MAPK kinase is achieved when the MAP kinase activity value relative to the control is 110%, optionally 150%, optionally 200-500%, or 1000-3000% higher. Exemplary MAP kinase binding activity assays of the present invention are: a MAP and/or MAPK kinase ligand blot assay (Aymerich et al., Invest Opthalmol Vis Sci. 42:3287-93, 2001); a MAP and/or MAPK kinase affinity column chromatography assay (Alberdi et al., J Biol Chem. 274:31605-12, 1999) and a MAP and/or MAPK kinase ligand binding assay (Alberdi et al., J Biol Chem. 274:31605-12, 1999). Each incorporated by reference in their entirety.

Also the selectivity of the inhibitors may be measured by a kinase selectivity assay is described in Mihara (2008), Br. J. Pharmacol. 154(1):153-164.

In the case of the NFκB inhibitor one can measure for example the gene products (proteins) of target genes of NFκB in a non-treated control cell and compare the expression of these target gene products to a cell, which has been treated with a NFκB Inhibitor. Some target genes are described in Oeckinghaus and Ghosh (2009) The NF-κB Family of Transcription Factors and Its Regulation. Cold Spring Harb Perspect Biol. October 2009; 1(4): a000034.

The expression level is reduced, when the cell treated with the inhibitor. Other strategies may be to detect IkBa degradation together with p-p65 accumulation and nuclear translocation of NFκB by Westernblot. Also NFκB interactions with DNA of cells not treated with an inhibitor compared to cells that have been treated with an inhibitor may be analysed by using an electrophoretic mobility shift assay (EMSA).

The inhibitory properties of a molecule can also be analysed by comparing its action to a reference compound. A "reference compound" as referred to herein means a compound, which may be used as a positive control for the determination if a molecule has MEK inhibitor, p38 inhibitor and/or NFκB inhibitor properties. As such also any of the inhibitors listed herein may be used as such a reference compound. A possible test may be one in which cells, which are e.g. stimulated to activate the MEK, p38 and or NFκB pathway are treated with a reference compound and in parallel e.g. in a different well with a compound of interest.

The inhibitors of the present invention can be used in a method for treating and/or prophylaxis. As such the term "treating" or "treatment" includes administration of a MEK inhibitor, p38 Inhibitor, and/or NFκB inhibitor preferably in the form of a medicament, to a subject suffering from a coinfection comprising a bacterial infection and an influenza virus infection for the purpose of ameliorating or improving symptoms. Similarly included is the administration of a MEK inhibitor, p38 Inhibitor, and/or NFκB inhibitor preferably in the form of a medicament, to a subject suffering from a bacterial infection for the purpose of ameliorating or improving symptoms.

Furthermore, the terms "prophylaxis" as used herein, refers to any medical or public health procedure whose purpose is to prevent a disease. As used herein, the terms "prevent", "prevention" and "preventing" refer to the reduction in the risk of acquiring or developing a given condition, namely a coninfection comprising an influenza virus infection and a bacterial infection or a bacterial infection alone. Also meant by "prophylaxis" is the reduction or inhibition of the recurrence of a coninfection comprising an influenza virus infection and a bacterial infection or a bacterial infection alone in a subject.

The inhibitors of the present invention are effective in treating a coinfection. A "co-infection" as used herein comprises an influenza virus infection and a bacterial infection. Such a coinfection can take place by simultaneous infection of a host e.g. a subject and/or single cell with a bacterium and an influenza virus. It can also be that a host e.g. a subject and/or cell is simultaneously infected with one or more viral particles and one or more bacteria. However, such a coinfection can also take place sequentially. In such a case is firstly infected with one or more viral particles and later in time the same host and/or cell becomes infected with one or more bacteria or vice versa. The time period between the two infections can be a time period of at most 14 days, 13 days, 12 days, 11 days, 10 days, 9 days, 8 days, 7 days, 6 days, 5 days, 4 days, 3 days, 2 days, 1 day, 12 hours, 6 hours, 3 hours, 1.5 hours or at minimum 30 minutes.

Such a situation may also be a superinfection, in which a second infection is superimposed on an earlier one especially by a different microbial agent of exogenous or endogenous origin that is resistant to the treatment used against the first infection.

Within the co-infection the influenza virus infection can be mediated by influenza A virus or influenza B virus, preferably the influenza A virus is H1N1, H2N2, H3N2, H6N1, H7N7, H7N9, H9N2 H10N7, H10N8 or H5N1. In one embodiment, the influenza A virus is H1N1. In other embodiments, the influenza A virus is H3N2, H5N1 and H7N9. In additional embodiments, the influenza A virus is H3N2, H5N1, H1N1 and H7N9.

The present invention also relates to a "bacterial infection" which can take place in the setting of a co-infection described above or can occur as the only infection present in a host e.g. a subject and/or cell. The bacterial infection can be mediated by any bacterium, preferably it is mediated by a bacterium selected from the group consisting of *Staphylococcaceae*, *Streptococcaceae*, *Legionellaceae*, *Pseudomonadaceae*, *Chlamydiaceae*, *Mycoplasmataceae*, *Enterobacteriaceae*, *Pseudomonadales* and/or *Pasteurellaceae*.

In other embodiments the bacterial infection is mediated by a bacterium selected from the group consisting of *Staphylococcus*, preferably *Staphylococcus aureus*, methicillin sensitive and methicillin resistant *Staphylococcus aureus*, Panton-Valentine leukocidin (PVL)-expressing *Staphylococcus aureus* and/or *Streptococcaceae*, preferably *Streptococcus mitis*, *Streptococcus pyogenes* or *Streptococcus pneumonia*, *Legionella*, preferably *Legionella pneumophila*, *Pseudomonas*, preferably *Pseudomonas aeruginosa*, *Chlamydophila*, preferably *Chlamydophila pneumonia*, *Mycoplasma*, preferably *Mycoplasma pneumonia*, *Klebsiella*, preferably *Klebsiella pneumonia*, *Moraxella*, preferably *Moraxella catarrhalis* and/or *Haemophilus*, preferably *Haemophilius influenza*. Preferably the bacterium is selected from the group consisting of *Staphylococcus aureus*, *Streptococcus pneumonia* or *Haemophilius influenza*. Most preferably the bacterium is *Staphylococcus aureus*.

It is also envisaged by the present invention that the inhibitors can be combined with each other. As such in one embodiment the MEK inhibitor is combined with another MEK inhibitor, the p38 inhibitor and/or the NFκB inhibitor. In further embodiments, the p38 inhibitor is combined with another p38 inhibitor, the MEK inhibitor and/or the NFκB inhibitor. In another embodiment the NFκB inhibitor is combined with another NFκB inhibitor, the p38 inhibitor and/or the MEK inhibitor. With repspect to the above, the term "another inhibitor" is used to clarify that e.g. one MEK inhibitor can also be combined with another MEK inhibitor, while these two MEK inhibitors are not the same. E.g. the MEK inhiboitor CI-1040 can be combined with the MEK inhibitor GDC-0973. This equally relates to the p38 and NFκB inhibitors.

In one embodiment, the MEK inhibitor, the p38 inhibitor and/or the NFκB inhibitor is/are administered contemporaneously, previously or subsequently to the one or more additional inhibitors targeting the influenza virus and the bacterium.

In further embodiments, the MEK inhibitor, p38 inhibitor and/or NFκB inhibitor is/are for use in the methods for the prophylaxis and/or treatment of a co-infection of the present invention, wherein the MEK inhibitor, the p38 inhibitor and/or the NFκB inhibitor are combined with one or more inhibitors targeting the influenza virus and/or the bacterium. In one embodiment, the MEK inhibitor, the p38 inhibitor and/or the NFκB inhibitor is/are administered contemporaneously, previously or subsequently to the one or more inhibitors targeting the influenza virus and/or the bacterium.

In general, an inhibitor targeting the influenza virus is any inhibitor or medicament effective in influenza therapy. Different substances are known to be effective in reducing an influenza infection. Among them are for example neuraminidase inhibitors, compounds targeting an ion channel protein (M2) and compounds targeting polymerase or endonuclease activity via interfering with a component of the viral polymerase complex, PB1, PB2, PA or NP. By the invention also pharmaceutically acceptable salts of these inhibitors are envisoned.

A "neuraminidase inhibitor" is an antiviral drug targeted at influenza virus, which works by blocking the function of the viral neuraminidase protein, thus preventing the virus from binding to a cell it aims to infect and/or preventing the virus from reproducing by budding from the host cell, since the newly produced viruses cannot bud off from the cell in which they have replicated. Also comprised are pharmaceutically acceptable salts of a neuraminidase inhibitor. Preferred neuraminidase inhibitors are oseltamivir, zanamivir, peramivir, or a pharmaceutically acceptable salt of any of these substances, such as oseltamivir phosphate, oseltamivir carboxylate, etc. Most preferred neuraminidase inhibitors are oseltamivir phosphate, zanamivir, oseltamivir or peramivir.

Compounds targeting an ion channel protein (M2) are for example amantadine and/or rimantadine, while compounds targeting polymerase or endonuclease activity via interfering with a component of the viral polymerase complex, PB1, PB2, PA or NP are for example the NP blocker Nucleozin or the polymerase inhibitor T-705.

Alternatively or additionally, the MEK inhibitor, p38 inhibitor and/or NFκB inhibitor can be combined with one or more inhibitors targeting the bacterium. An inhibitor targeting the bacterium can be any inhibitor effective in reducing bacterial infection. A preferred inhibitor, well known to the skilled artesian is an antibiotic. Preferred antibiotics can be obtained from table 5 (FIG. 11). Thus, in one embodiment, the antibiotic is selected from the group consisting of the antibiotics as listed in table 5 (FIG. 11). In a further embodiment, the antibiotic is selected from the group consisting of the class of antibiotics as listed in table 5 (FIG. 11). In another embodiment, the antibiotic is selected from the group consisting of the generic name of the antibiotics as listed in table 5 (FIG. 11). More preferred are antibioics selected from Gentamicin, Rifampicin, Lysosthaphin, Erythromycin, Levofloxacin, Vancomycin, Teicoplanin, Penicillin and Oxacillin.

The "subject", which may be treated by the inhibitors or combinations of inhibitors of the present invention preferably, is a vertebrate. In the context of the present invention the term "subject" means an individual in need of a treatment of a co-infection or a bacterial infection alone. Preferably, the subject is a patient suffering from a co-infection or a bacterial infection alone or being at a risk thereof. Preferably, the patient is a vertebrate, more preferably a mammal. Mammals include, but are not limited to, farm animals, sport animals, pets, primates, mice and rats. Preferably, a mammal is as a human, dog, cat, cow, pig, mouse, rat etc., particularly preferred, it is a human. In some embodiments, the subject is a human subject, which optionally is more than 1 year old and less than 14 years old; between the ages of 50 and 65, or older than 65 years of age. In other embodiments the the subject is a human subject, which is selected from the group consisting of subjects who are at least 50 years old, subjects who reside in chronic care facilities, subjects who have chronic disorders of the pulmonary or cardiovascular system, subjects who required regular medical follow-up or hospitalization during the preceding year because of chronic metabolic diseases, renal dysfunction, hemoglobinopathies, or immunosuppression, subjects with less than 14 years of age, subjects between 6 months and 18 years of age who are receiving long-term aspirin therapy, and women who will be in the second or third trimester of pregnancy during the influenza season.

In the method of the invention, the MEK inhibitor, p38 inhibitor or NFκB inhibitor as well as the inhibitor targeting the influenza virus and the inhibitor targeting the bacterium may be administered orally, intravenously, intrapleurally, intramuscularly, topically or via inhalation. Preferably, the MEK inhibitor is administered via nasal inhalation or orally.

The present invention also envisages different compositions. The present invention relates to a composition comprising a MEK inhibitor, a p38 inhibitor and/or a NFκB inhibitor for use in a method for the prophylaxis and/or treatment of a co-infection comprising a bacterial infection and an influenza virus infection. The present invention similarly relates composition comprising a MEK inhibitor, a p38 inhibitor and/or a NFκB inhibitor for use in a method for the prophylaxis and/or treatment of a bacterial infection. Also provided for by the present invention is a composition comprising a MEK inhibitor, a p38 inhibitor and/or a NFκB inhibitor and one or more inhibitors targeting the influenza virus and/or the bacterium for use in a method for the prophylaxis and/or treatment of a co-infection comprising a bacterial infection and an influenza virus infection. In addition, the present invention relates to a composition comprising a MEK inhibitor, a p38 inhibitor and/or a NFκB inhibitor and one or more inhibitors targeting the the bacterium for use in a method for the prophylaxis and/or treatment of a bacterial infection.

The composition comprising the MEK inhibitor, the p38 inhibitor and/or the NFκB inhibitor and additionally eventually one or more inhibitors targeting the the bacterium and/or one or more inhibitors targeting the influenza virus may be a pharmaceutical composition. Preferably, such compositions further comprise a carrier, preferably a pharmaceutically acceptable carrier. The composition can be in the form of orally administrable suspensions or tablets; nasal sprays, sterile injectable preparations (intravenously, intrapleurally, intramuscularly), for example, as sterile injectable aqueous or oleaginous suspensions or suppositories. When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art. The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The inhibitor or inhibitors are preferably administered in a therapeutically effective amount.

The pharmaceutical composition for the use of the invention and comprising a MEK inhibitor, a p38 inhibitor and/or a NFκB inhibitor and optionally one or more inhibitors targeting an influenza virus and/or one or more inhibitors targeting a bacterium is administered to a patient which is a mammal or a bird. Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human, with human being preferred. Examples of suitable birds include, but are not limited to, a turkey, a chicken, a goose, a duck, a teal, a mallard, a starling, a Northern pintail, a gull, a swan, a Guinea fowl or water fowl to name a few. Human patients are a particular embodiment of the present invention.

The "therapeutically effective amount" for each active compound/inhibitor can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, adverse events, and the like, as will be apparent to a skilled artisan. The amount of administration can be adjusted as the various factors change over time.

The inhibitors, methods and uses described herein are applicable to both human therapy and veterinary applications. The compounds described herein, in particular, MEK inhibitor, a p38 inhibitor and/or a NFκB inhibitor and optionally one or more inhibitors targeting an influenza virus and/or one or more inhibitors targeting a bacterium having the desired therapeutic activity may be administered in a physiologically acceptable carrier to a subject, as described herein. Depending upon the manner of introduction, the compounds may be formulated in a variety of ways as discussed below. The concentration of therapeutically active compound in the formulation may vary from about 0.1-100 wt %. The agents maybe administered alone or in combination with other treatments.

The pharmaceutical compounds in the method of present invention can be administered in any suitable unit dosage forms. Suitable oral formulations can be in the form of tablets, capsules, suspension, syrup, chewing gum, wafer, elixir, and the like. Pharmaceutically acceptable carriers such as binders, excipients, lubricants, and sweetening or flavoring agents can be included in the oral pharmaceutical compositions. If desired, conventional agents for modifying tastes, colors, and shapes of the special forms can also be included.

For injectable formulations, the pharmaceutical compositions can be in lyophilized powder in admixture with suitable excipients in a suitable vial or tube. Before use in the clinic, the drugs may be reconstituted by dissolving the lyophilized powder in a suitable solvent system to form a composition suitable for intravenous or intramuscular injection.

In accordance with another embodiment of the present invention, a pharmaceutical composition is provided, comprising a therapeutically effective amount of a a MEK inhibitor, a p38 inhibitor and/or a NFκB inhibitor as well as a therapeutically effective amount of a neuraminidase inhibitor chosen from the group of oseltamivir, oseltamivir phosphate, zenamivir and peramivir.

In one embodiment, the composition can be in an orally administrable form (e.g., tablet or capsule or syrup etc.) with a therapeutically effective amount (e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg) of a MEK inhibitor, a p38 inhibitor and/or a NFκB inhibitor and a therapeutically effective amount (e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg) of neuraminidase inhibitor as described above.

In further embodiments, the MEK inhibitor, p38 inhibitor and/or NFκB inhibitor is/are for use in the methods for the prophylaxis and/or treatment of a co-infection of the present invention, wherein the MEK inhibitor, the p38 inhibitor and/or the NFκB inhibitor reduces both the viral and bacterial infection, when contacting it/them with an in vitro test system, wherein the test system comprises cultured cells infected with
a) an influenza virus and
b) a bacterium
when compared to the in vitro test system before the contacting. In another embodiment, the MEK inhibitor, p38 inhibitor and/or NFκB inhibitor is/are for use in the methods for the prophylaxis and/or treatment of a bacterial infection of the present invention, wherein the MEK inhibitor, the p38 inhibitor and/or the NFκB inhibitor reduces the bacterial infection, when contacting it/them with an in vitro test system, wherein the test system comprises cultured cells infected with a bacterium, when compared to the in vitro test system before the contacting.

As such the present invention also relates to an in vitro test system, wherein the test system comprises cultured cells infected with
a) an influenza virus and
b) a bacterium.

Along this line, the present invention also provides for an in vitro test system, wherein the in vitro test system comprises cultured cells infected with a bacterium.

In the cases where the in vitro test system includes a viral and bacterial infection, again, these infections can be taking place sequentially or simultaneously.

A "cultured cell" or "cultured cells" is/are cells, which are not present in their natural environment e.g. within a plant or animal. Rather a cultured cell may be a primary cell culture, which comprises cells isolated from their natural environment, or a cell line. Preferably the cultured cells are human lung epithelial cells. Preferably, the cultured cells are seeded at a density of about $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $10 \times 10^5$, $11 \times 10^5$ most preferably $8 \times 10^5$ cells in 0.5 ml, 1 ml, 1.5 ml, 2 ml, 2.5 ml, 3 ml, 3.5 ml, 4 ml medium such as DMEM. Most preferred is a density of $8 \times 10^5$ cells per in 2 ml DMEM.

Such cultured cells are infected with a virus and a bacterium or in other embodiments with a bacterium alone. As already described above, a co-infection can take place in a sequential or simultaneous manner. For example the cultured cells may be infected first with the influenza virus and 30 minutes later with bacterium/bacteria. It is also possible to additionally add an antibiotic to the culture after 3 hours, to remove extracellular bacteria. In such a scenario the antibioticum would then become washed off again. In other embodiments, the cells are only infected with a bacterium.

The term "contacting" as used herein refers to the bringing of a cell comprising an influenza virus and a bacterium spatially into close proximity to a MEK inhibitor, a p38 inhibitor and/or a NFκB inhibitor.

This can for example mean that an inhibitor is applied to the medium in which the cultured cells are located via a syringe.

Upon contacting then, if the inhibitor is active, the viral infection as well as the bacterial infection becomes reduced. In some embodiments, again, the inhibitor of the present invention is used to reduce only a bacterial infection in the absence of an influence virus infection.

In one embodiment, the reduction of the viral infection is a reduction in plaque forming units (pfu)/ml and the reduction in the bacterial infection is a reduction in colony forming units (CFU)/ml. The "plaque forming units (pfu)/ml" is a measure of the number of particles capable of forming plaques per unit volume, such as virus particles. It is a functional measurement rather than a measurement of the absolute quantity of particles: viral particles that are defective or which fail to infect their target cell will not produce a plaque and thus will not be counted. For example, a solution of influenza virus with a concentration of 1,000 PFU/µl indicates that 1 µl of the solution contains enough virus particles to produce 1000 infectious plaques in a cell monolayer. In the case of the present invention, a cell culture treated with an inhibitor shows a reduced number of plaque forming units in a culture after the treatment, when compared to a culture before the treatment with an inhibor of the present invention.

A possible "reduction in plaque forming units (pfu)/ml" is analysed in the following way. First the cultured cells, which are co-infected with an influenza virus and a bacterium are analysed for their ability to generate plaque forming units (pfu)/ml by e.g. sucking of some cells from the petridish and plating them for counting the bacterial plaques that will form. This result is then compared to the number of plaque forming units (pfu)/ml generated by cells of the same culture after the inhibitor was applied. If the number of the plaque forming units (pfu)/ml is reduced after the treatment with an inhibitor compared to the number generated before the application of the inhibitor, there is a reduction in the plaque forming units.

The "colony forming units (CFU)/ml" estimates the number of viable bacteria in a sample. Different methods exist. For example to generate colony forming units a sample (e.g. cultured cells in a small volume) are spread across the surface of a nutrient agar plate and allowed to dry before incubation for counting. A viable bacterium is defined as the ability to multiply via binary fission under the controlled conditions. The visual appearance of a colony in a cell culture requires significant growth—when counting colonies it is uncertain if the colony arose from one cell or 1,000 cells. Therefore results are reported as CFU/ml (colony-forming units per milliliter) for liquids, and CFU/g (colony-forming units per gram) for solids to reflect this uncertainty (rather than cells/ml or cells/g).

"Colony forming units (CFU)/ml" can be analysed in the following way. First the cultured cells, which are co-infected with an influenza virus and a bacterium or with a bacterium alone are analysed for their ability to generate colony forming units (CFU)/ml by e.g. sucking of some cells from the petridish and plating them for counting. This result is then compared to the number of colony forming units (CFU)/ml generated by cells of the same culture after the inhibitor was applied. If the number of the colony forming units (CFU)/ml is reduced to the number generated before the application of the inhibitor, there is a reduction.

In general the person skilled in the art knows these well known techniques of analyzing bacterial and viral infections. How one can measure the plaque forming units (pfu)/ml and the colony forming units (CFU)/ml is further described in the literature (Tuchscherr, L. et al. (2011). *Staphylococcus aureus* phenotype switching: an effective bacterial strategy to escape host immune response and establish a chronic infection (EMBO molecular medicine 3, 129-141 and Hrincius, E.R et al. (2010) CRK adaptor protein expression is required for efficient replication of avian influenza A viruses and controls JNK mediated apoptotic responses. Cellular microbiology 12, 831-843).

In addition the present invention relates to the following items:

Item 1. The invention also provides for the use of the in vitro test system of of the present invention for the determination of inhibitors effective in reducing a coinfection comprising a bacterial infection and an influenza virus infection. In one embodiment, the reduction of the viral infection is a reduction in plaque forming units (pfu)/ml and the reduction in the bacterial infection is a reduction in colony forming units (CFU)/ml.

Item 2. In addition the present invention relates to a method for detecting molecules effective in the prophylaxis and/or treatment of a co-infection comprising a bacterial infection and an influenza virus infection comprising contacting the in vitro test system of the present invention with a compound of interest, wherein the compound of interest reduces both the viral and bacterial infection, compared to the in vitro test system before the contacting. In one embodiment, the reduction of the viral infection is a reduction in plaque forming units (pfu)/ml and the reduction in the bacterial infection is a reduction in colony forming units (CFU)/ml.

Item 3. The present invention, in addition, relates to a use of the in vitro test system of the present invention for the determination of inhibitors effective in reducing a bacterial infection.

Item 4. Furthermore, the present invention relates to the use of the in vitro test systems of the present invention for the examination of innate host cell responses, which optionally includes examination of the level of signal transduction, resulting cytokine and chemokine expression, induction of apoptosis and necrosis and/or redox hemostasis regulating health and disease.

Item 5. Also provided for by the present invention is a method for detecting molecules effective in the prophylaxis and/or treatment a bacterial infection comprising contacting the in vitro test system of the present invention with a compound of interest, wherein the compound of interest reduces the bacterial infection, compared to the in vitro test system before the contacting.

Item 6. The present invention furthermore relates to a cultured cell infected with an influenza virus and a bacterium.

Item 7. Also provided for is a cultured cell infected with a bacterium.

Item 8. The present invention also relates to a method for the prophylaxis and/or treatment of a co-infection comprising a bacterial infection and an influenza virus infection in a subject, comprising administering a therapeutically effective amount of a MEK inhibitor, a p38 inhibitor and/or a NFκB inhibitor of the present invention or a pharmaceutical composition of the present invention to said subject.

Item 9. Also the present invention provides for a use of a MEK inhibitor, a p38 inhibitor and/or a NFκB inhibitor of the present invention or a composition of the present invention for the preparation of a medicament.

Item 10. In addition the present invention relates to a use of a MEK inhibitor, a p38 inhibitor and/or a NFκB inhibitor of the present invention or a composition of the present invention for the prophylaxis and/or treatment of a co-infection comprising a bacterial infection and an influenza virus infection.

Item 11. Similarly, the present invention also provides for a method for the prophylaxis and/or treatment of a bacterial infection in a subject, comprising administering a therapeutically effective amount of a MEK inhibitor, a p38 inhibitor and/or a NFκB inhibitor of the present invention or a pharmaceutical composition of the present invention to said subject.

Item 12. In addition the present invention relates to a use of a MEK inhibitor, a p38 inhibitor and/or a NFκB inhibitor of the present invention or a composition of the present invention for the prophylaxis and/or treatment of a bacterial infection.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

EXAMPLES

The following examples illustrate the invention. These examples should not be construed as to limit the scope of this invention. The examples are included for purposes of illustration and the present invention is limited only by the claims.

Example 1

Within the last years the need for additional and alternative therapeutic strategies apart from vaccination or treatment with conventional antivirals against IV (neuraminidase and M2 blockers) and conventional antibiotics against S. aureus steadily increased. In meantime for antiviral intervention several cellular factors have been identified as potential targets. In quite contrast, the knowledge about the rote of cellular factors during bacterial infection and in particular as targets for antibacterial treatment either by reduction of bacterial amount and/or onset of accelerating cytokine expression is less understood, even more in presence of IV co-infection.

We established an infection protocol that allows determination of (1) progeny virus titers and (2) titers of intracellular bacteria as well as (3) changes in host defense mechanisms in presence or absence of potential antiinfectives upon IV and S. aureus co-infection. In an initial approach we investigated the effect of the MEK inhibitor (U0126=50 µM), the p38 inhibitor (SB202190=10 µM) and the NFκB inhibitor (LASAG=5 mM) in comparison to a solvent control against IV and S. aureus infection in a singular or co-infection situation. As a control the viral neuraminidase inhibitor Oseltamivir (Tamiflu) (2 µm) was used in comparison to Hepes. For virus infection we used the human influenza virus A/Puerto Rico/8134 (H1N1) or the avian influenza virus A/FPV/Bratislava/79 (H7N7) and for bacterial infection we used the S. aureus strain 6850. Procedure of infection (FIG. 1): Human lung epithelial cells were seeded in 6-well plates ($8\times10^5$ cells/well) in 2 ml DMEM [10% FCS]. 16-20 hrs after seeding, cells were rinsed and incubated with PBS/BA [0.2% bovine serum albumin (BSA), 1 mM $MgCl_2$, 0.9 mM $CaCl_2$, 100 U/ml penicillin, 0.1 mg/ml streptomycin] (500 µl per 6 well) or PBS/BA containing the virus at the indicated multiplicity of infection (MOI) at 37° C. After 30 min incubation, the virus dilution was aspirated, cells were rinsed with PBS and supplemented with invasion medium DMEM/INV [1% human serum albumin, 25 nmol/l HEPES] (2 ml per 6 well) with or without bacteria at the MOI indicated in presence or absence of the test compound. 3 hrs post bacterial infection cells were treated with antibiotics to remove extracellular bacteria. Therefore cells were rinsed with PBS and subsequently incubated with DMEM/INVantibiotics [2 µg/ml lysostaphin (Sigma)] (1 ml per 6 well) for 20 min at 37° C. After an additional wash with PBS cells were supplemented with DMEM/INV containing the testsubstance and were incubated for the times indicated at 37° C. Upon A/Puerto Rico/8/34 DMEM/INV was additionally supplemented with 0.333 µg/ml Trypsin (Invitrogen). Determination of IV titers and intracellular bacteria were performed as described in (Hrincius et al., 2010, Tuchscherr et al., 2011).

IV titers are depicted as plaque forming units (pfu)/ml and S. aureus titers are depicted as colonie forming untits (CFU)/ml. Data represent the means±SD of two to three independent experiments with two biological samples. Statistical significance was evaluated by a two-tailed two sample t-test ($*p<0.05;p<0.01;*p<0.001$).

Figure 2:
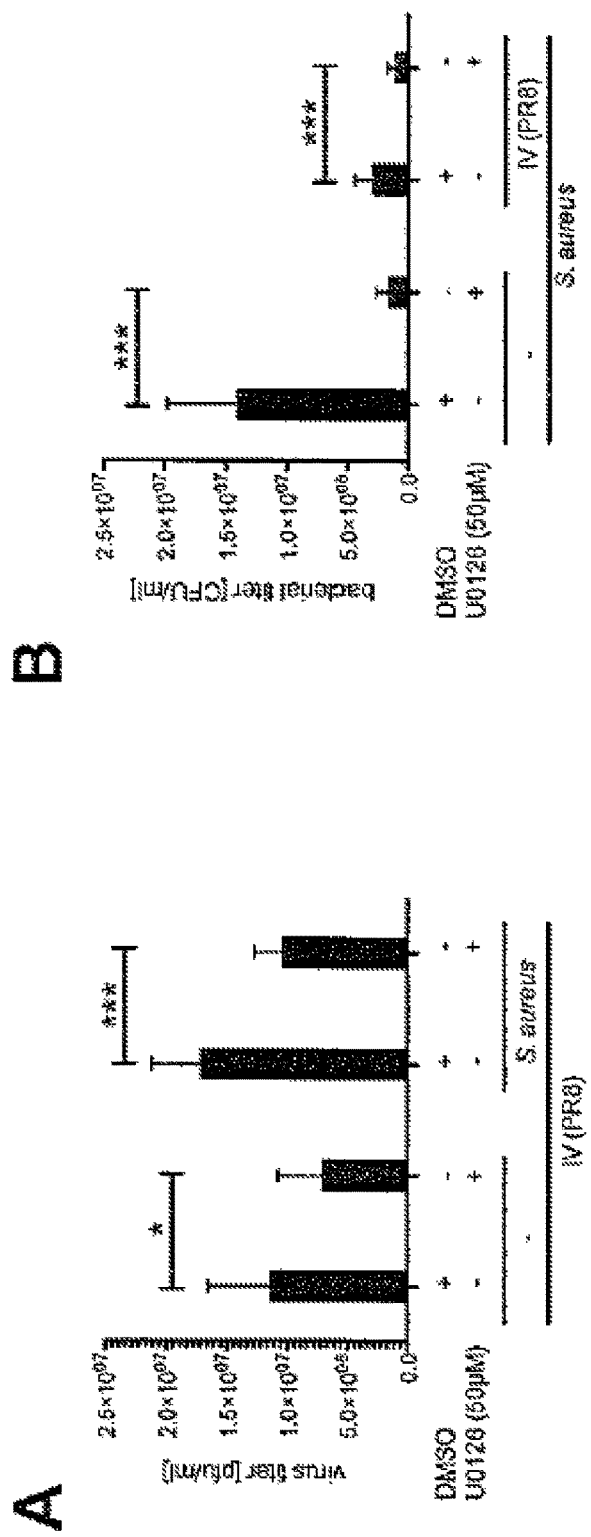
FIG. 2: The MEK inhibitor U0126 reduces IV titers (A/Puerto Rico/8/34) and S. aureus load, even in a co-infection situation. Human lung epithelial cells were seeded in 6-well plates ($8\times10^5$ cells/well) in 2 ml DMEM [10% FCS]. 16 -20 hrs after seeding, cells were rinsed and incubated with PBS/BA [0.2% bovine serum albumin (BSA), 1 mM $MgCl_2$, 0.9 mM $CaCl_2$, 100 U/ml penicillin, 0.1 mg/ml streptomycin] (500 µl per 6 well) or PBS/BA containing the influenza virus A/Puerto Rico/8/34 at a multiplicity of infection (MOI=0.1) at 37° C. After 30 min incubation, the virus dilution was aspirated, cells were rinsed with PBS and supplemented with Invasion medium DMEM/INV [1% human serum albumin, 25 nmol/l HEPES] (2 ml per 6 well) with or without S. aureus 6850 (MOI=0.5) in presence of 50 µM U0126 or DMSO (solvent control). 3 hrs post bacterial infection cells were treated with antibiotics to remove extracellular bacteria. Therefore cells were rinsed with PBS and subsequently incubated with DMEM/INVantibiotics [2 µg/ml lysostaphin (Sigma)] (1 ml per 6 well) for 20 min at 37° C. After an additional wash with PBS cells were supplemented with DMEM/INV containing 50 µM U0126 or DMSO and 0.333 µg/ml Trypsin (Invitrogen). After an incubation period of further 14 hrs at 37° C. IV titers and intracellular bacteria were determined as described in (Hrincius et al., 2010, Tuchscherr et al., 2011).

In a co-infection situation the presence of S. aureus affected IV replication and the presence of IV affected the intracellular amount of S. aureus levels, respectively, due to changes in innate immune responses as well as autophagic and apoptotic mechanisms. Nonetheless, as expected we observed inhibitory effects of U0126 (FIG. 2, 3), SB202190 (FIG. 4) and LG-ASA (FIG. 5) on IV replication. Interestingly, viral titers were also reduced upon treatment with these inhibitors in presence of S. aureus. Furthermore, we were agreeably surprised when intracellular amounts of S. aureus were reduced in presence of U0126, SB202190 or LG-ASA independent from the absence or presence of IV.

Another, amazing observation concerned bacterial replication in presence of U0126 (50 µM ). When *S. aureus* was cultivated over night at 37° C. in DMEM/INV without living cells, bacterial titers were already reduced, but to the same degree than during infection of cells, indicating the dependence of bacteria from a cellular factor (FIG. 2E).

As control we investigated viral titers and intracellular bacterial amounts upon application of the viral neuraminidase inhibitor Oseltamivir (Tamiflu) (FIG. 6). While IV titers were significantly reduced in absence or presence of *S. aureus*, intracellular bacterial amounts were rather increased.

The results demonstrate the great potential of substances targeting cellular factors as antiinfectives against IV and *S. aureus* co-infection, rather than substances against the pathogen itself.

Example 2

In further experiments the effect of the MEK inhibitor U0126, CI-1040 and Cobimetinib (GDC-0973) in comparison to a solvent control against influenza A virus (IAV) and *S. aureus* 6850 infection in a singular or co-infection situation were investigated.

The co-infection procedure is depicted in FIG. 12. To examine the viability of human lung epithelial cells in our experimental setting, cell morphology was monitored 18 hrs upon infection by light microscopy (FIG. 13), the time at which the pathogen load was determined (FIG. 14).

As visible in FIG. 13 singular infection with *S. aureus* 6850 (6850), the influenza virus strains A/FPV/Bratislava/79 (H7N7) (FPV) or A/Wisconsin/67/2005 (H3N2), as well as the co-infection resulted in slight but clearly detectable cell damage. In presence of U0126 (50 µM ) the cell layer appeared much less damaged.

The effect of the MEK inhibitor U0126 (50 µM ) against influenza virus replication A/FPV/Bratislava/79 (H7N7) (FPV) or A/Wisconsin/67/2005 (H3N2) in comparison to a solvent control was determined in human lung epithelial cells in a singular or co-infection situation (FIG. 14).

Inhibition of MEK/ERK signalling resulted in a significant reduction of virus titers upon infection with the IAV subtypes H7N7 and H3N2 in a singular infection situation (FIG. 14). Virus titers were reduced in a co-infection situation in the presence of U0126, too, up to significant levels in H7N7/*S. aureus* co-infected cells (FIG. 14).

Furthermore, the effect of the MEK inhibitor U0126 (50 µM ) against internalized *S. aureus* 6850 was analysed (FIG. 15A, C). In this experimental setting bacterial titers were only slightly decreased in presence of the inhibitor.

To further investigate the effect of U0126 on bacterial growth in general, a cell-free over-night culture of *S. aureus* 6850 was supplemented with different amounts of U0126 (10 µM and 50 µM ) or solvent (FIG. 15B, D). Bacterial growth was inhibited in presence of U0126 in a concentration dependent manner, in comparison to the solvent control (FIG. 15B, D).

Since pro-inflammatory cytokine- and chemokine expression contributes to severe inflammation and tissue damage, the mRNA synthesis of respective chemokines, such as CCL3, also known as macrophage inflammatory protein 1α (MIP1α) and CCL5, also known as RANTES were analysed by qRT-PCR in an infection experiment in presence or absence of U0126 (50 µM ) (FIG. 16A, B). The IAV-induced CCL3 mRNA synthesis, which was increased in presence of *S. aureus* 6850 , was reduced in presence of U0126. Similarly, the IAV-induced CCL5 mRNA synthesis, which was reduced in presence of *S. aureus*, was further reduced in presence of U0126 (50 µM ).

In western-blot analysis the inhibitory effect of U0126 on MEK/ERK signalling was verified by use of a phosphospecific ERK1/2 antibody (FIG. 16C). Furthermore, a reduction of viral protein synthesis (PB1) was observed in presence of upon inhibition of MEK/ERK signalling.

To verify the anti-pathogen potential of U0126 in an in vivo mouse model, influenza virus-infected mice were left untreated or treated with U0126 daily and super-infected with *S. aureus* 6850 (FIG. 17). The administration of U0126 led to a reduction in bacterial titers in vivo independent of viral titers. The fail of reduced virus titers might be explained by the late administration of U0126 at a time point when virus titers are already decreasing in the infection course. Former experiments have indicated that the inhibitor has a higher inhibitory effect, when it is given before influenza virus infection. Nonetheless, the bacterial titers were significantly reduced upon application of U0126.

Within other approaches the effect of the MEK inhibitor CI-1040 (10 µM ) against influenza virus replication A/FPV/Bratislava/79 (H7N7) (FPV) or A/Puerto Rico/8/34 (H1N1) in comparison to a solvent control was determined in human lung epithelial cells in a singular or co-infection situation (FIG. 18).

Inhibition of MEK/ERK signalling by CI-1040 resulted in a reduction of virus titers upon infection with the IAV subtypes H7N7 and H1N1 in a singular and co-infection situation (FIG. 18).

To further investigate the effect of CI-1040 on bacteria growth in general, a cell-free over-night culture of *S. aureus* 6850 was supplemented with different amounts of CI-1040 (1 µM and 10 µM ) or solvent (FIG. 19A, B). Bacterial growth was slightly inhibited in presence of CI-1040 in a concentration dependent manner, in comparison to the solvent control (FIG. 19A, B).

To verify the anti-pathogen potential of another MEK inhibitor, Cobimetinib was tested in an in vivo mouse model, influenza virus-infected mice were left untreated or treated daily with Cobimetinib and were super-infected with *S. aureus* 6850 (FIG. 20). The administration of Cobimetinib led to a slight but clearly detectable reduction in viral and bacterial titers in vivo. Since it has been shown recently that the maximal tolerated dose of Cobimetinib is 30 mg/kg/day. Thus, the inhibitory effect might be improved by higher dosages than used in the present experiment (10 mg/kg/day), which was far less from the maximal tolerated dosage.

In conclusion, the results show different MEK inhibitors as potential anti-IAV/*S. aureus* substances.

Example 3

In further experiments the effect of the NFκB-inhibitor LG-ASA (LASAG) against influenza A virus (IAV) and *S. aureus* 6850 infection in a singular or co-infection situation were investigated.

The co-infection procedure is depicted in FIG. 21 (upper part). To examine the viability of human lung epithelial cells upon infection in absence and presence of LG-ASA (5 mM) cell morphology was monitored 18 hrs upon infection by light microscopy (FIG. 21). While infection with IAV and/or *S. aureus* in absence of LG-ASA (left panel) results in cell destruction, cell morphology was improved in presence of LG-ASA (right panel).

The effect of the NFκB-inhibitor LG-ASA (5 mM) against influenza virus replication A/Puerto Rico/8/34 (H1N1) was determined in human lung epithelial cells in a singular or co-infection situation (FIG. 22/23) 8 h (FIGS. 22/23 A, B, E, F) and 18 h (FIG. 22/23 C, D, G, H) post infection. Two different S. aureus strains were used for infection (a) S. aureus SH1000 (FIG. 22/23 A-D) and (b) S. aureus 6850 (FIG. 22/23 E-H).

While IAV replication was reduced in presence of LG-ASA 8 h and 18 h upon infection, a reduction of bacterial titers was only visible 18 h p.i. In FIG. 22 the results are depicted in a linear scale. To better visualize the pathogen inhibitory effect of LG-ASA, the untreated controls of the three independent experiments were arbitrarily set as 100% and the mean is presented (FIG. 23).

Since LG-ASA was added directly during bacterial infection, these results indicate a very early effect on bacterial internalization, which potentiates during ongoing release and new bacterial internalization.

Very recently it has been shown that NFκB is required for phagocytosis of S. aureus by monocytes (Zhu et al., 2014; Exp.Cell Res. 1;327(2):256-63). Based on these findings and our own observations we wanted to know if LG-ASA prevents bacterial uptake. We pre-treated human lung epithelial cells 4 hours before bacterial infection and determined internalized bacteria up to two hours post infection. To ensure that only internalized bacteria were detected, non-internalized bacteria were removed by an antibiotic wash prior to cell lysis. The data indicate a time dependent uptake of S. aureus 6850, which is blocked in presence of LG-ASA (FIG. 24A, B). A concentration dependent inhibitory effect of LG-ASA could be further demonstrated on the bacterial strain S. aureus USA300 (FIG. 24C, D). To better visualize the pathogen inhibitory effect of LG-ASA, which is visible in FIG. 24A, C the untreated controls of the three independent experiments were arbitrarily set as 100% and the mean is depicted (FIG. 24B, D).

To verify the importance of NFκB-mediated signalling onto S. aureus internalisation, NFκB was induced by TNF-α stimulation 4 hours prior bacterial infection. The activation of NFκB resulted in the enhanced uptake of S. aureus6850 and S. aureusUSA300. As a control TNF-α-induced activation was simultaneously blocked by LG-ASA, which resulted in the inhibition of TNF-α-promoted bacterial uptake, as expected (FIG. 25).

To verify the anti-pathogen potential of LG-ASA in an in vivo mouse model different co-infection settings in presence and absence of LG-ASA were tested.

As visible in FIG. 26 treatment of IAV/S. aureus co-infected mice with LG-ASA results in enhanced survival (FIG. 26A) and reduced body weight loss (FIG. 26B).

In conclusion, our results show that NFκB inhibitors such as LG-ASA act as anti-IAV/S. aureus substances in vitro and in vivo.

REFERENCES

Borgeling, Y., Schmolke, M., Viemann, D., Nordhoff, C., Roth, J. and Ludwig, S. (2014). Inhibition of 38 mitogen-activated protein kinase impairs influenza virus-induced primary and secondary host gene responses and protects mice from lethal H5N1 infection. The Journal of biological chemistry 289, 13-27.

Chertow, D. S. and Memoli, M. J. (2013). Bacterial coinfection in influenza: a • rand rounds review. JAMA: the Journal of the American Medical Association 309, 275-282.

Droebner, K., Pleschka, S., Ludwig, S. and Planz, 0. (2011). Antiviral activity of the MEK-inhibitor U0126 against pandemic H1N1v and highly pathogenic avian influenza virus in vitro and in vivo. Antiviral research 92, 195-203.

Dudek, S. E., Luig, C., Pauli, E. K., Schubert, U. and Ludwig, S. (2010). The clinically approved proteasome inhibitor PS-341 efficiently blocks influenza A virus and vesicular stomatitis virus propagation by establishing an antiviral state. Journal of virology 84, 9439-9451, Ehrhardt, C. and Ludwig, S. (2009). A new player in a deadly game: influenza viruses and the PI3K/Akt signalling pathway. Cellular microbiology 11, 863-871.

Ehrhardt, C., Marjuki, H., Wolff, T., Nurnberg, B., Planz, 0., Pleschka, S. and Ludwig, S. (2006). Bivalent role of the phosphatidylinositol-3-kinase (PI3K) during influenza virus infection and host cell defence. Cellular microbiology 8, 1336-1348.

Ehrhardt, C., Buckle, A., Hrincius, E. R., Haasbach, E., Anhlan, D., Ahmann, K., et al. (2013). The NF-kappaB inhibitor SC75741 efficiently blocks influenza virus propagation and confers a high barrier for development of viral resistance. Cellular microbiology 15, 1198-1211.

Ehrhardt, C., Wolff, T. and Ludwig, S. (2007a). Activation of phosphatidylinositol 3-kinase signaling by the nonstructural NS1 protein is not conserved among type A and B influenza viruses. Journal of virology 81, 12097-12100.

Ehrhardt, C., Wolff, T., Pleschka, S., Planz, 0., Beermann, W., Bode, J. G., et al. (2007b). Influenza A virus NS1 protein activates the PI3K/Akt pathway to mediate anti-apoptotic signaling responses. Journal of virology 81, 3058-3067.

Eierhoff, T., Hrincius, E R., Rescher, U., Ludwig, S. and Ehrhardt, C. (2010). The epidermal growth factor receptor (EGFR) promotes uptake of influenza A viruses (IAV) into host cells. PLoS pathogens 6, e1001099.

Gillet, Y., Vanhems, P., Lina, G., Bes, M., Vandenesch, F., Floret, D. and Etienne, J. (2007). Factors predicting mortality in necrotizing communityacquired pneumonia caused by Staphylococcus aureus containing Panton-Valentine leukocidin. Clinical infectious diseases: an official publication of the Infectious Diseases Society of America 45, 315-321.

Gong, J., Fang, H., Li, M., Liu, Y., Yang, K., Liu, Y. and Xu, W. (2009). Potential targets and their relevant inhibitors in anti-influenza fields. Current medicinal chemistry 16, 3716-3739.

Grundmann, H., Aires-de-Sousa, M., Boyce, J. and Tiemersma, E. (2006). Emergence and resurgence of meticillin-resistant Staphylococcus aureus as a public-health threat. Lancet 368, 874-885.

Haasbach, E., Railing, S. J., Ehrhardt, C., Droebner, K., Ruckle, A., Hrincius, E. R., et al. (2013). The NF-kappaB inhibitor SC75741 protects mice against highly pathogenic avian influenza A virus. Antiviral research 99, 336-344.

Hayden, F. (2009). Developing new antiviral agents for influenza treatment: what does the future hold? Clinical infectious diseases: an official publication of the Infectious Diseases Society of America 48 Suppl 1, S3-13.

Hayden, F. G. and Hay, A. J. (1992). Emergence and transmission of influenza A viruses resistant to amantadine and rimantadine. Current topics in microbiology and immunology 176, 119-130.

Iverson, A. R., Boyd, K. L., McAuley, J. L., Piano, L. R., Hart, M. E. and McCullers, J. A. (2011). Influenza virus primes mice for pneumonia from Staphylococcus aureus. The Journal of infectious diseases 203, 880-888.'

Iwao, Y., Ishii, R., Tomita, Y., Shibuya, Y., Takano, T., Hung, W. C., et al. (2012). The emerging ST8 methicillin-resistant *Staphylococcus aureus* clone in the community in Japan: associated infections, genetic diversity, and comparative genomics. J Infect Chemother 18, 228-240.

Lee, L T., Lee, C. W., Tung, W.1-1., Wang, S. W., Lin, C. C., Shu, J. C. and Yang, C. M. (2010). Cooperation of TLR2 with MyD88, PI3K, and Rad in lipoteichoic acid-Induced cPLA2/COX-2-dependent airway inflammatory responses. The American journal of pathology 176, 1671-1684.

Ludwig, S. (2009). Targeting cell signalling pathways to fight the flu: towards a paradigm change in anti-influenza therapy. The Journal of antimicrobial chemotherapy 64, 1-4.

Ludwig, S. (2011). Disruption of virus-host cell interactions and cell signaling pathways as an anti-viral approach against influenza virus infections. Biological chemistry 392, 837-847.

Ludwig, S. and Planz, 0. (2008). Influenza viruses and the NF-kappaB signaling pathway—towards a novel concept of antiviral therapy. Biological chemistry 389, 1307-1312.

Ludwig, S., Planz, 0., Pleschka, S. and Wolff, T. (2003). Influenza-virus induced signaling cascades: targets for antiviral therapy? Trends in molecular medicine 9, 46-52.

Ludwig, S., Wolff, T., Ehrhardt, C., Wurzer, W. J., Reinhardt, J., Planz, 0. and Pleschka, S. (2004). MEK inhibition impairs influenza B virus propagation without emergence of resistant variants. FEBS letters 561,37-43.

Marjuki, H., Alam, M. I., Ehrhardt, C., Wagner, R., Planz, 0., Klenk, H. D., et al. (2006). Membrane accumulation of influenza A virus hemagglutinin triggers nuclear export of the viral genome via protein kinase Calphamediated activation of ERK signaling. The Journal of biological chemistry 281, 16707-16715.

Mazur, 1., Wurzer, W. J., Ehrhardt, C., Pleschka, S., Puthavathana, P., Silberzahn, T., et al. (2007). Acetylsalicylic acid (ASA) blocks influenza virus propagation via its NF-kappaB-inhibiting activity. Cellular microbiology 9, 1683-1694.

Moran, G. J., Krishnadasan, A., Gorwitz, R. J., Fosheim, G. E., McDougal, L. K., Carey, R. B., et al. (2006). Methicillin-resistant *S. aureus* infections among patients in the emergency department. The New England Journal of medicine 355, 666-674.

Morens, D. M., Taubenberger, J. K. and Fauci, A. S. (2008). Predominantrote of bacterial pneumonia as a cause of death in pandemic influenza: implications for pandemic influenza preparedness. The Journal of infectious diseases 198, 962-970.

Neumann, G., Noda, T. and Kawaoka, Y. (2009). Emergence and pandemic potential of swine-origin H1N1 influenza virus. Nature 459, 931-939.

Niemann, S., Ehrhardt, C., Medina, E., Warnking, K., Tuchscherr, L., Heitmann, V., et al. (2012). Combined action of influenza virus and *Staphylococcus aureus* panton-valentine leukocidin provokes severe lung epithelium damage. The Journal of infectious diseases 206, 1138-1148.

Olschlager, V., Pleschka, S., Fischer, T., Rziha, H. J., Wurzer, W., Stitz, L., et al. (2004). Lung-specific expression of active Raf kinase resuits in increased mortality of influenza A virus-infected mice. Oncogene 23, 6639-6646.

Oviedo-Boyso, J., Cortes-Vieyra, R., Huante-Mendoza, A., Yu, H. B., Valdez-Alarcon, J. J., Bravo-Patino, A., et al. (2011). The phosphoinositide-3-kinase-Akt signaling pathway is important for *Staphylococcus aureus* internalization by endothelial cells. Infection and immunity 79, 4569-4577.

Paddock, C. D., Liu, L., Denison, A. M., Bartlett, J. H., Holman, R. C., Deleon-Carnes, M., et al. (2012). Myocardial injury and bacterial pneumonia contribute to the pathogenesis of fatal Influenza B Virus infection. The Journal of infectious diseases 205, 895-905.

Park, B. and Liu, G. Y. (2012). Targeting the host-pathogen interface for treatment of *Staphylococcus aureus* infection. Seminars in immunopathology 34, 299-315.

Parker, D. and Prince, A. (2012). Immunopathogenesis of *Staphylococcus aureus* pulmonary infection. Seminars in immunopathology 34, 281-297.

Parry, J. (2013). H7N9 avian flu infects humans for the first time. Bmj 346, f2151.

Pinto, L. H. and Lamb, R. A. (2006). The M2 proton channels of influenza A and B viruses. The Journal of biological chemistry 281, 8997-9000.

Pinto, L. H. and Lamb, R. A. (2007). Controlling influenza virus replication by inhibiting its proton channel. Molecular bioSystems 3, 18-23.

Planz, 0. (2013). Development of cellular signaling pathway inhibitors as new antivirals against influenza. Antiviral research 98, 457-468.

Pleschka, S., Wolff, T., Ehrhardt, C., Hobom, G., Planz, 0., Rapp, U. R. and Ludwig, S. (2001). Influenza virus propagation is impaired by inhibition of the Raf/MEK/ERK signalling cascade. Nature cell biology 3, 301-305.

Shilo, N. and Quach, C. (2011). Pulmonary infections and community associated methicillin resistant *Staphylococcus aureus:* a dangerous mix? Paediatric respiratory reviews 12, 182-189.

Taubenberger, J. K, and Kash, J. C. (2010). Influenza virus evolution, host adaptation, and pandemic formation. Cell host & microbe 7, 440-451.

Thorburn, K. and Riordan, A. (2012). Pulmonary bacterial coinfection in infants and children with viral respiratory infection. Expert review of antiinfective therapy 10, 909-916.

Wurzer, W. J., Ehrhardt, C., Pleschka, S., Berberich-Siebelt, F., Wolff, T., Walczak, H., et al. (2004). NF-kappaB-dependent induction of tumor necrosis factor-related apoptosis-inducing ligand (TRAIL) and Fas/FasL is crucial for efficient influenza virus propagation. The Journal of biological chemistry 279, 30931-30937.

Zhu F, Yue W, Wang Y. The nuclear factor kappa B (NF-κB) activation is required for phagocytosis of *staphylococcus aureus* by RAW 264.7 cells. Exp Cell Res. 2014 Oct. 1; 327(2):256-63.

The invention claimed is:

1. A method for inhibiting a *Staphylococcus aureus* infection and an influenza virus infection in a cell comprising contacting the cell with an effective amount of a MEK inhibitor, a p38 inhibitor and/or an NFκB inhibitor.

2. A method for inhibiting a *Staphylococcus aureus* infection in a cell comprising contacting the cell with an effective amount of a MEK inhibitor, a p38 inhibitor and/or an NFκB inhibitor.

3. The method claim 1, wherein the influenza virus infection is mediated by influenza A virus or influenza B virus.

4. The method according to claim 3, wherein the influenza A virus is H1N1, H2N2, H3N2, H6N1, H7N7, H7N9, H9N2,H10N7, H10N8 or H5N1.

5. The method according to claim 1 or 2, wherein the MEK inhibitor is selected from the group consisting of U0126, PLX-4032, AZD6244, AZD8330, AS-703026, GSK-1120212, RDEA-119, RO-5126766, RO-4987655, CI-1040, PD-0325901, GDC-0973, TAK-733, PD98059, ARRY-438162, PF-3644022 and PD184352, preferably AZD8330, GSK-1120212, U0126, GDC-0973, CI-1040, PD0325901, ARRY-438162, PF-3644022 and AZD6244.

6. The method of claim 1 or 2, wherein the p38 inhibitor is selected from the group consisting of SB202190, LY2228820, CAY10571, SB203580, Tie2 Kinase Inhibitor, 2-(4-Chlorophenyl)-4-(fluorophenyl)-5-pyridin-4-yl-1,2-dihydropyrazol-3-one, CGH 2466, SB220025, Antibiotic LL Z1640-2, TAK 715, SB202190 hydrochloride, SKF 86002, AMG548, CMPD-1, EO 1428, JX 401, ML 3403, RWJ 67657, SB 202190, SB 203580, SB 203580 hydrochloride, SB 239063, SCIO 469, SX 011, TAK 715, Pamapimod, Losmapimod (GW856553), Dilmapimod (SB681323), VX 702, VX 745, Doramapimod (BIRB 796), BMS-582949, ARRY-797, PH797804 preferably VX-702, SB202190, Pamapimod, Losmapimod (GW856553), Dilmapimod (SB681323), Doramapimod (BIRB 796), BMS-582949, ARRY-797, PH797804 and SCIO-469.

7. The method according to claim 1 or 2, wherein the NFκB inhibitor is selected from the group consisting of LASAG, SC75741, MG 132, TPCA-1, PCTC, IMD 0354, Luteolin, Caffeic acid phenethyl ester, Cardamonin, PF 184, IKK 16, SC 514, Withaferin A, Arctigenin, Bay 11-7085, PSI, PR 39, Ro 106-9920, Bay 11-7821, ML-130, Celastrol, Tanshinone IIA, HU 211, Gliotoxin, CID 2858522, Honokiol, Andrographolide, 10Z-Hymenialdisine, ACHP, Pristimerin, Sulfasalazine, ML 120B dihydrochloride, Amlexanox, 9-Methylstreptimidone, N-Stearoyl phytosphingosine, 2-(1,8-naphthyridin-2-yl)-Phenol, 5-Aminosalicylic acid, BAY 11-7085, Ethyl 3,4-Dihydroxycinnamate, Helanalin, NE-KB Activation Inhibitor II, JSH-23, Glucocorticoid Receptor Modulator, CpdA, PPM-18, ASA, Pyrrolidinedithiocarbamic acid ammonium salt, (R)-MG132, SC75741, Rocaglamide, Sodium salicylate, QNZ, PS-1145, CAY10512, bortezomib, salsalate, resveratrol, deoxyspergualin, sulindac, thalidomide, AGRO-100, CHS 828 and/or Curcumin, preferably, bortezomib, curcumin, ASA, salsalate, resveratrol, sodium salicylate, LASAG, SC75741, deoxyspergualin, sulindac, thalidomide, AGRO-100 and/or CHS 828.

8. The method according to claim 1, wherein the MEK inhibitor, the p38 inhibitor and/or the NFκB inhibitor are combined with one or more inhibitors targeting the influenza virus and/or the *Staphylococcus aureus*.

9. The method according to claim 2, wherein the MEK inhibitor, the p38 inhibitor and/or the NFκB inhibitor are combined with one or more inhibitors targeting the *Staphylococcus aureus*.

10. The method according to claim 8 wherein the one or more inhibitors targeting the influenza virus is a neuraminidase inhibitor.

11. The method according to claim 8, wherein the one or more inhibitor(s) targeting the *Staphylococcus aureus* is an antibiotic.

12. The method of claim 1 or 2, wherein the cell is a vertebrate cell.

13. The method according to claim 10, wherein the neuraminidase inhibitor is oseltamivir phosphate, zanamivir, oseltamivir or peramivir.

14. The method according to claim 11, wherein the antibiotic is Gentamicin, Rifampicin, Lysosthaphin, Erythromycin, Levofloxacin, Vancomycin, Teicoplanin, Penicillin or Oxacillin.

15. The method according to claim 12, wherein the vertebrate cell is a human cell.

\* \* \* \* \*

UNITED STATES PATENT AND TRADEMARK OFFICE
CERTIFICATE OF CORRECTION

PATENT NO. : 10,456,440 B2
APPLICATION NO. : 15/310836
DATED : October 29, 2019
INVENTOR(S) : Christina Ehrhardt et al.

It is certified that error appears in the above-identified patent and that said Letters Patent is hereby corrected as shown below:

In the Claims

At Column 40, Line 57, "method" should be -- method according to --.

At Column 40, Line 62, "H9N2,H10N7, H10N8or H5N1." should be -- H9N2, H10N7, H10N8 or H5N1. --.

At Column 41, Line 15, "PH797804 preferably" should be -- PH797804, preferably --.

At Column 41, Line 31, "NE-KB" should be -- NF-κB --.

At Column 42, Line 6, "and/or" should be -- and --.

At Column 42, Line 28, "Lysosthaphin," should be -- Lysostaphin, --.

Signed and Sealed this
Fifteenth Day of September, 2020

Andrei Iancu
*Director of the United States Patent and Trademark Office*